(12) United States Patent
Babcook et al.

(10) Patent No.: US 7,265,212 B2
(45) Date of Patent: Sep. 4, 2007

(54) ANTI-CD45RB ANTIBODIES

(75) Inventors: John S. Babcook, Vancouver (CA); Ian Foltz, Vancouver (CA); Chadwick T. King, Vancouver (CA); Varghese Palathumpat, Fremont, CA (US); Xiao-Dong Yang, Palo Alto, CA (US)

(73) Assignee: Amgen Fremont Inc., South San Francisco, CA (US)

( * ) Notice: Subject to any disclaimer, the term of this patent is extended or adjusted under 35 U.S.C. 154(b) by 411 days.

(21) Appl. No.: 10/309,764

(22) Filed: Dec. 2, 2002

(65) Prior Publication Data

US 2003/0232009 A1 Dec. 18, 2003

Related U.S. Application Data

(60) Provisional application No. 60/337,276, filed on Dec. 3, 2001.

(51) Int. Cl.
*C07K 16/28* (2006.01)
*G01N 33/53* (2006.01)

(52) U.S. Cl. .................... 530/388.75; 530/388.15; 530/391.7; 424/142.1; 424/173.1

(58) Field of Classification Search ............. None
See application file for complete search history.

(56) References Cited

U.S. PATENT DOCUMENTS

| | | | |
|---|---|---|---|
| 6,024,957 A | 2/2000 | Lazarovits et al. | |
| 6,075,181 A | 6/2000 | Kucherlapati et al. | |
| 6,099,838 A | 8/2000 | Lazarovits et al. | |
| 6,106,834 A | 8/2000 | Lazarovits et al. | |

OTHER PUBLICATIONS

Rudikoff et al. Single amino acid substitution altering antigen-binding specificity. Proc. Natl. Acad. Sci. 1982; 79: 1979-1983.*
Panka et al. Variable region framework differences result in decreased or increased affinity of variant anti-digoxin antibodies. Proc. Natl. Acad. Sci. 1988; 85: 3080-3084.*
Schiffenbauer et al. Prevention of Experimental Allergic Encephalomyelitis by an antibody to CD45RB. Cellular Immunology, 1998; 190: 173-182.*
Green et al. Antigen-specific human monoclonal antibodies from mice engineered with human Ig heavy and light chain YACs. Nature Genetics, 1994; 7: 13-21.*
Wroblewski et al. CD45-mediated signals can trigger shedding of lymphocyte L-selectin. International Immunology. 1996; 9: 555-562.*

Babcook, et al., "A novel strategy for generating monoclonal antibodies from single, isolated lymphocytes producing antibodies of defined specificities", Proc. Natl. Acad. Sci. USA, vol. 93, pp. 7843-7848, (Jul. 1996).
Green, et al., "Antigen-specific human monoclonal antibodies from mice engineered with human Ig heavy and light chan YACs", Nature Genetics, vol. 7, pp. 13-21, (May 1994).
Green, et al., "Regulation of B cell development by variable gene complexity in mice reconstituted with human immunoglobulin yeast artificial chromosomes", J. Exp. Med., vol. 188, No. 3, pp. 483-495, (Aug. 3, 1998).
Lazarovits, et al., "Mechanisms of induction of renal allograft tolerance in DC45RB-treated mice", Kidney Int., vol. 55, pp. 1303-1310, (1999).
Lazarovits, et al., "Prevention and reversal of renal allograft rejection by antibody against CD45RB", Nature, vol. 380, pp. 717-720, (Apr. 25, 1996).
Mendez, et al., "Functional transplant of megabase human immunoglobulin loci recapitulates human antibody response in mice", Nature Genetics, vol. 15, pp. 146-156, (Feb. 15, 1997).
Terskikh, et al., "'Peptabody': A new type of high avidity binding protein", Biochemistry, vol. 94, pp. 1663-1668, (Mar. 1997).
Zhang, et al., "Prevention and reversal of renal allograft rejection by monoclonal antibody to CD45RB in the mouse model", Transplant Proc., vol. 27, No. 1, pp. 389-3826, (1995).
Basadonna, et al., "Antibody-mediated targeting of CD45 isoforms: A novel immunotherapeutic strategy", Proc. Natl. Acad. Sci. USA, vol. 95, pp. 3821-3826, (Mar. 1998).
International Preliminary Examination Report mailed on Mar. 23, 2005.
Luke et al., "Anti-CD45RB Monoclonal Antibody-Mediated Transplantation Tolerance," *Current Molecular Medicine*, 2001, 1, 533-543.
Zhong et al., "Monoclonal antibody against CD45RB for the therapy of rejection and autoimmune diseases," *J. Mol. Med.*, 1998, 76: 527-580.
Supplementary Partial European Search Report under Rule 46, paragraph 1 of the European Patent Convention, Application No. EP 02 78 6850.

* cited by examiner

*Primary Examiner*—Christina Chan
*Assistant Examiner*—Zachary Skelding
(74) *Attorney, Agent, or Firm*—Knobbe, Martens, Olson & Bear LLP

(57) ABSTRACT

Antibodies which specifically recognize the human CD45 isoform RB are presented. These antibodies may be used to block undesirable immune reactions in patients with transplant rejection and autoimmune diseases such as rheumatoid arthritis, multiple sclerosis and autoimmune diabetes. Preferred antibodies are fully human, monoclonal antibodies.

8 Claims, 41 Drawing Sheets

| Single Cell | Vgamma/D/J | FR1 | CDR1 | FR2 | CDR2 |
|---|---|---|---|---|---|
| — | Germline | QVQLVESGGGVVQPGRSLRLSCAASGFTFS | SYGMH | WVRQAPGKGLEWVA | VIWYDGSNKYYADSVKG |
| sc009 | VH3-33/D1-7/JH4b | ------------------------------ | N---- | -------------- | ----KRF--G------- |
| sc026 | | ------------------------------ | N---- | -------------- | ----------------- |
| sc446 | VH3-33/DIR3/JH4b | -----------K------------------ | N---- | -------------- | ----K-F---------- |
| sc606 | | ---A-------------------------- | N---- | -------------- | I---K-F---------- |
| sc713 | | ------------------------------ | N---- | -------------- | ----K-F---------- |
| sc275 | VH3-33/DIR5/JH4b | ------------------------------ | KF--- | -------------- | -----TY---------- |
| sc324 | | ------------------------------ | KF--- | ------D------- | -------Y--------- |
| sc413 | | ------------------------------ | ----- | ------D------- | -------Y--------- |
| sc416 | | ------------------------------ | R---- | ------D------- | ----------------- |
| sc439 | VH3-33/D21-10/JH4b | --------------V--E------------ | N---- | -------------- | ----K-F---------- |
| sc487 | | ---------------V-------------- | N---- | -------------- | ----K-F---------- |
| sc493 | VH3-33/DIR1/JH4b | ---------------V-------------- | N---- | ------D------- | ----K-F---------- |
| sc502 | | ---------------V-------------- | N---- | -------------- | ----K-F---------- |
| sc525 | | ---------------V-------------- | N---- | -------------- | ----K-F---------- |
| sc593 | | ---------------V-------------- | N---- | -------------- | ----K-F---------- |
| — | Germline | EVQLLESGGGLVQPGGSLRLSCAASGFTFS | SYAMS | WVRQAPGKGLEWVS | AISGSGGSTYYADSVKG |
| sc475 | VH3-23/DIR3/JH4b | A------I--------------------- | ----- | -------------- | -----F---R------- |
| — | Germline | QVQLQESGPGLVKPSETLSLTCTVSGGSIS | SYYWS | WIRQPAGKGLEWIG | RIYTSGSTNYNPSLKS |
| sc539 | | ------------------------------ | GS--- | -------------- | --HST-K-A-------- |
| sc556 | VIV-4/4.3/D3-9/JH4b | ------------------------------ | G---- | -------------- | --H-T-K-A-------- |
| sc569 | | ------------------------------ | G---- | -------------- | --H-T-K-A--S----- |
| — | Germline | QVQLVESGGGLVKPGGSLRLSCAASGFTFS | DYYMS | WIRQAPGKGLEWVS | YISSSGSTIYYADSVKG |
| sc662 | VH3-11/DIR5/JH4b | ----------D-----------------S- | G--L- | -------------- | -----L--F-K------ |
| sc648 | | ------------------------------N | V---N | -------------- | -----T-S-A------- |
| sc636 | VH3-11/D1-7/JH4b | ---H-------------------------I | N---T | -------------- | -----L----------- |

FIG. 1A

| Single cell | Vgamma/D/J | FR3 | CDR3 | FR4 | |
|---|---|---|---|---|---|
| - | Germline | RFTISRDNSKNTLYLQMNSLRAEDTAVYYCAR | | WGQGTLVTVSS | SEQ ID NO: 1 |
| sc009 | VH3-33/D1-7/JH4b | ------------------------------ | TTDY | -----M----- | SEQ ID NO: 2 |
| sc026 | | ------------------------------ | GGGDFDY | ----------- | SEQ ID NO: 3 |
| sc446 | VH3-33/DIR3/JH4b | ---------------V-------------- | GGGDFDY | ----------- | SEQ ID NO: 4 |
| sc606 | | -----N-----V------------------ | GGGDIDF | ----------- | SEQ ID NO: 5 |
| sc713 | | -----FEK---------------------- | GGGDFDY | ----------- | SEQ ID NO: 6 |
| sc275 | | ------------------------------ | GGGSFDY | ----------- | SEQ ID NO: 7 |
| sc324 | VH3-33/DIR5/JH4b | ---------------------A-------- | GGGSFDY | ----------- | SEQ ID NO: 8 |
| sc413 | | ------------------------------ | GGGSFDY | ----------- | SEQ ID NO: 9 |
| sc416 | | -------------V---------------- | GGGSFDY | ----------- | SEQ ID NO: 10 |
| sc439 | VH3-33/D21-10/JH4b | -------MQ----D---------------- | GGGDFDY | --------I-- | SEQ ID NO: 11 |
| sc487 | | -------Q---S------------------ | GGGDFDF | ----------- | SEQ ID NO: 12 |
| sc493 | | -------Q---S------------------ | GGGDFDF | ----------- | SEQ ID NO: 13 |
| sc502 | VH3-33/DIR1/JH4b | -------Q---S------------------ | GGGDFDF | ----------- | SEQ ID NO: 14 |
| sc525 | | -------Q---S------------------ | GGGDFDF | ----------- | SEQ ID NO: 15 |
| sc593 | | -------Q---S------------------ | GGGDFDF | ----------- | SEQ ID NO: 16 |
| - | Germline | RFTISRDNSKNTLYLQMNSLRAEDTAVYYCAK | | WGQGTLVTVSS | SEQ ID NO: 17 |
| sc475 | VH3-23/DIR3/JH4b | -----------------V------------ | EVMGPIFFDY | ----------- | SEQ ID NO: 18 |
| - | Germline | RVTMSVDTSKNQFSLKLSSVTAADTAVYYCAR | | WGQGTLVTVSS | SEQ ID NO: 19 |
| sc539 | | --I--L-----L-----T------------ | DYDFLTGYFDY | ----------- | SEQ ID NO: 20 |
| sc556 | VIV-4/4.3/D3-9/JH4b | --I--------L-----T------------ | DYDFLTGYFDY | ----------- | SEQ ID NO: 21 |
| sc569 | | --I--------L-----T------------ | DYDFLTGYFDY | ----------- | SEQ ID NO: 22 |
| - | Germline | RFTISRDNAKNSLYLQMNSLRAEDTAVYYCAR | | WGQGTLVTVSS | SEQ ID NO: 23 |
| sc662 | VH3-11/DIR5/JH4b | ------KT-H-------------------- | RTGTTTVFDY | ----------- | SEQ ID NO: 24 |
| sc648 | | ------------------------------ | RTGSTTVFDY | ----------- | SEQ ID NO: 25 |
| sc636 | VH3-11/D1-7/JH4b | --------F--------------------- | RAATVTTFDY | ----------- | SEQ ID NO: 26 |

FIG. 1B

| Single Cell | Vkappa/J | FR1 | CDR1 | FR2 | CDR2 |
|---|---|---|---|---|---|
| - | Germline | DIVMTQTPLSLSVTPGQPASISC | KSSQSLLHSDGKTYLY | WYLQKPGQPPQLLIY | EVSNRFS |
| sc009 | | --------------------- | ---------------- | --------------- | ------- |
| sc275 | A2/JK5 | --------------------- | ---------------- | --------------- | ------- |
| sc324 | | --------------------- | -------------F-- | --------------- | ------- |
| sc413 | | --------------------- | -------------F-- | --------------- | ------- |
| sc416 | | --------------------- | ----------R--F-- | --------------- | ------- |
| - | Germline | EIVMTQSPATLSVSPGERATLSC | RASQSVSSN#LA | WYQQKPGQAPRLLIY | GASTRAT |
| sc026 | | ----------V----------- | ----TI-GSY-- | --------------- | --F---- |
| sc439 | | --------------------- | ----NL-GKY-- | ------------SR- | --T---- |
| sc446 | | ---------L----------- | ----NI-G-Y-- | -----R------R-- | S--S--- |
| sc487 | | K--------------------- | -------G-Y-- | -----R--------- | ------- |
| sc493 | L2/JK4 | K--V------------------ | ----C---GSY-- | -----R--------- | ------- |
| sc502 | | K--------------------- | --------G-Y-- | -----RR-------- | ------- |
| sc525 | | K--------------------- | ----L-GSY-- | -----R--------- | ------- |
| sc593 | | --------------------- | --------G-Y-- | -----R--------- | ------- |
| sc662 | | --V------------------- | ----N--#-- | -----R--------- | ---V--- |
| sc648 | | --------------------- | ----INN-#-- | -------S------- | ------- |
| sc636 | | ---L------------------ | ----R--#-- | --------------- | ------- |
| sc713 | | --------------------- | ----L-GSY-- | --------------- | S------ |
| - | Germline | EIVLTQSPGTLSLSPGERATLSC | RASQSVSSSYLA | WYQQKPGQAPRLLIY | GASSRAT |
| sc475 | A27/JK4 | --------------------- | ----II--A-- | --------------- | ------- |
| - | Germline | DVVMTQSPLSLPVTLGQPASISC | RSSQSLVYSDGNTYLN | WFQQRPGQSPRRLIY | KVSNWDS |
| sc539 | | --------------------- | --------G------- | -------H------- | ------- |
| sc556 | A1/JK1 | --------------------- | ---------------- | -------H------- | ------- |
| sc569 | | --------------------- | ---------------- | --------------- | ------- |
| - | Germline | EIVMTQSPATLSVSPGERATLSC | RASQSVSSNLA | WYQQKPGQAPRLLIY | GASTRAT |
| sc606 | L2/JK5 | K--------------------- | -------------- | --H--------P--- | ------- |

*FIG. 2A*

| Single Cell | Vkappa/J | FR3 | CDR3 | FR4 | SEQ ID NO |
|---|---|---|---|---|---|
| - | Germline | GVPDRFSGSGSGTDFTLKISRVEAEDVGVYYC | | FGQGTRLEIK | SEQ ID NO: 27 |
| sc009 | | ----------L-W------------------ | MQSIQLPIT | ---------- | SEQ ID NO: 28 |
| sc275 | | -------------------------------- | MQSIQFPIT | ---------- | SEQ ID NO: 29 |
| sc324 | A2/JK5 | -----------I------------------- | MQSIQFPIT | ---------- | SEQ ID NO: 30 |
| sc413 | | -----------I------------------- | MQSIQFPIT | ---------- | SEQ ID NO: 31 |
| sc416 | | ------G------------------------ | MQSIQFPIT | -------E-- | SEQ ID NO: 32 |
| - | Germline | GIPARFSGSGSGTEFTLTISSLQSEDFAVYYC | | LTFGGGTKVEIK | SEQ ID NO: 33 |
| sc026 | | -------------------------------- | QQYNNWPPLT | -----R----- | SEQ ID NO: 34 |
| sc439 | | -V------------S----------------- | QQYNNWPPLT | ----------- | SEQ ID NO: 35 |
| sc446 | | ---D---------------------------- | QQYNNWPPLT | ------M---- | SEQ ID NO: 36 |
| sc487 | | -------------------------------- | QQYGKWPPLT | ----------- | SEQ ID NO: 37 |
| sc493 | | -------------------------------- | QQYGKWPPLT | ----------- | SEQ ID NO: 38 |
| sc502 | L2/JK4 | -------------------------------- | QQYGKWPPLT | ----------- | SEQ ID NO: 39 |
| sc525 | | -------------------------------- | QQYGKWPPLT | ----------- | SEQ ID NO: 40 |
| sc593 | | -------------------------------- | QQYGKWPPLT | ----------- | SEQ ID NO: 41 |
| sc662 | | -------------N------------------ | QQYNKWPLT | ----------- | SEQ ID NO: 42 |
| sc648 | | ---K---------------------------- | QQYNKWPLT | ----------- | SEQ ID NO: 43 |
| sc636 | | -------------------------------- | QQYNNWPLT | ----------- | SEQ ID NO: 44 |
| sc713 | | -------------------------------- | QQYNNWPPLT | ----------- | SEQ ID NO: 45 |
| - | Germline | GIPDRFSGSGSGTDFTLTISRLEPEDFAVYYC | | FGGGTKVEIK | SEQ ID NO: 46 |
| sc475 | A27/JK4 | --------------H----------------- | QQYGSTPLT | ---------- | SEQ ID NO: 47 |
| - | Germline | GVPDRFSGSGSGTDFTLKISRVEAEDVGVYYC | | FGQGTKVEIK | SEQ ID NO: 48 |
| sc539 | | -----------I------------------- | MQGTHWPPT | -----R---- | SEQ ID NO: 49 |
| sc556 | A1/JK1 | -----------I------------------- | MQGTHWPPT | -----R---- | SEQ ID NO: 50 |
| sc569 | | ----A--------------------------- | MQGTHWPPT | -----R---- | SEQ ID NO: 51 |
| - | Germline | GIPARFSGSGSGTEFTLTISSLQSEDFAVYYC | | FGQGTRLEIK | SEQ ID NO: 52 |
| sc606 | L2/JK5 | -------------------------------- | QQYNKWPPVT | ---------- | SEQ ID NO: 53 |

FIG. 2B

Binding of recombinant anti-CD45RB antibodies to transiently transfected CHO cells:

FIG. 4A1
6G3 - Binding to Human and Macaque T cells:
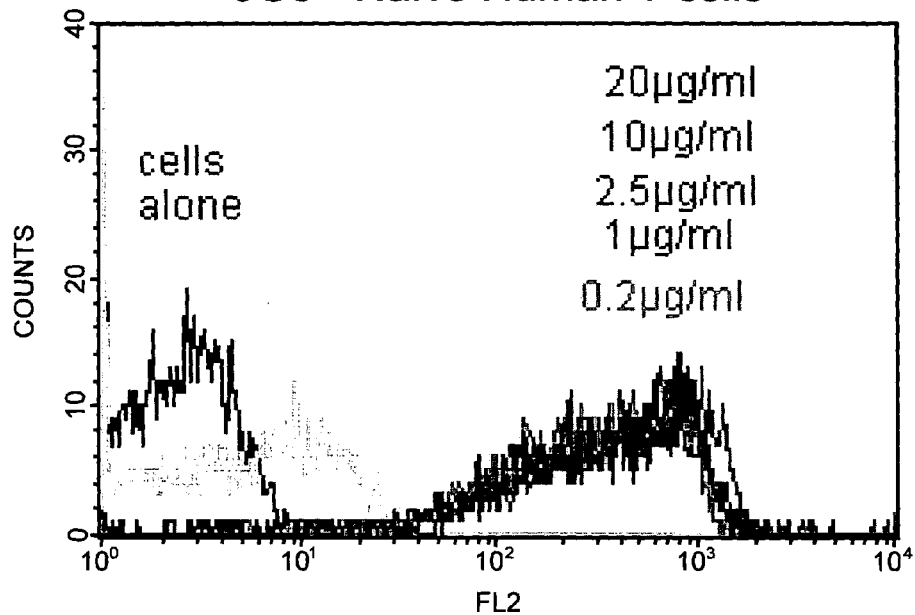
FIG. 4A2
6G3 - Binding to Human and Macaque T cells:
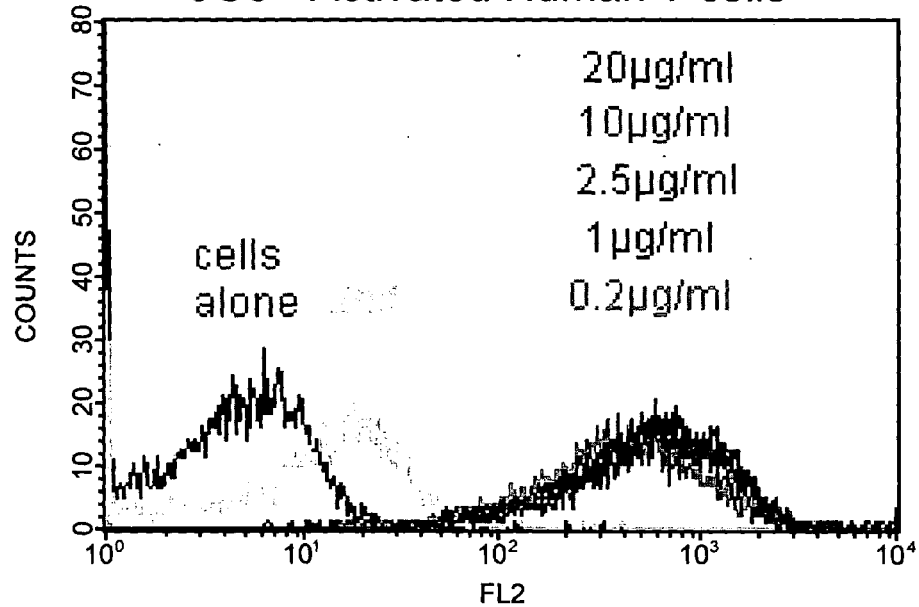

FIG. 4B1
6G3 - Binding to Human and Macaqu T cells:
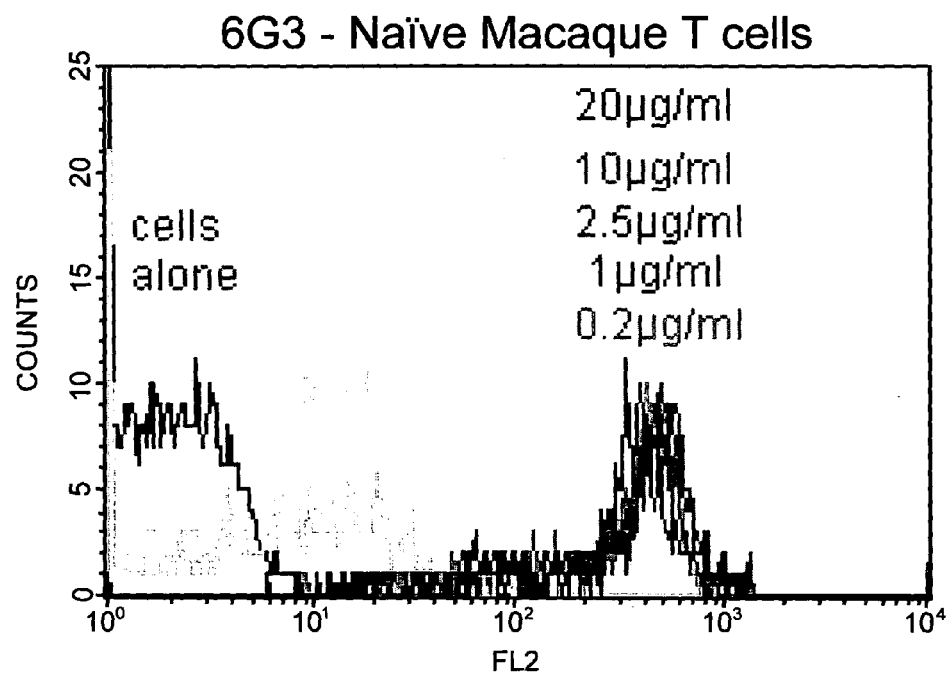
FIG. 4B2
6G3 - Binding to Human and Macaque T cells:
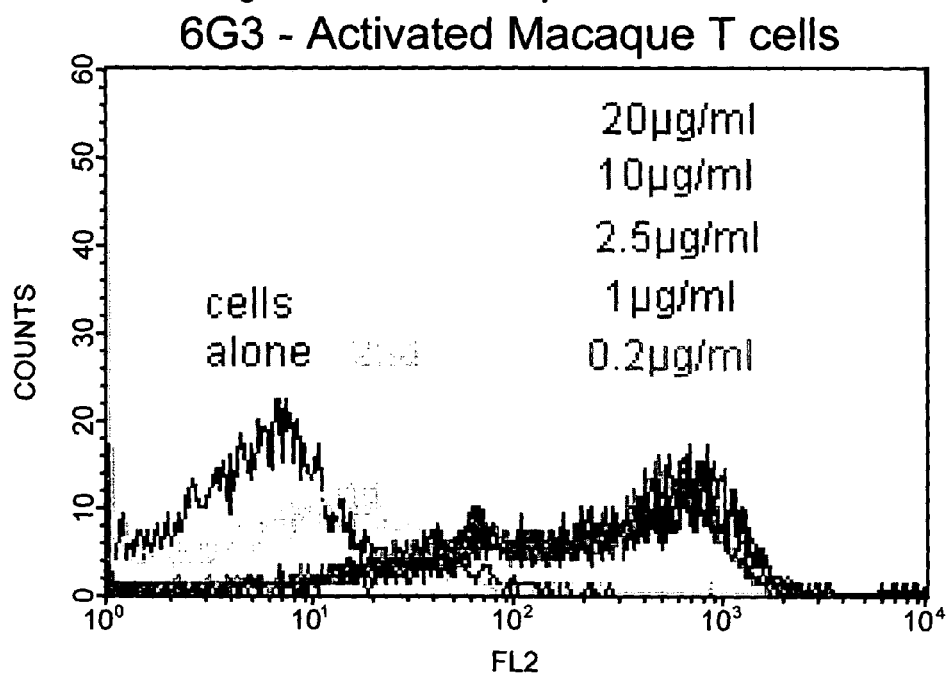

FIG. 5A1
Bin 1: Human T cell-specific - Peptide Binding Antibodies:
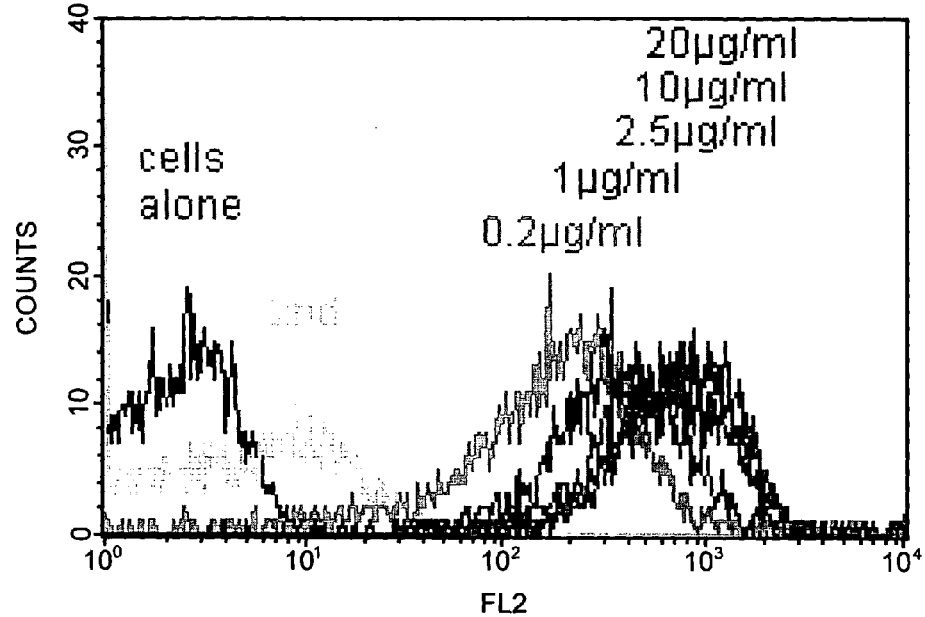
sc026 - Naïve Human T cells
FIG. 5A2
Bin 1: Human T cell-specific - Peptide Binding Antibodies:
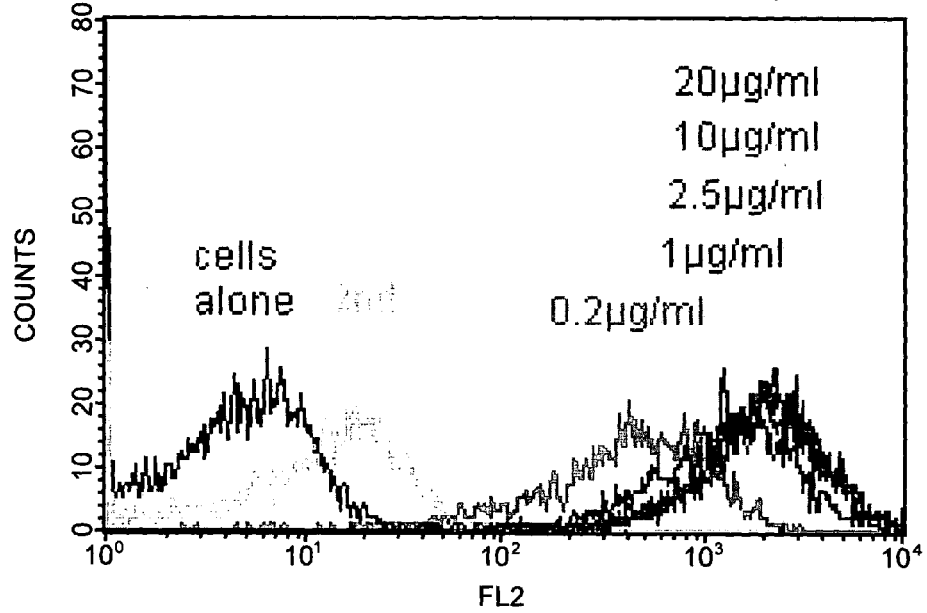
sc026 - Activated Human T cells FIG. 5B1
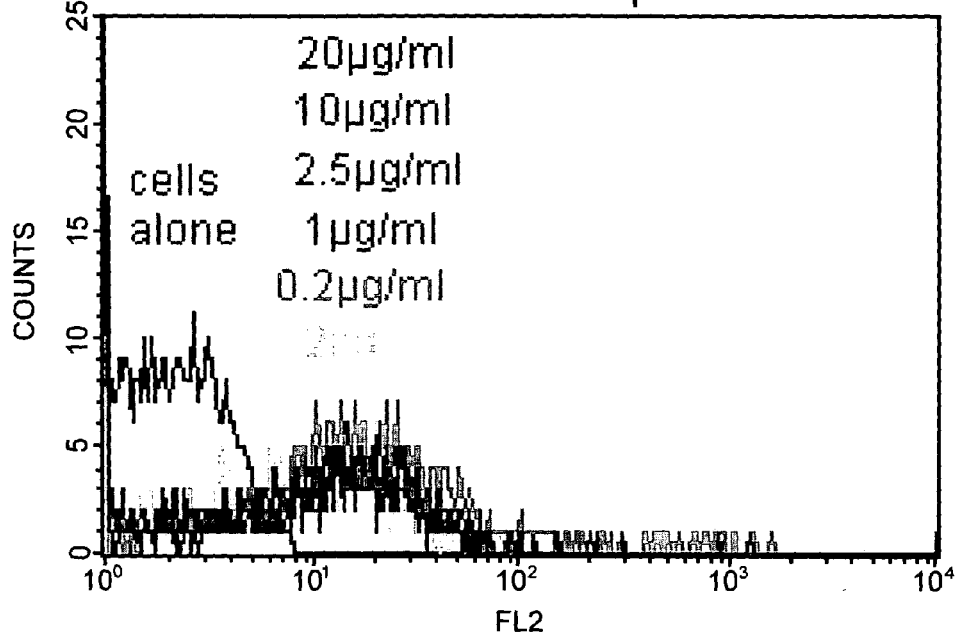
FIG. 5B2
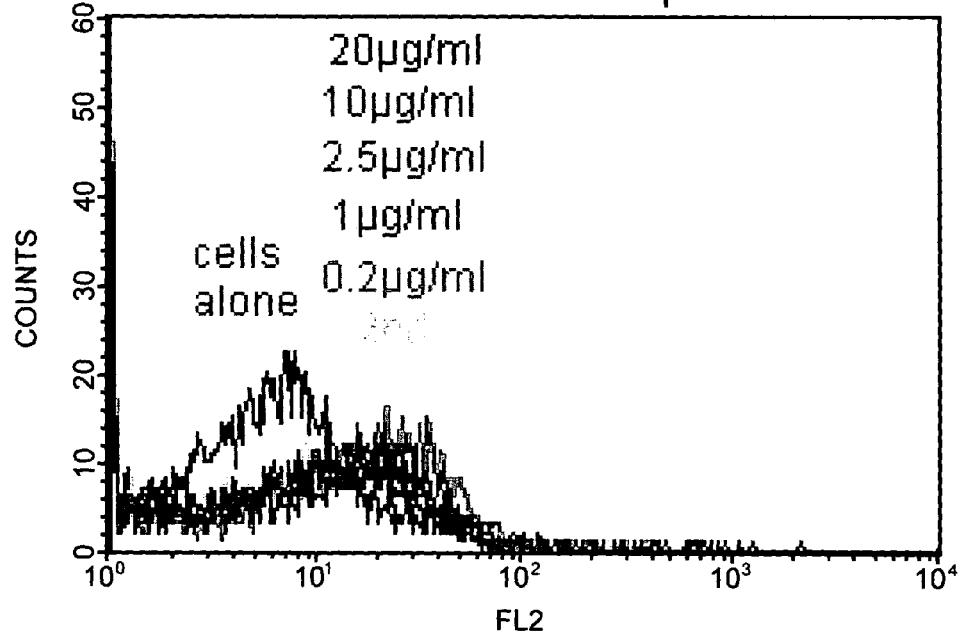

FIG. 6A1
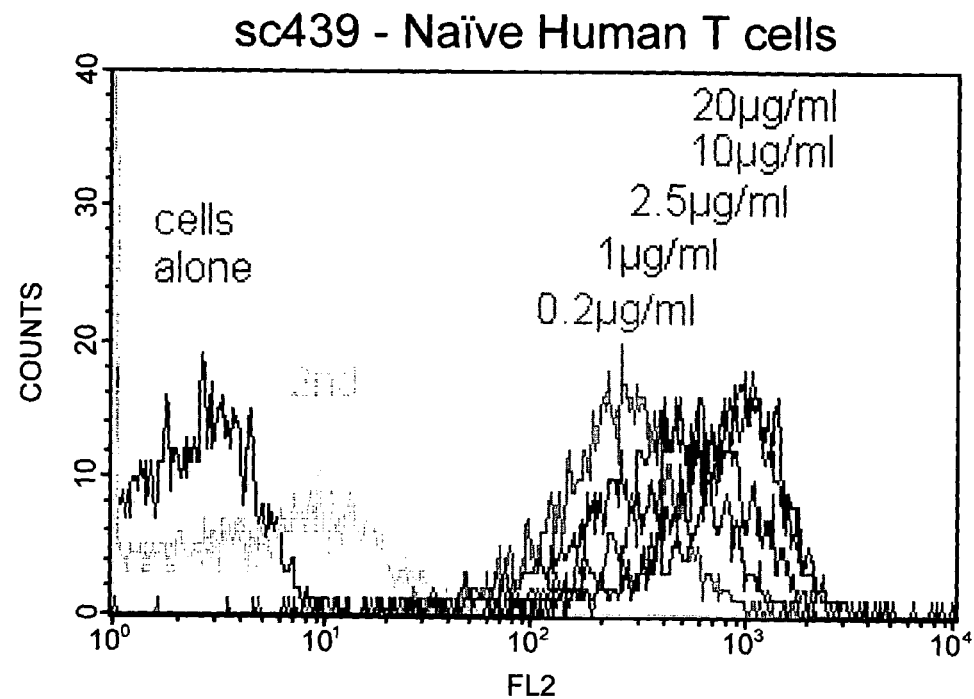
FIG. 6A2
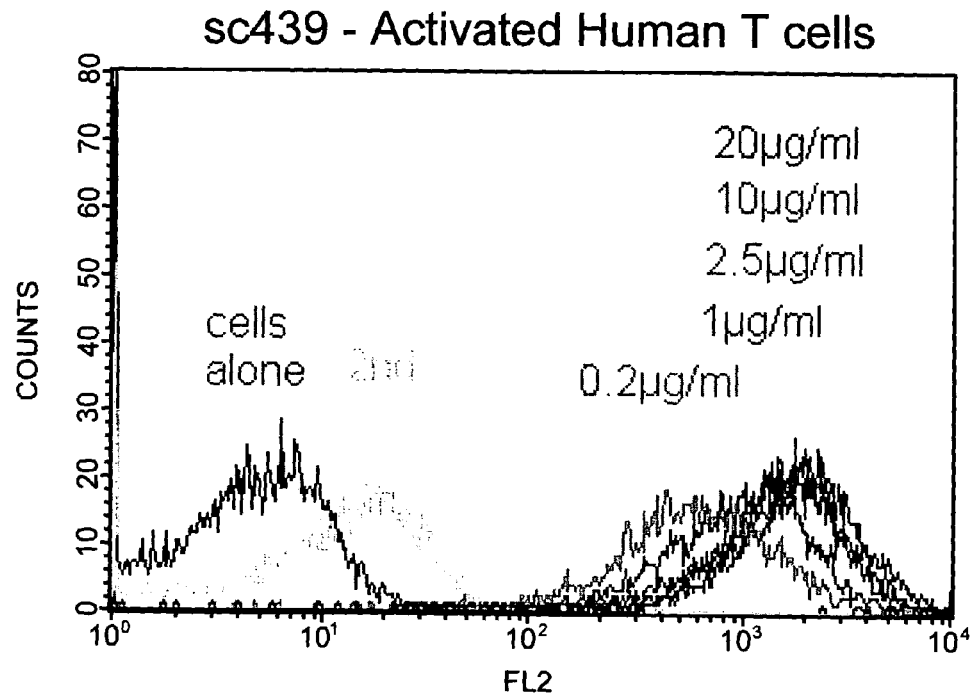

FIG. 6B1
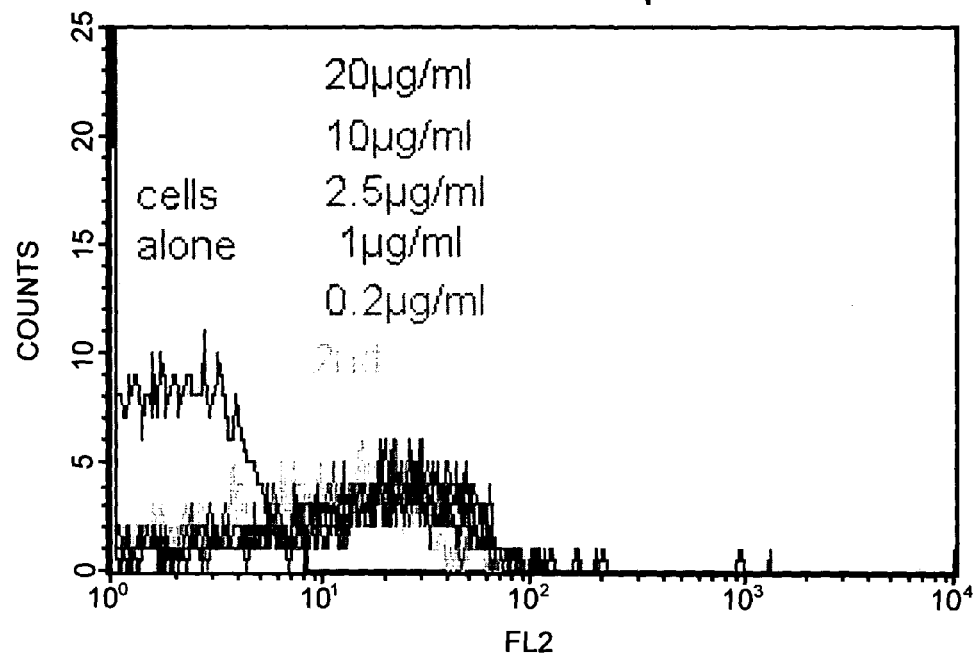
FIG. 6B2
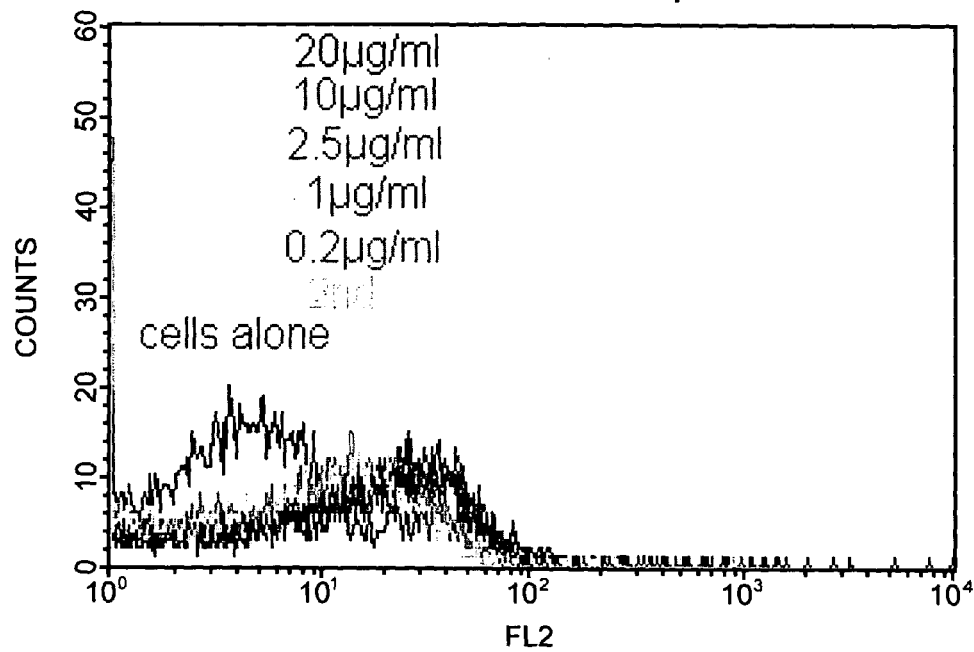

*FIG. 7A1*
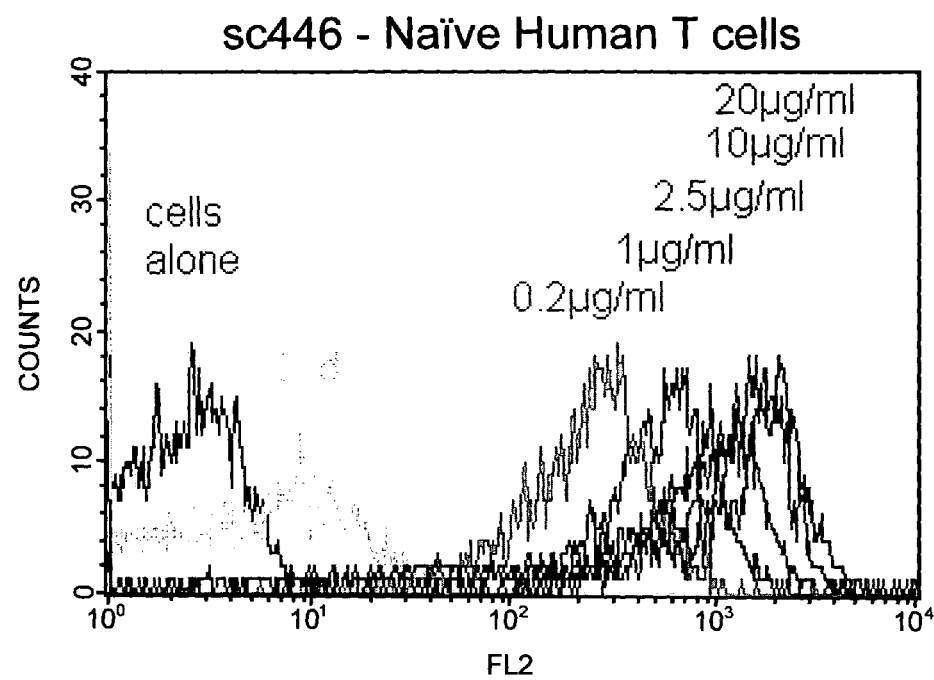
*FIG. 7A2*
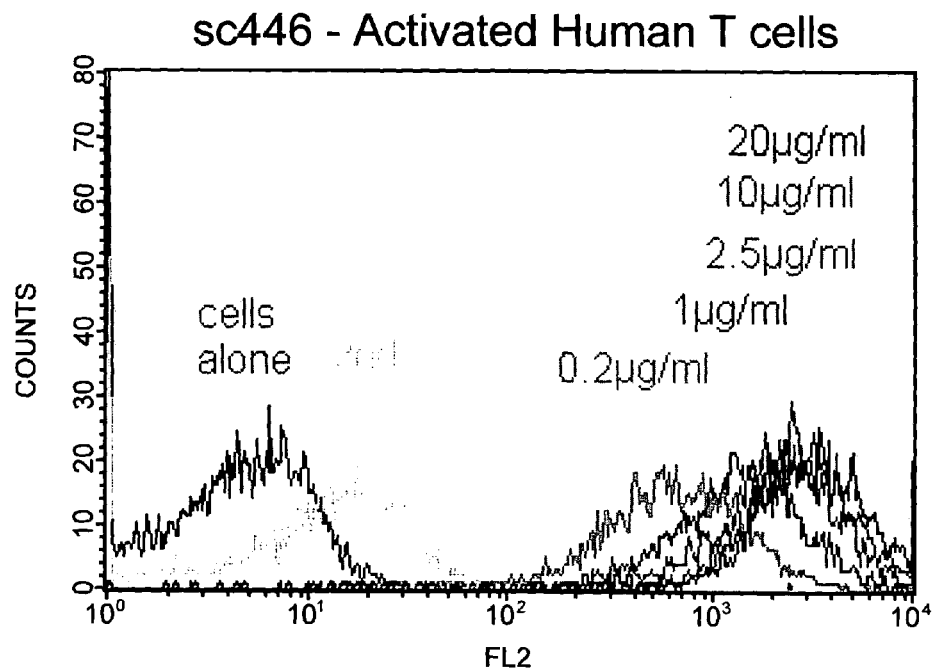

FIG. 7B1
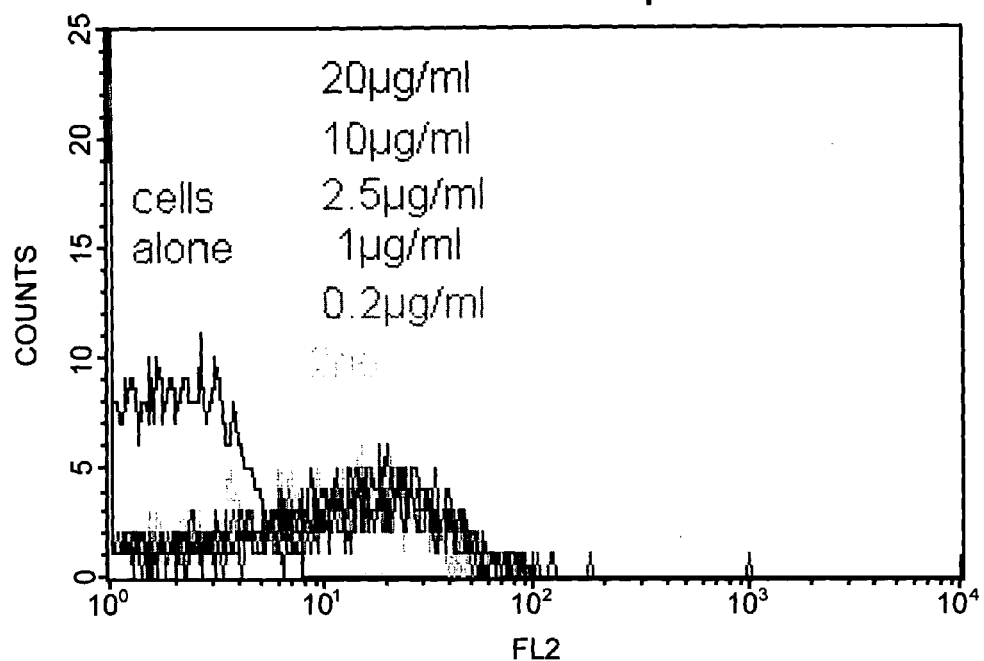
FIG. 7B2
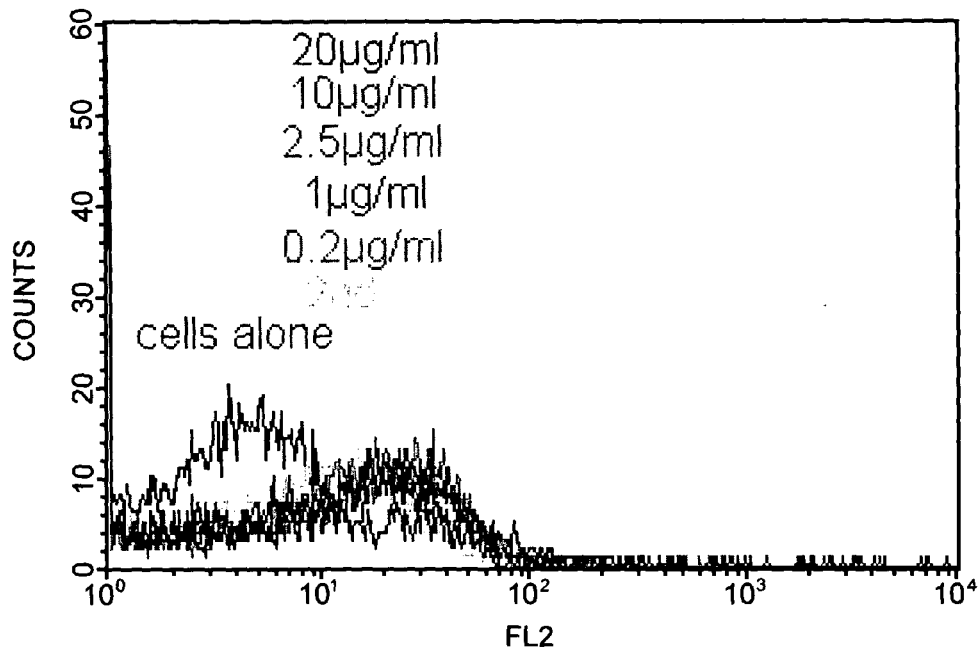

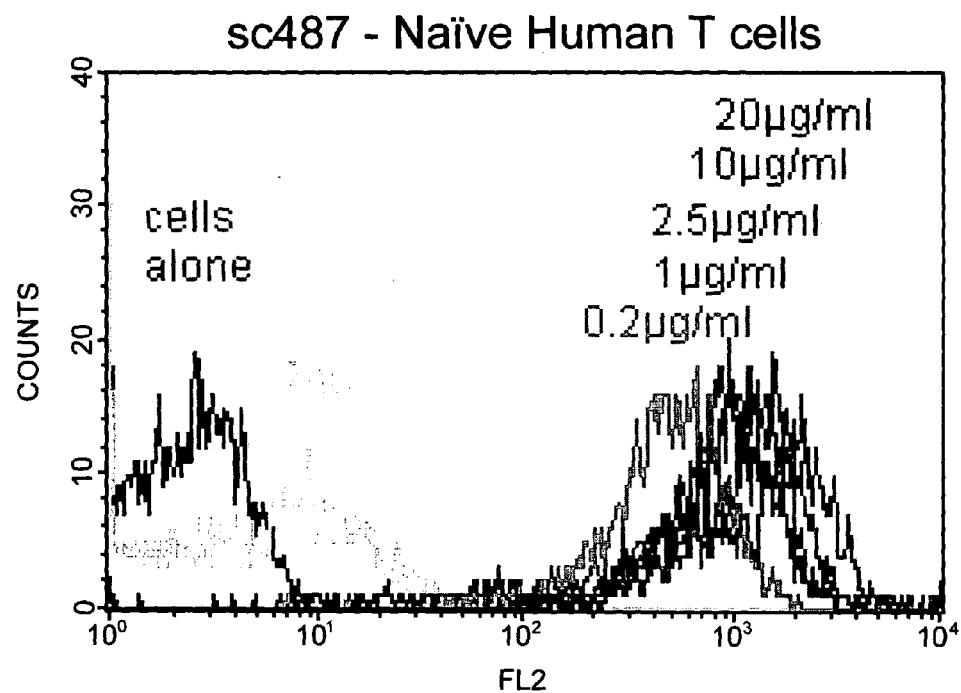
FIG. 8A1
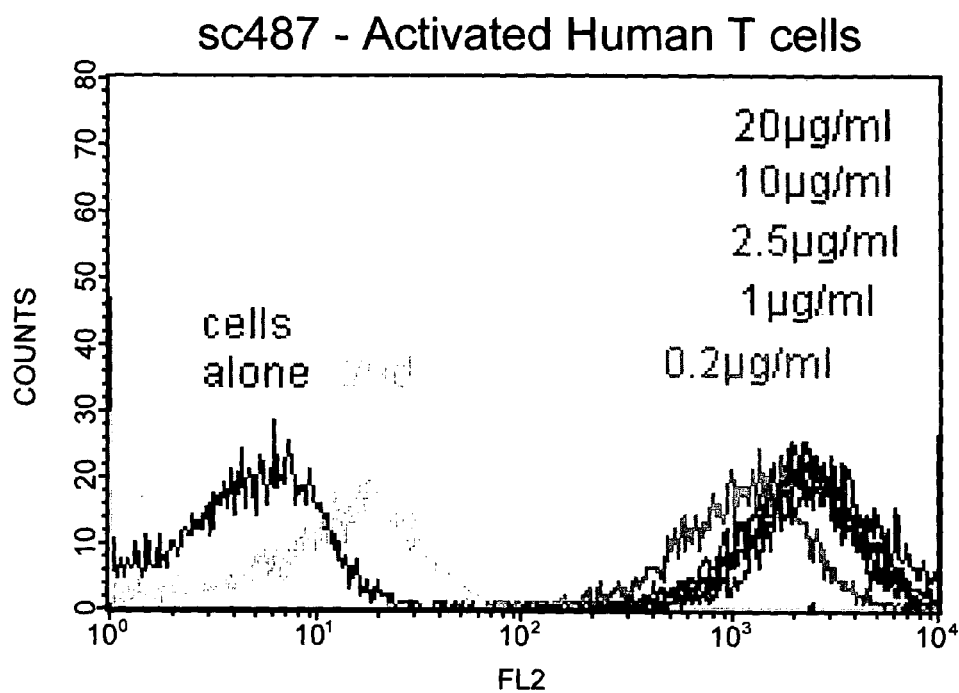
FIG. 8A2

FIG. 8B1
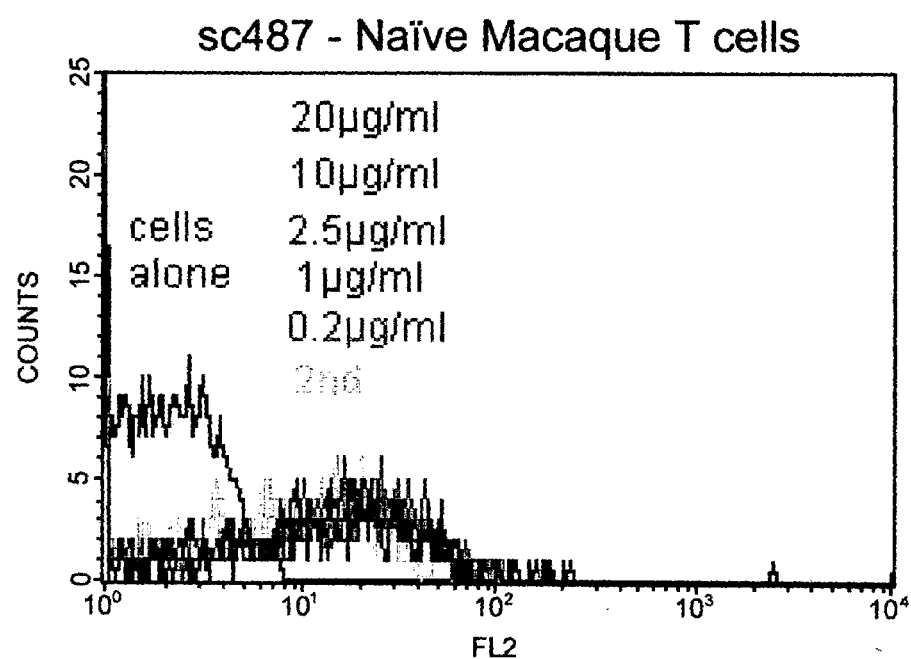
FIG. 8B2
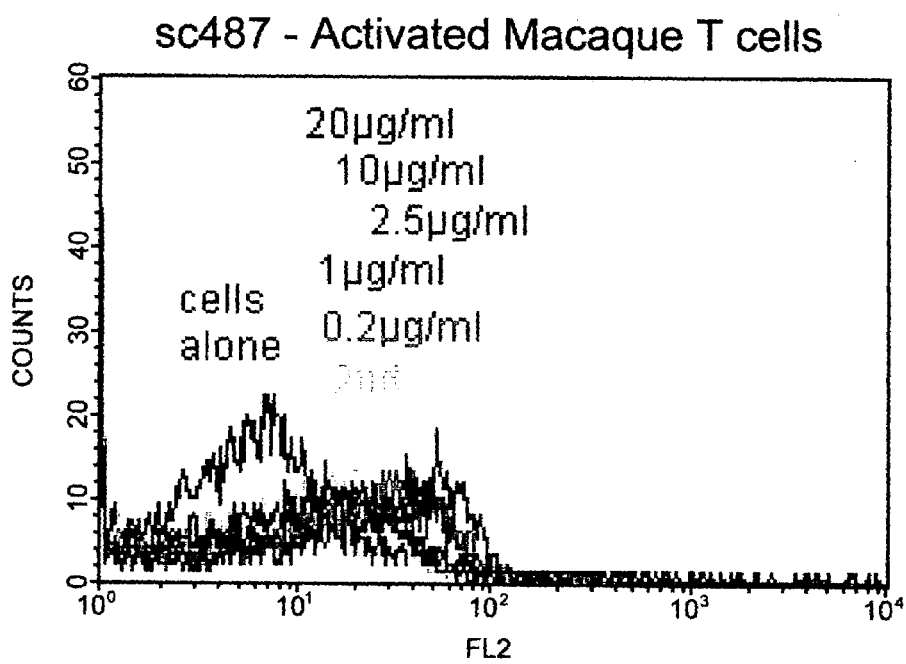

FIG. 9A1
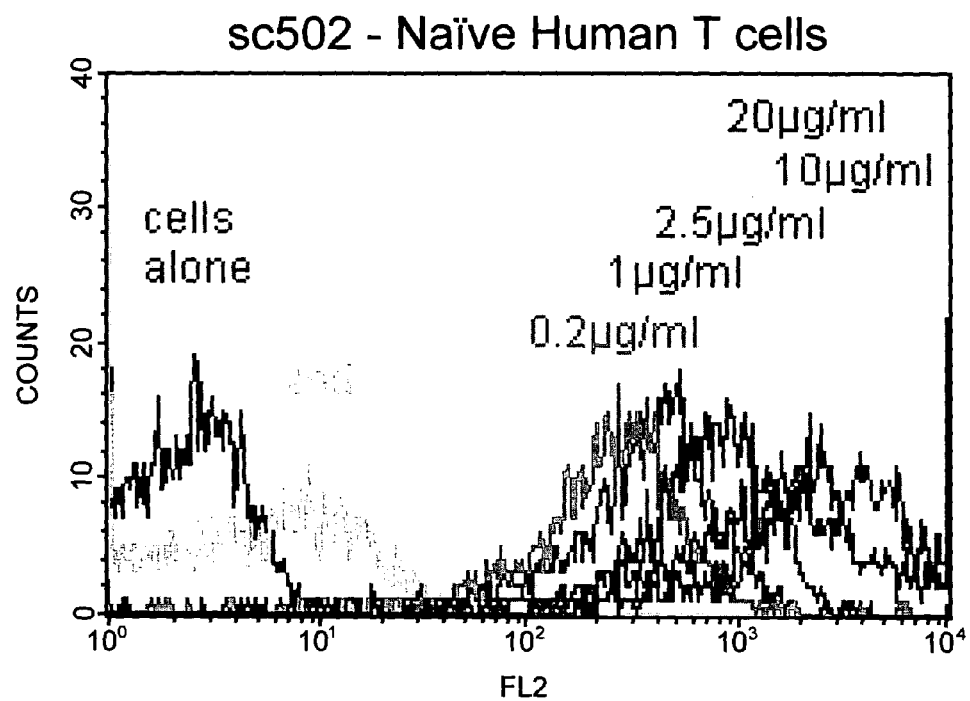
FIG. 9A2
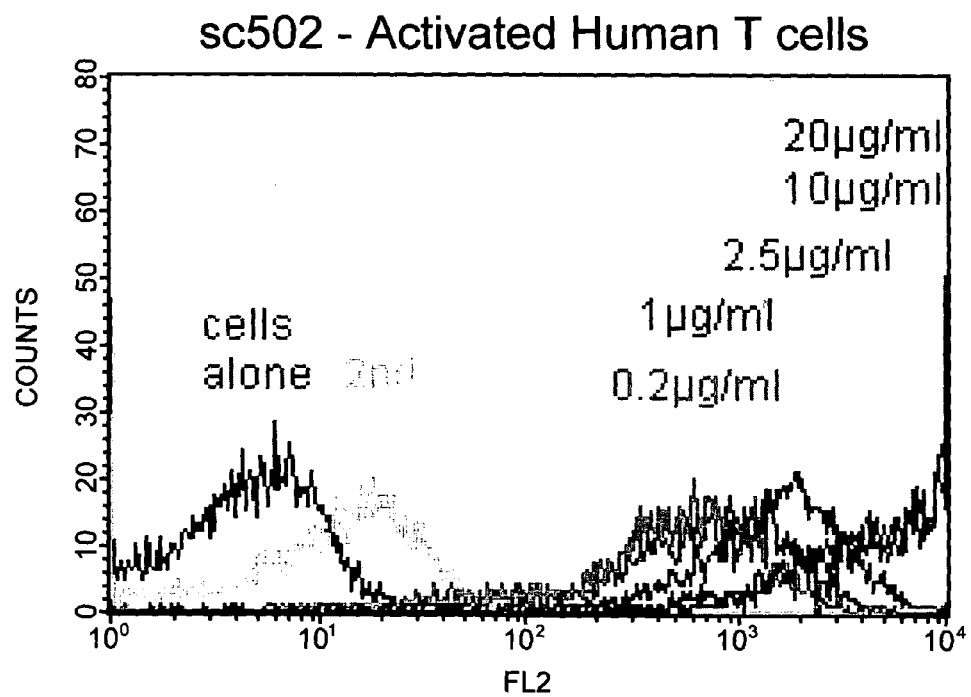

FIG. 9B1
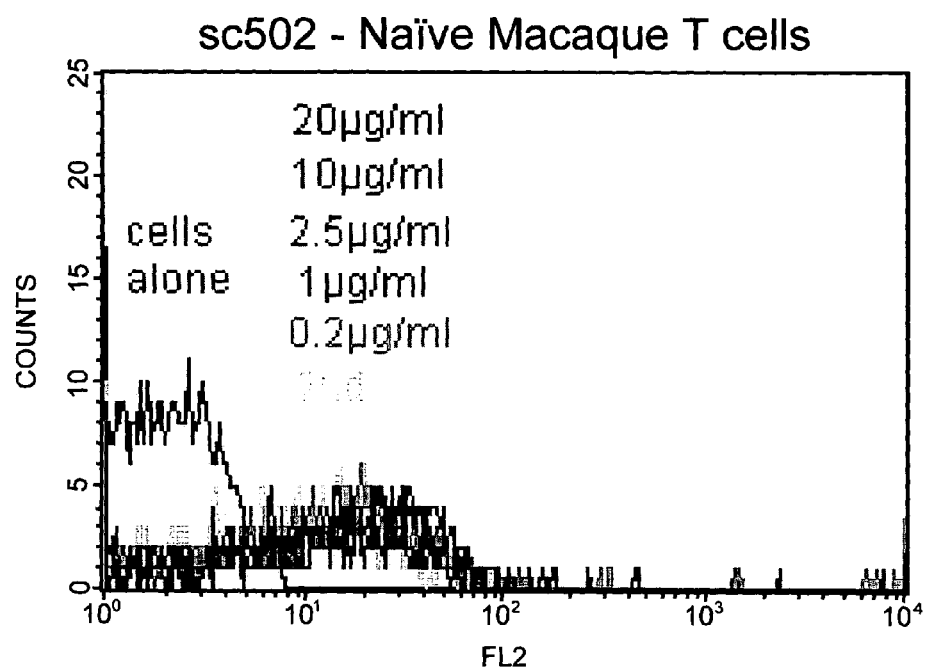
FIG. 9B2
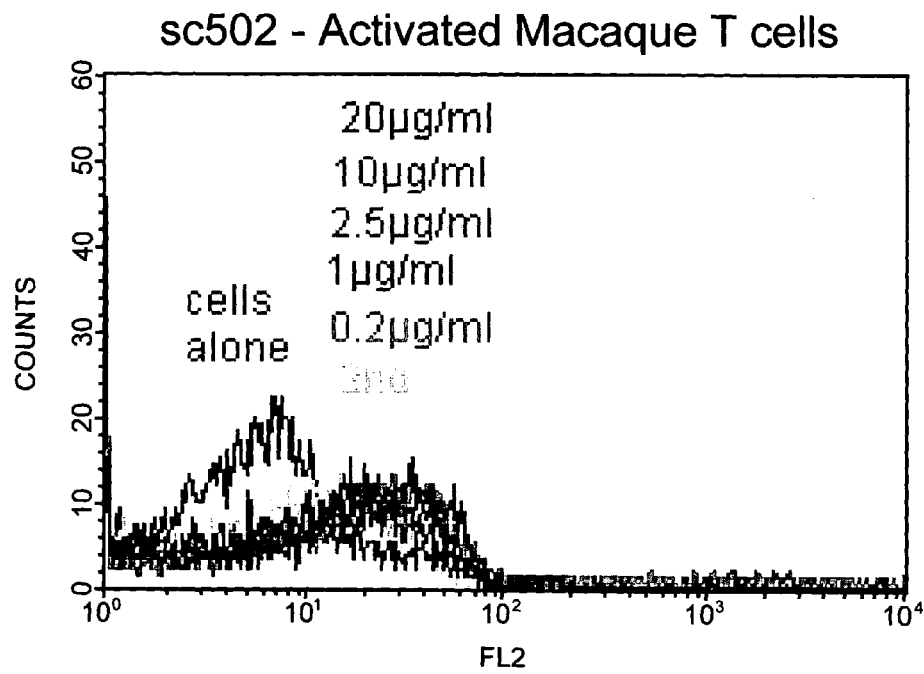

FIG. 10A1
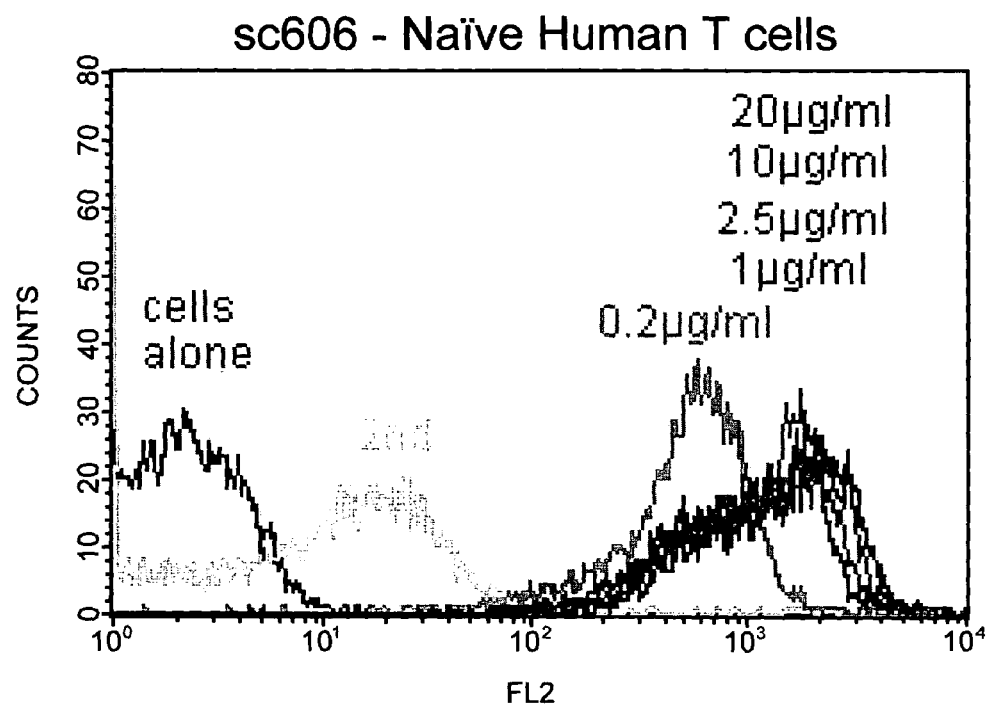
FIG. 10A2
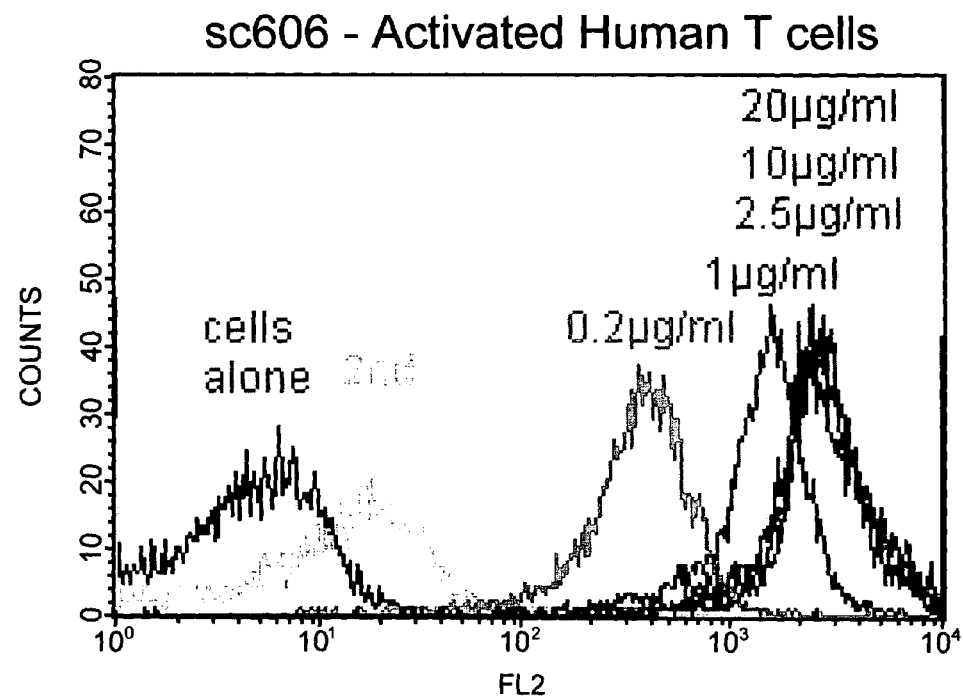

FIG. 10B1
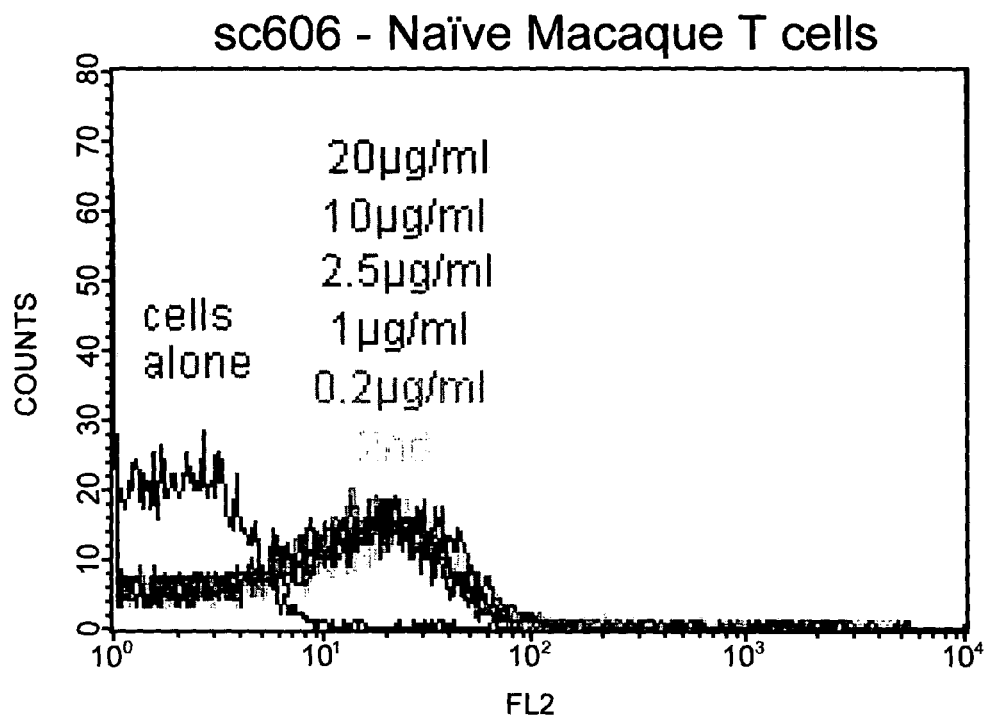
FIG. 10B2
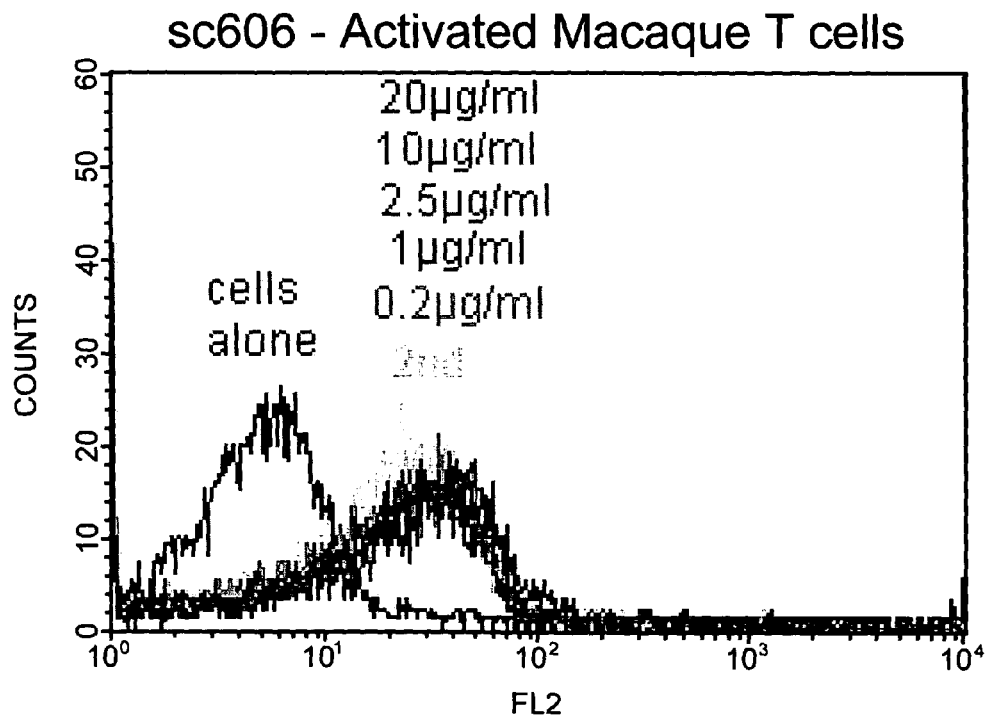

FIG. 11A1
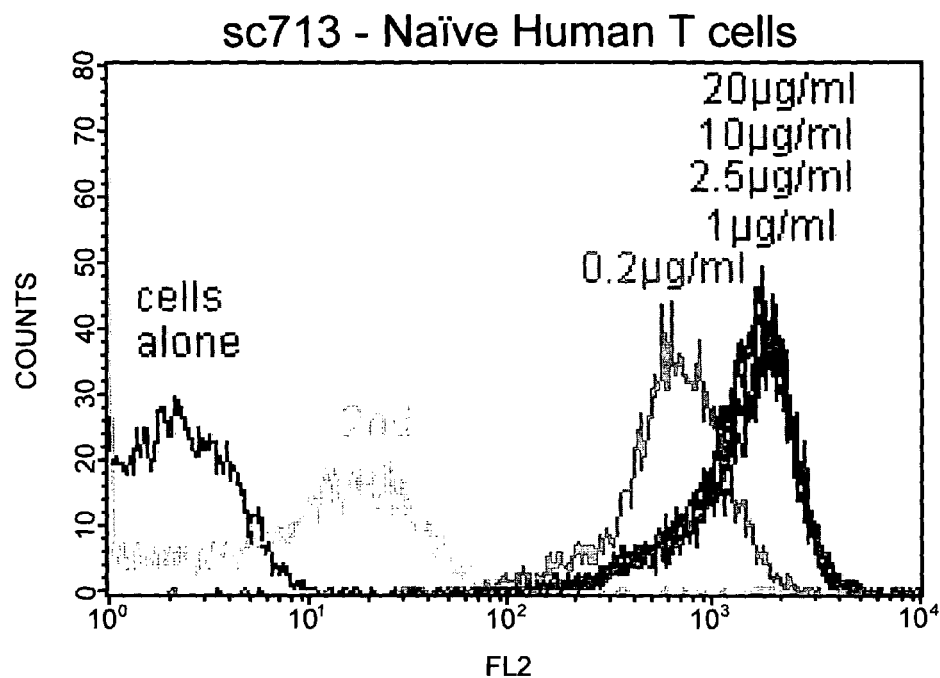
FIG. 11A2
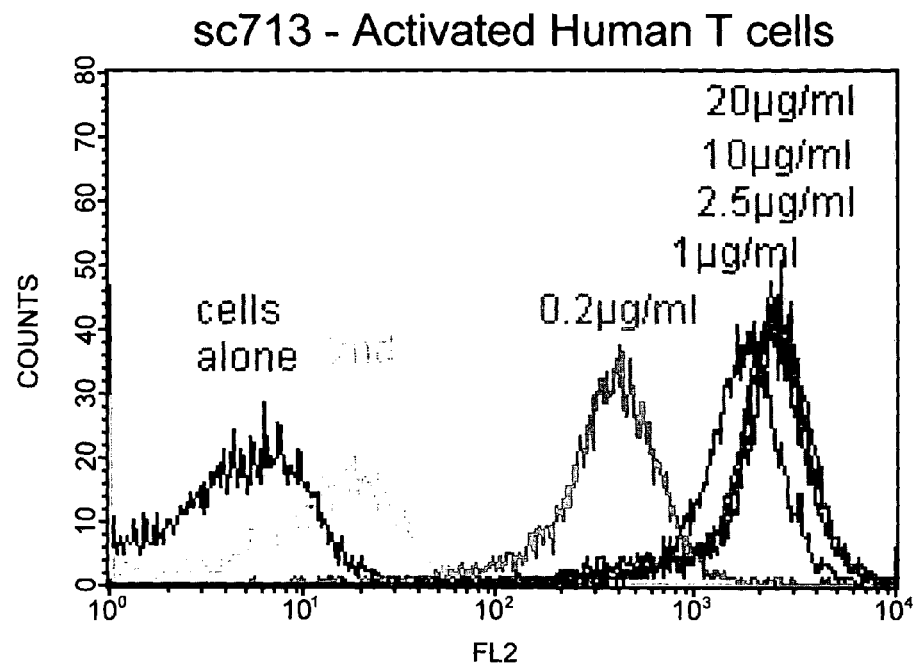

FIG. 11B1
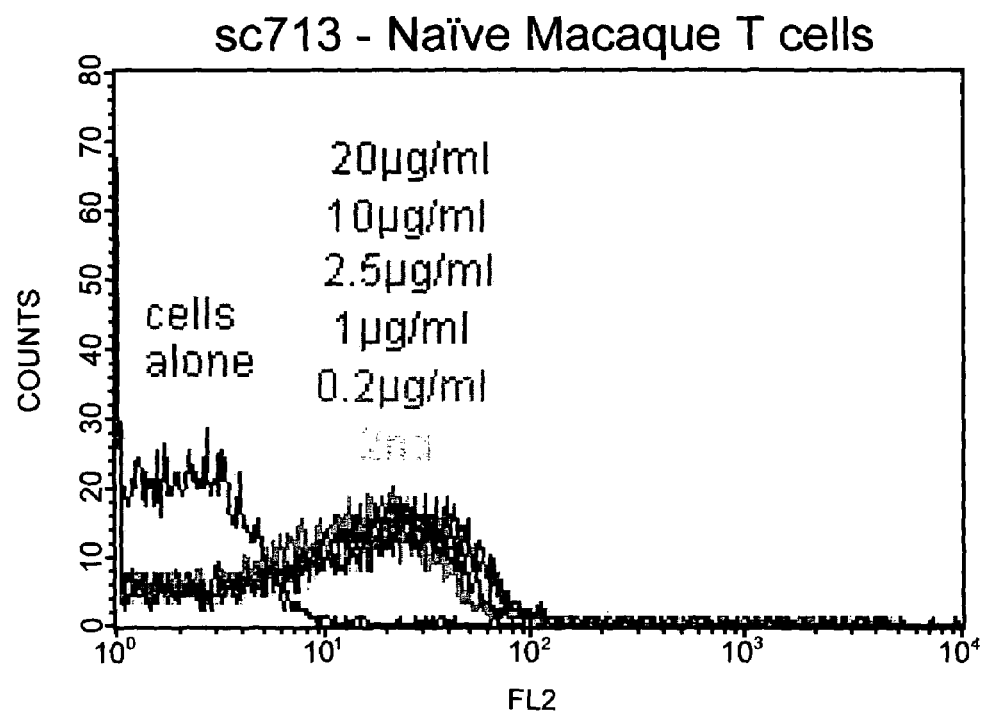
FIG. 11B2
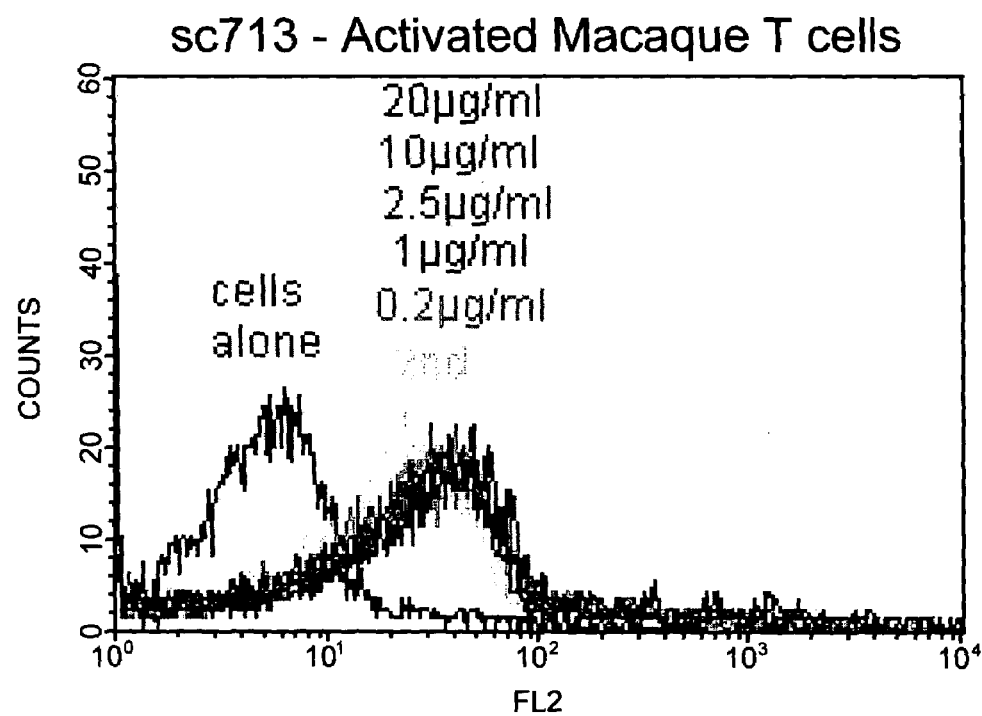

FIG. 12A1
Bin 2: Human T cell-specific - No Peptide Binding
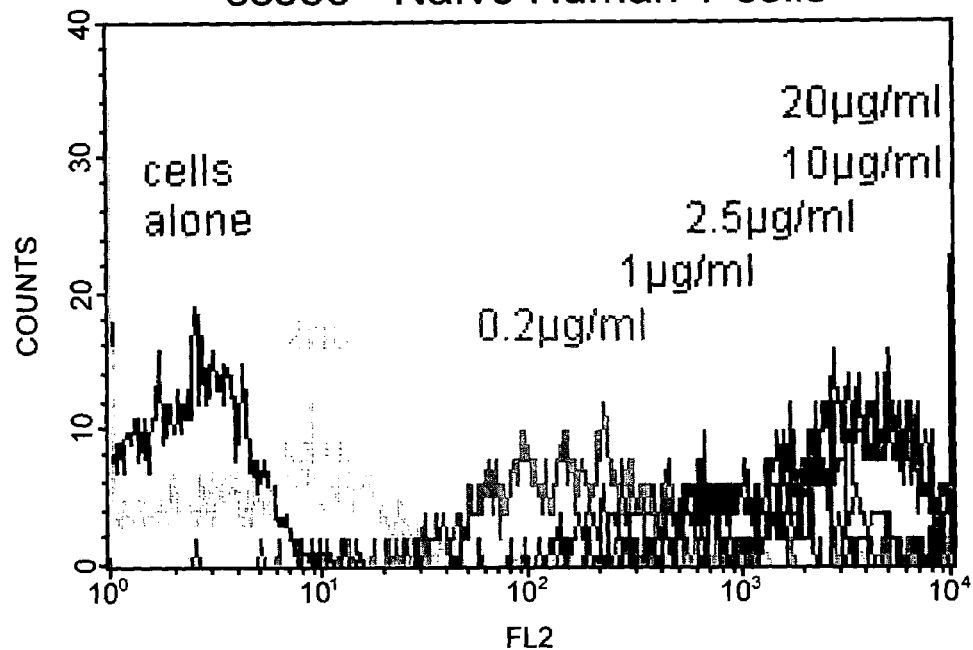
FIG. 12A2
Bin 2: Human T cell-specific - No Peptide Binding
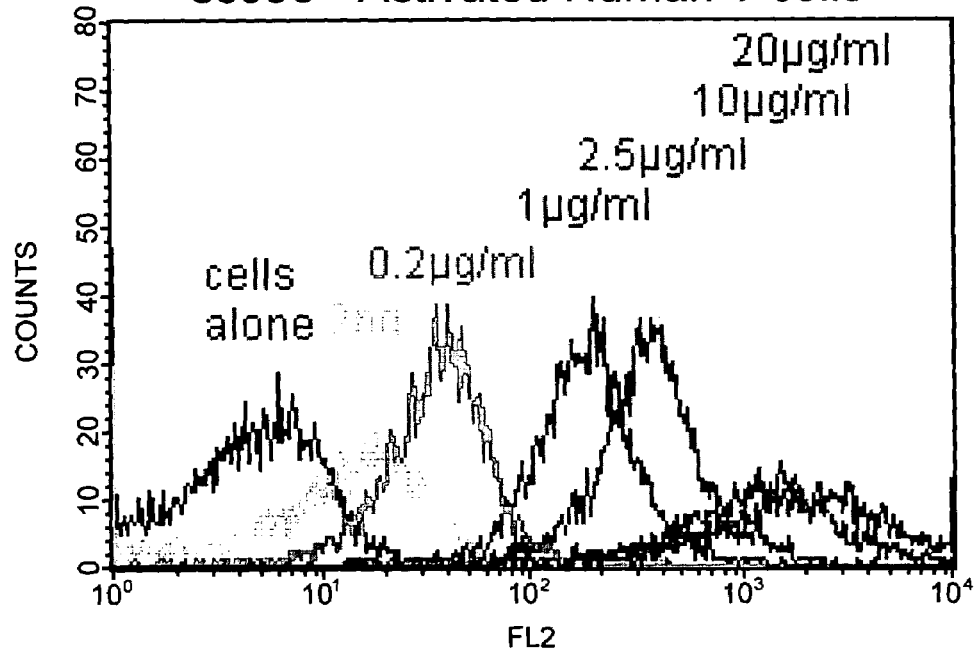

FIG. 12B1
Bin 2: Human T cell-specific - No Peptide Binding
sc636 - Naïve Macaque T cells
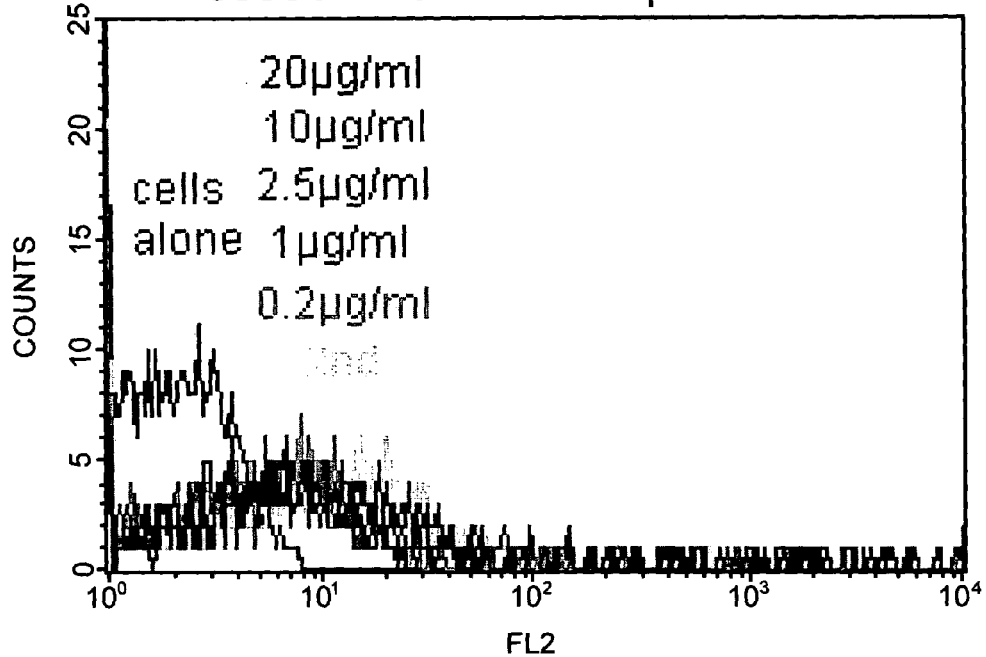
FIG. 12B2
Bin 2: Human T cell-specific - No Peptide Binding
sc636 - Activated Macaque T cells
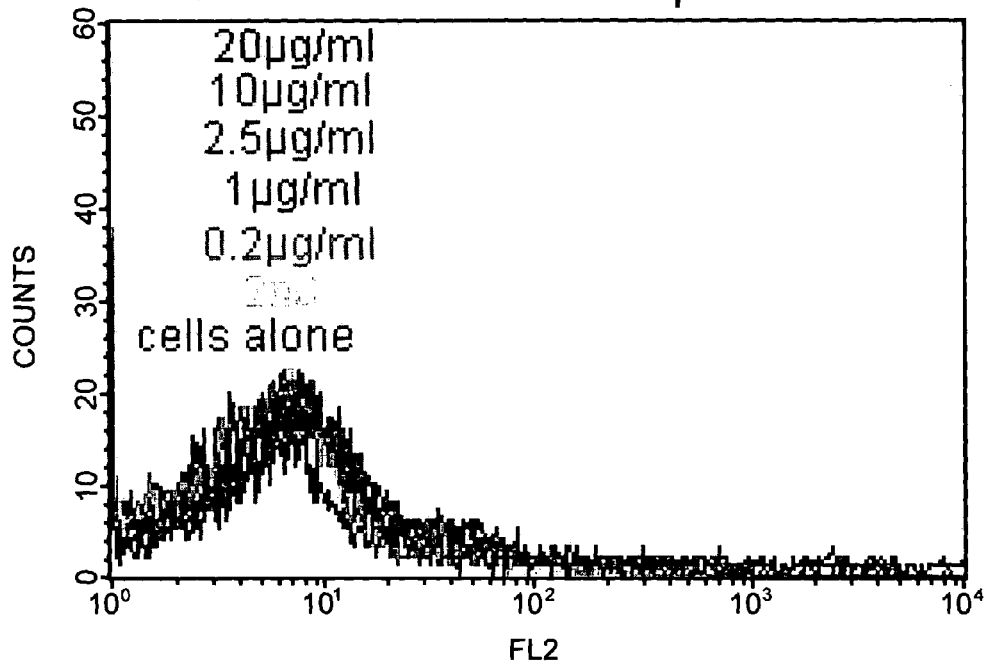

FIG. 13A1
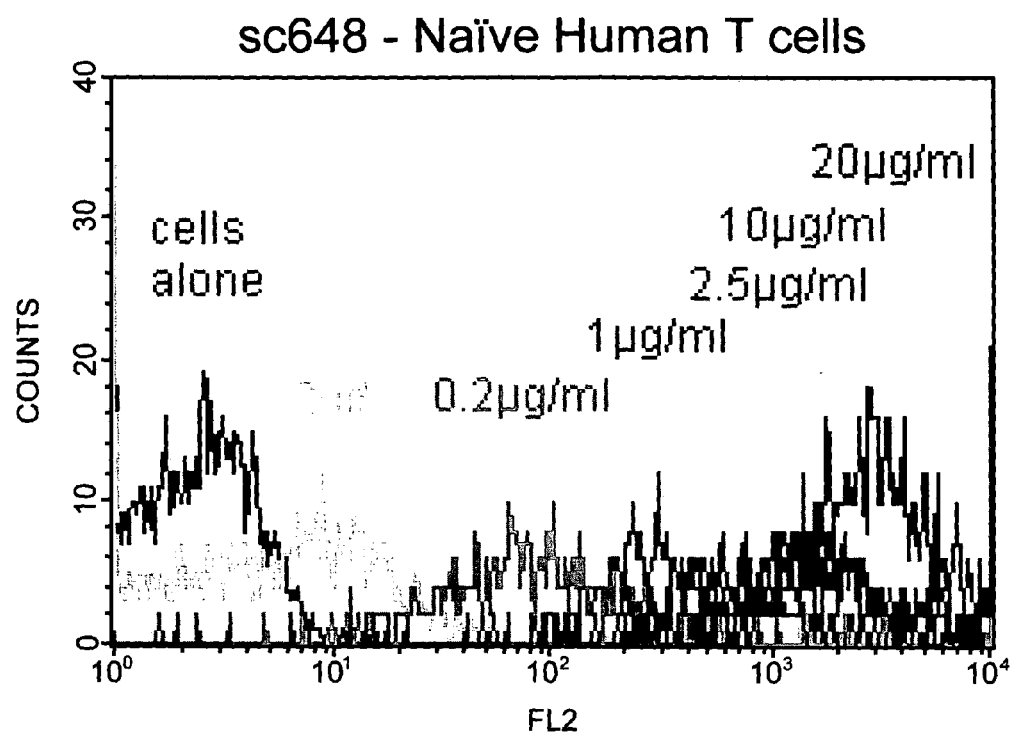
FIG. 13A2
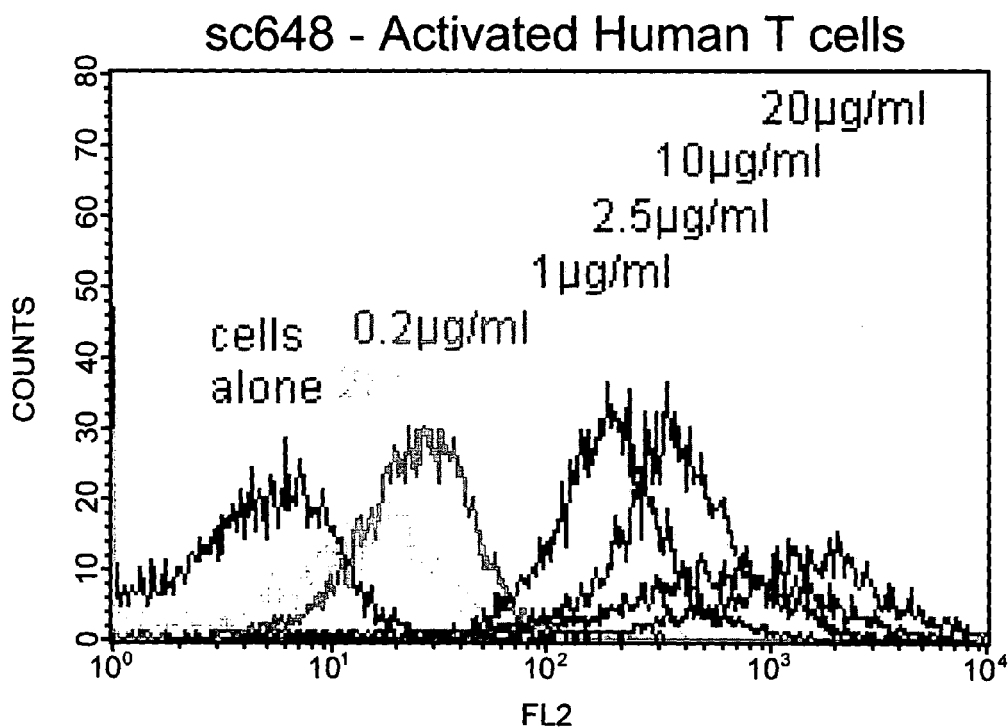

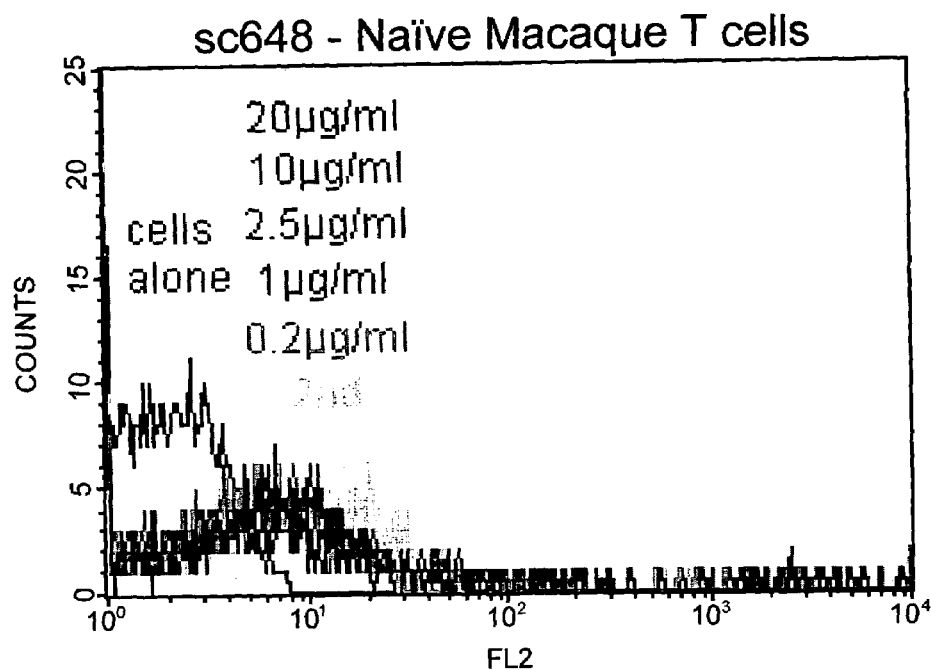
FIG. 13B1
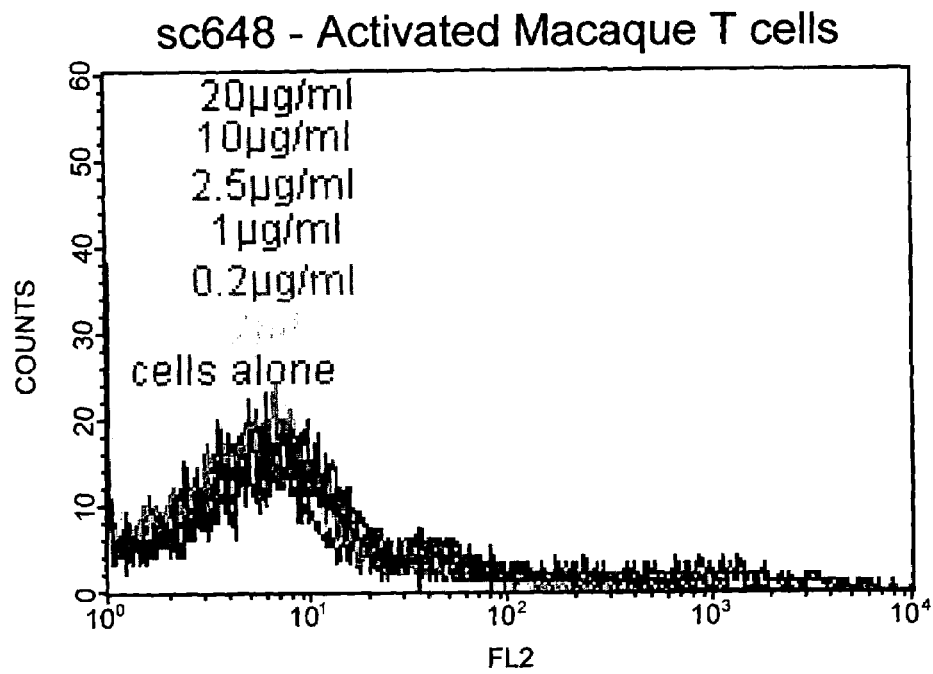
FIG. 13B2

FIG. 14A1
Bin 3: Binding to Human and Macaque CD45RB:
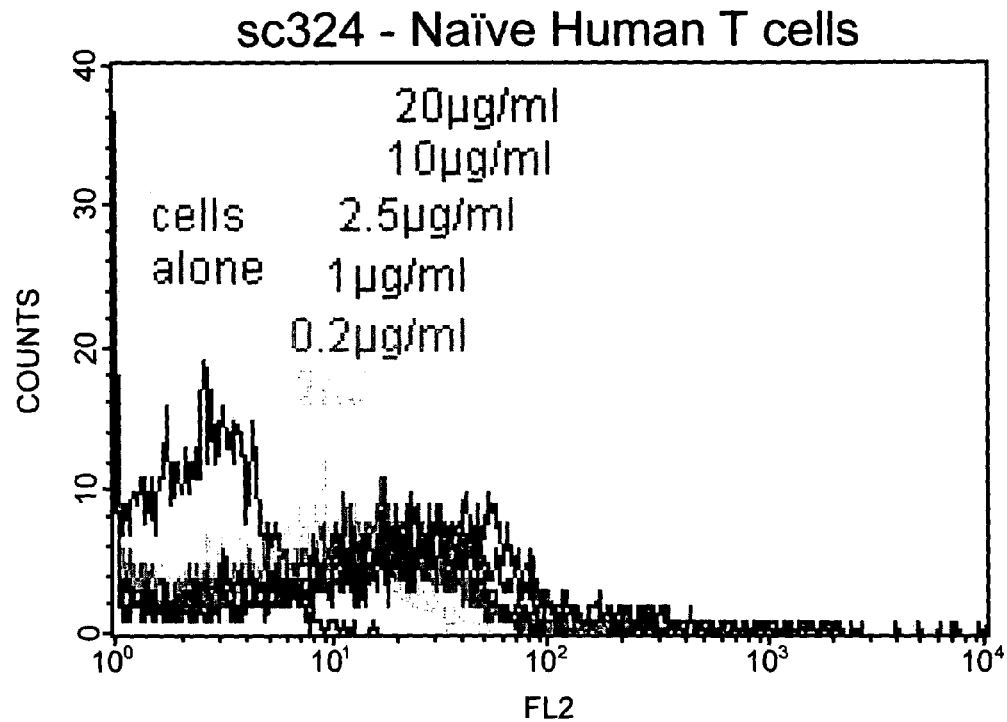
FIG. 14A2
Bin 3: Binding to Human and Macaque CD45RB:
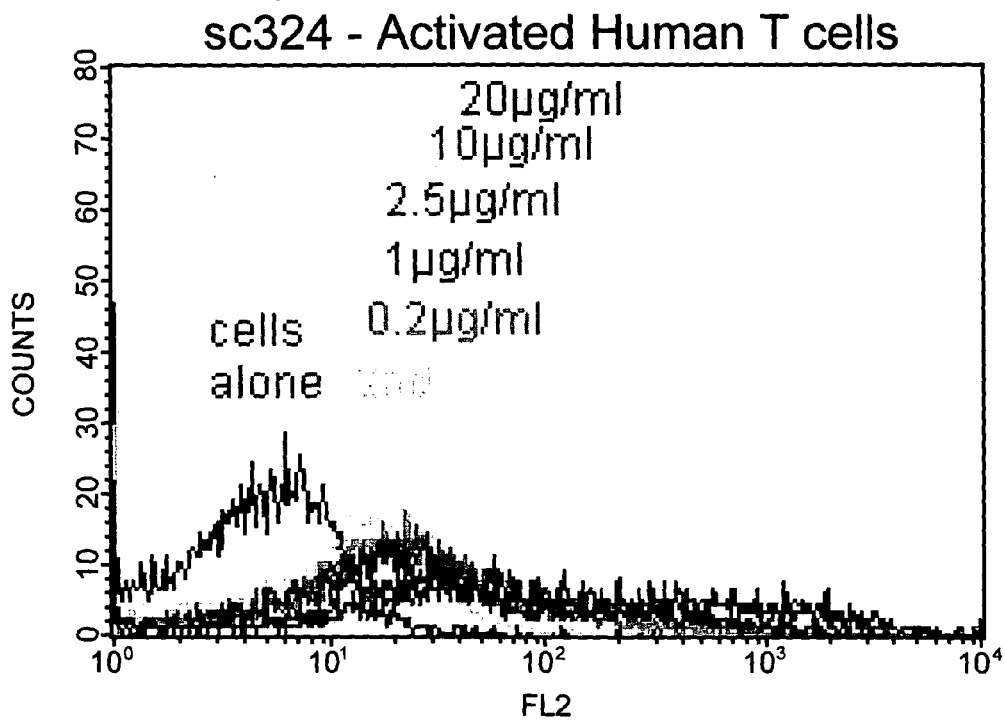

FIG. 14B1
Bin 3: Binding to Human and Macaque CD45RB:
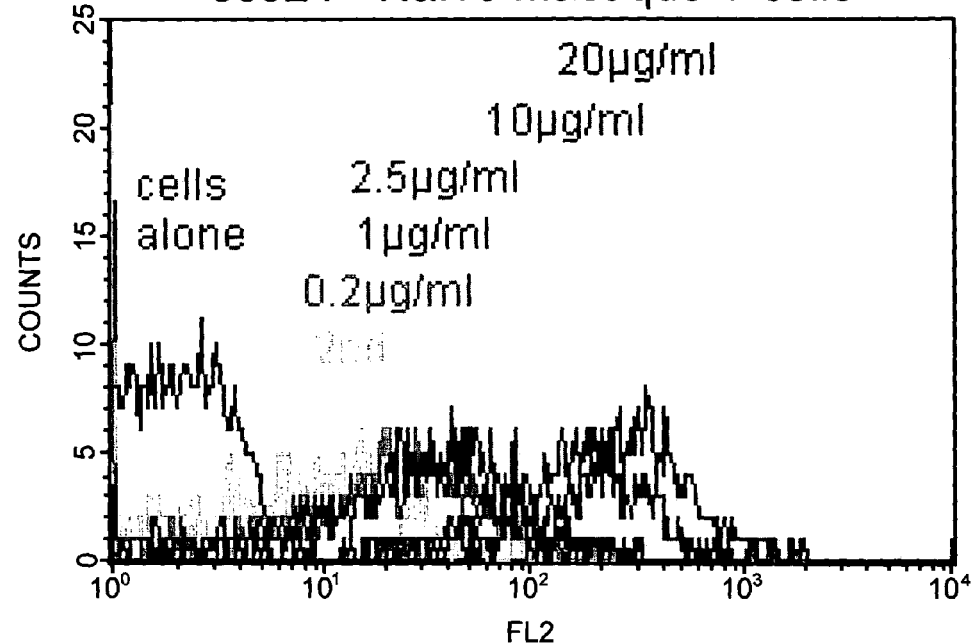
sc324 - Naïve Macaque T cells
FIG. 14B2
Bin 3: Binding to Human and Macaque CD45RB:
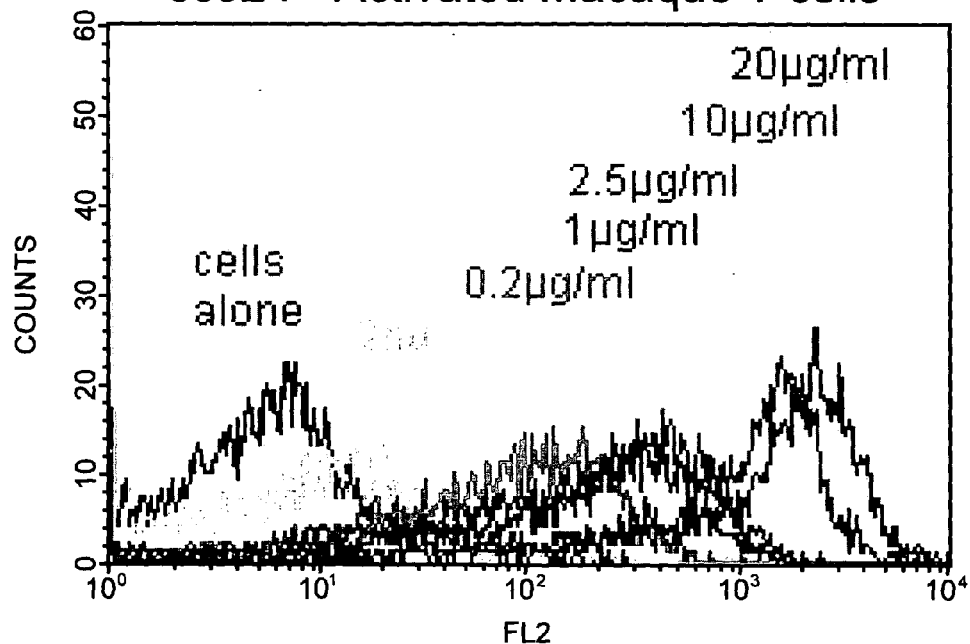
sc324 - Activated Macaque T cells FIG. 15A1
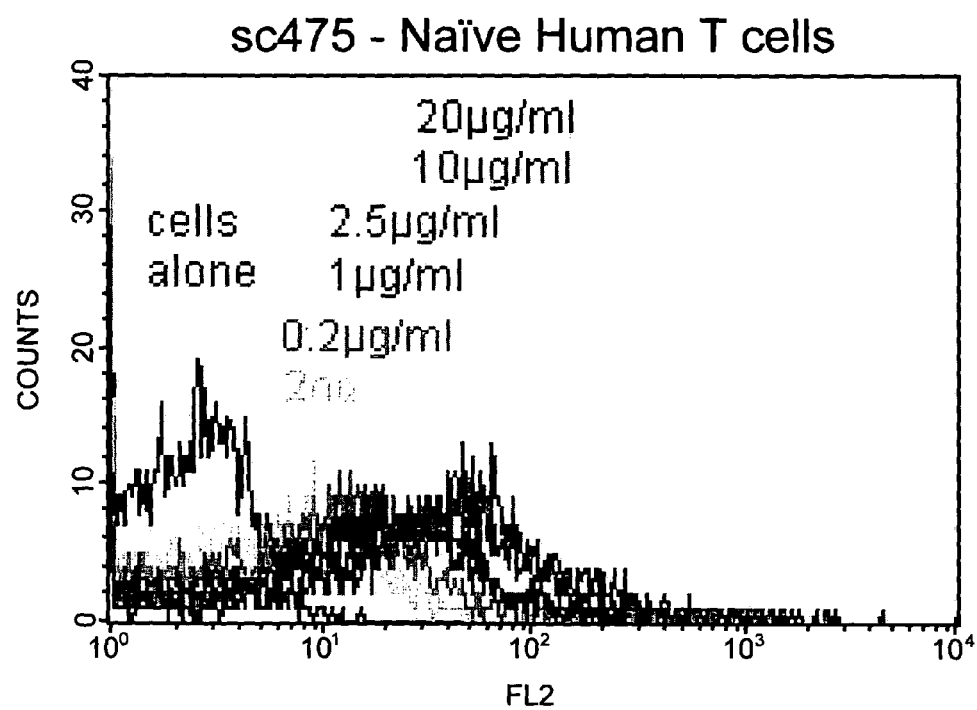
FIG. 15A2
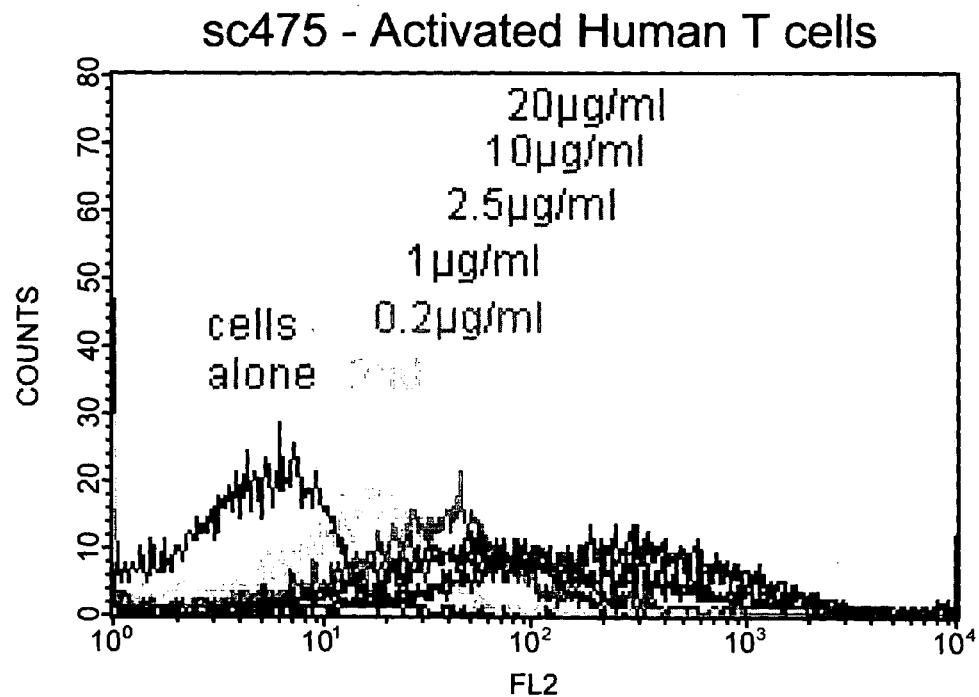

FIG. 15B1
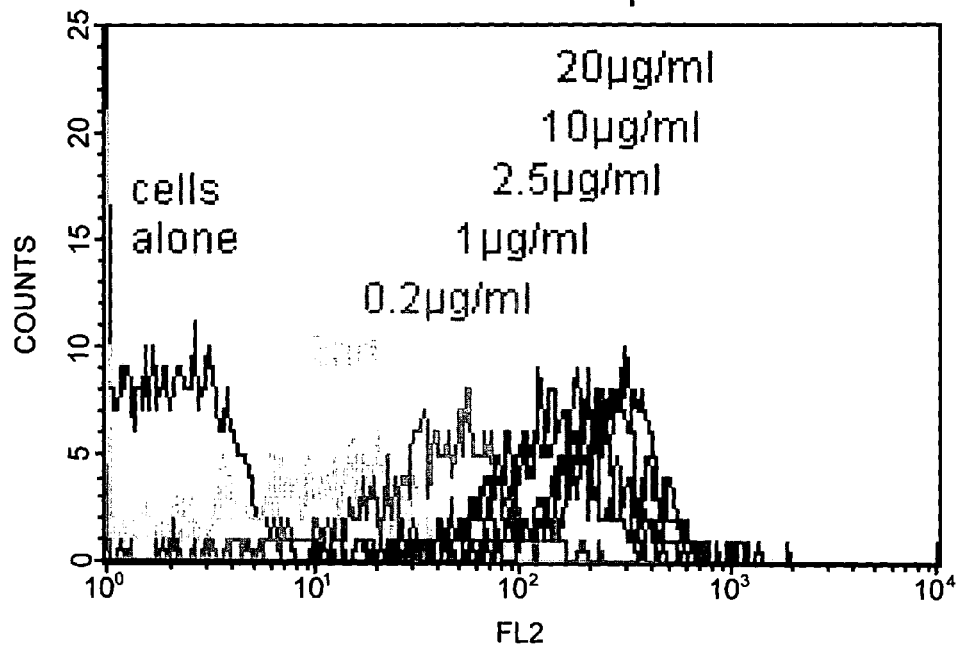
FIG. 15B2
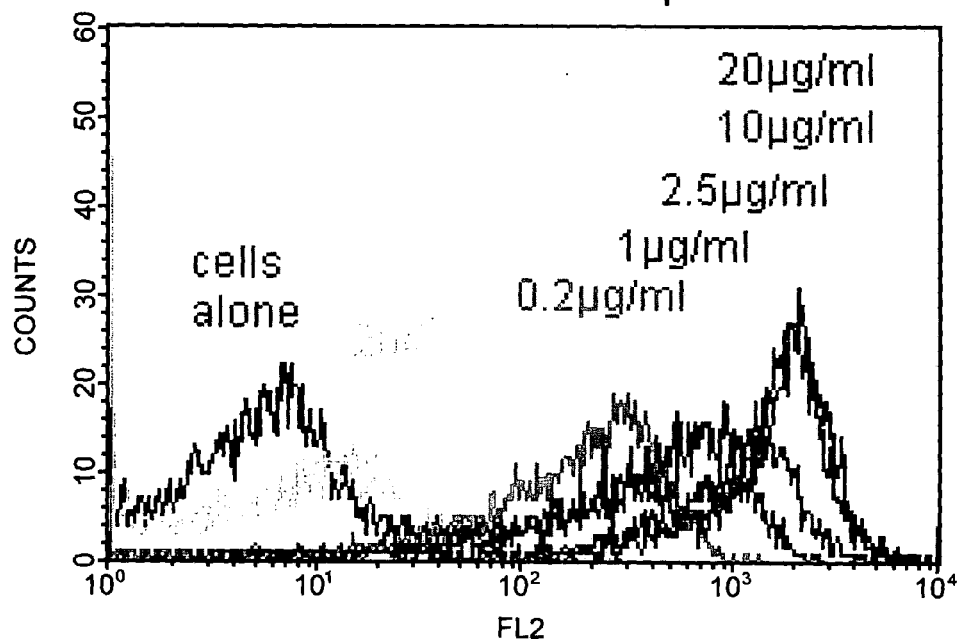

FIG. 16A1
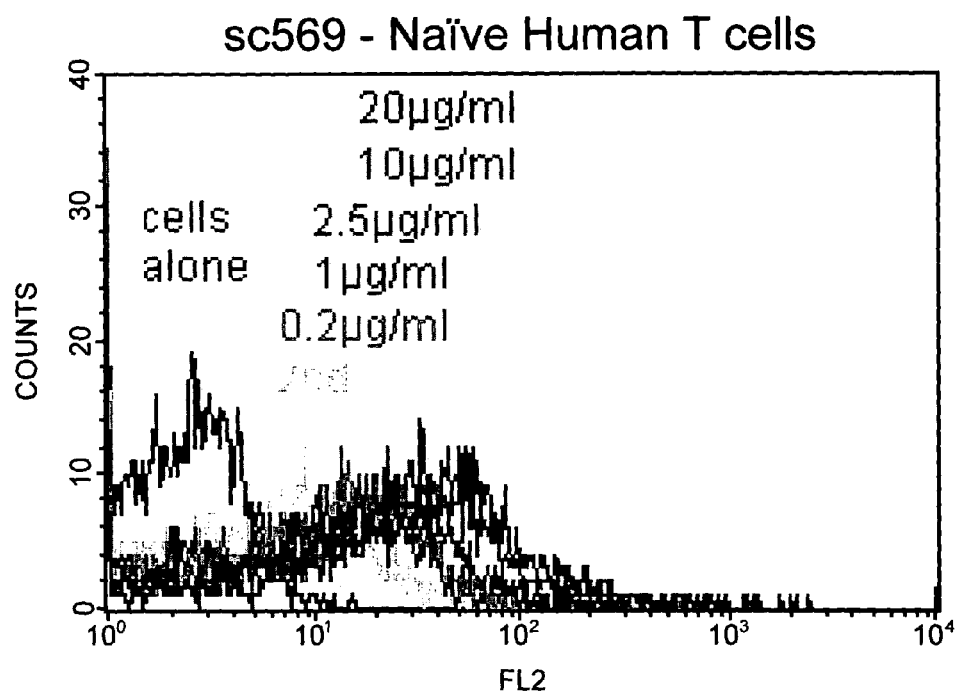
FIG. 16A2
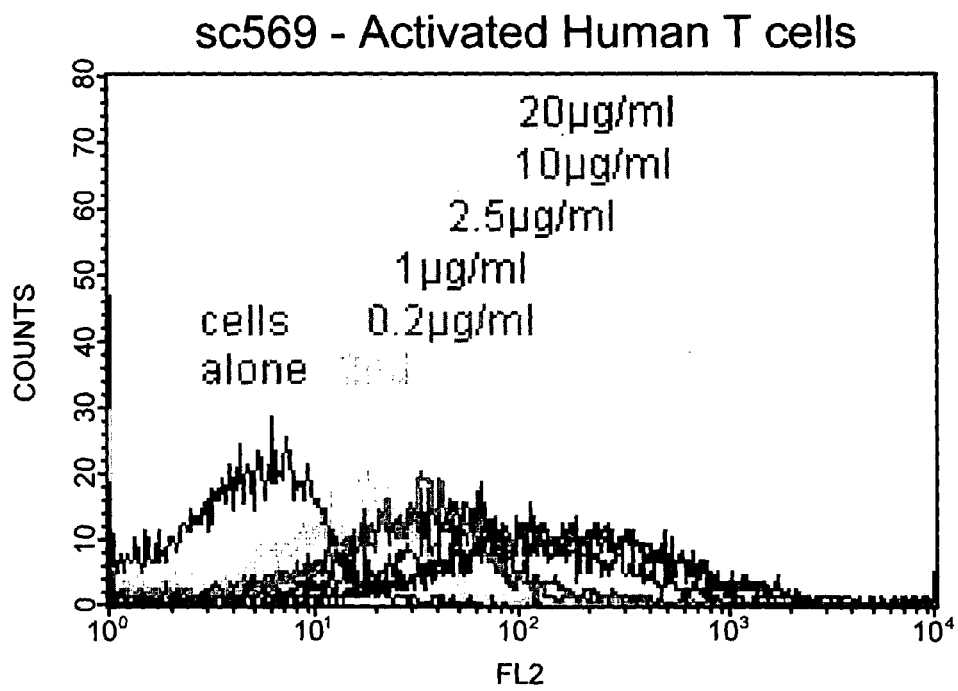

FIG. 16B1
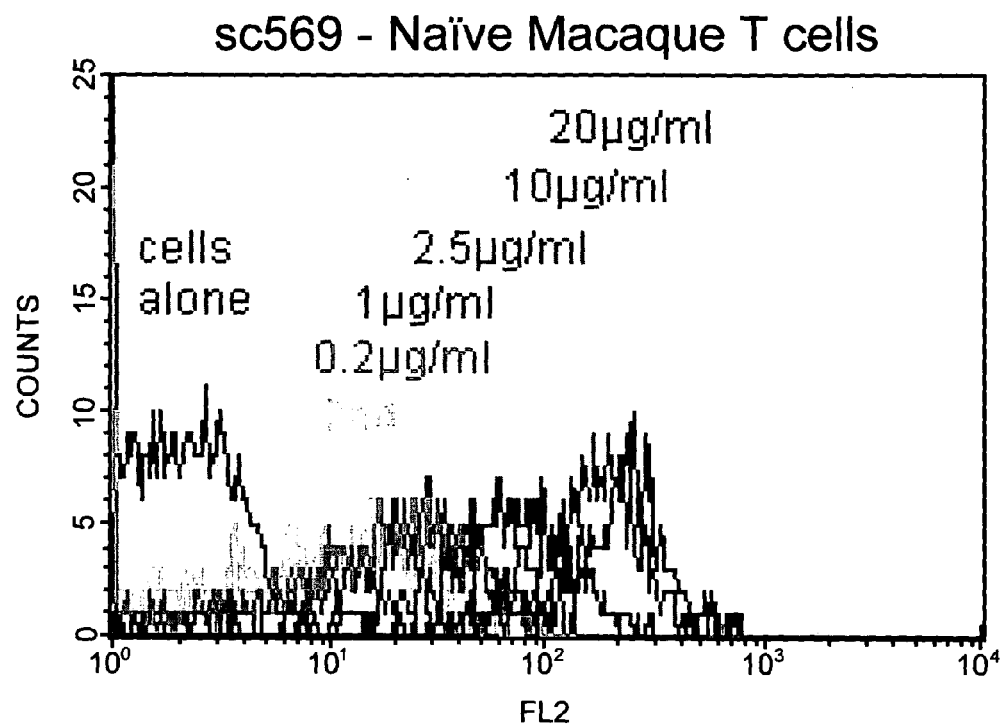
FIG. 16B2
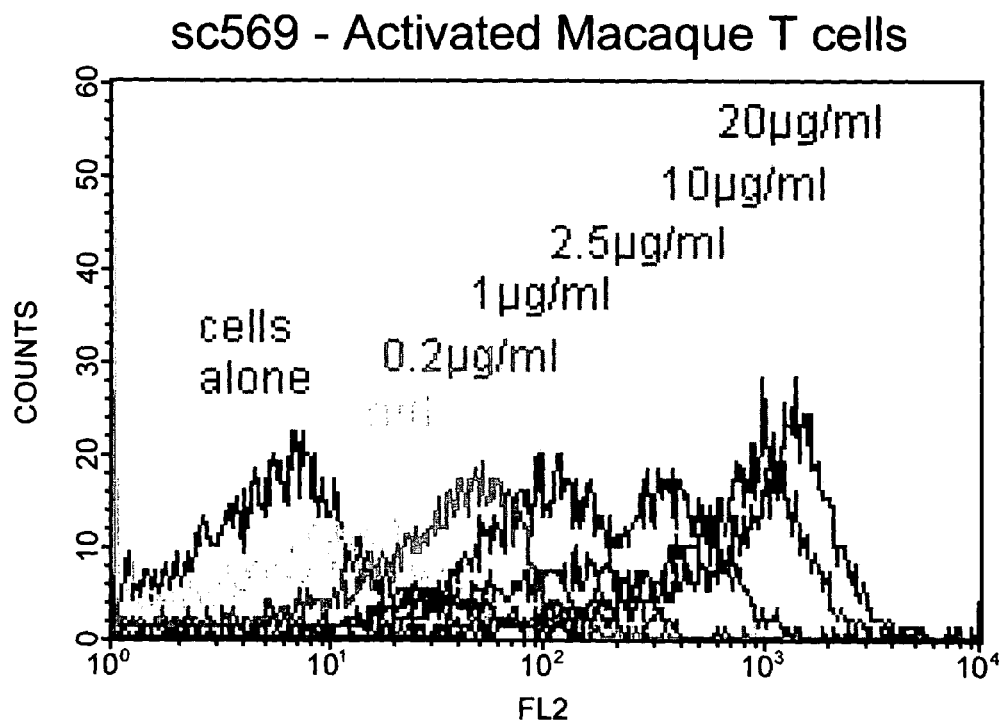

Down-regulation of L-Selectin on Human
Peripheral Blood Mononuclear Cells:

Down-regulation of L-Selectin on Human
Peripheral Blood Mononuclear Cells:

Down-regulation of L-Selectin on Human Peripheral Blood Mononuclear Cells:

Down-regulation of L-Selectin on Human Peripheral Blood Mononuclear Cells:

SEQUENCE LISTING

```
<160> NUMBER OF SEQ ID NOS: 147

<210> SEQ ID NO 1
<211> LENGTH: 109
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 2
<211> LENGTH: 113
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45
```

```
Ala Val Ile Trp Tyr Asp Gly Ser Lys Arg Phe Tyr Ala Gly Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Thr Asp Tyr Trp Gly Gln Gly Thr Met Val Thr Val Ser
            100                 105                 110

Ser

<210> SEQ ID NO 3
<211> LENGTH: 116
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Gly Asp Phe Asp Tyr Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Homo sapiens

<400> SEQUENCE: 4

Gln Val Gln Leu Val Glu Ser Gly Gly Gly Val Val Gln Pro Gly Lys
  1               5                  10                  15

Ser Leu Arg Leu Ser Cys Ala Ala Ser Gly Phe Thr Phe Arg Asn Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Lys Lys Phe Tyr Ala Asp Ser Val
    50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Val Tyr Tyr Cys
                 85                  90                  95

Val Arg Gly Gly Gly Asp Phe Asp Tyr Trp Gly Gln Gly Thr Leu Val
            100                 105                 110

Thr Val Ser Ser
        115
```

<210> SEQ ID NO 5
<211> LENGTH: 116
<212> TYPE: PRT
<213> ORGANISM: Homo sapiens

<400> SEQUENCE: 5

```
Gln Val Gln Leu Ala Glu Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Ile Ile Trp Tyr Asp Gly Ser Lys Lys Phe Tyr Ala Asp Ser Val
    50                  55                  60

Lys Gly Arg Phe Thr Ile Ser Arg Asp Asn Ser Asn Thr Leu Tyr
65                  70                  75                  80

Leu His Val Asn Ser Leu Arg Val Glu Asp Thr Ala Val Tyr Tyr Cys
                85                  90                  95

Ala Arg Gly Gly Gly Asp Ile Asp Phe Trp Gly Gln Gly Thr Leu Val
            100                 105                 110

Thr Val Ser Ser
            115
```

<210> SEQ ID NO 6
<211> LENGTH: 116
<212> TYPE: PRT
<213> ORGANISM: Homo sapiens

<400> SEQUENCE: 6

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Phe Tyr Ala Asp Ser Val
    50                  55                  60

Lys Gly Arg Phe Thr Ile Ser Arg Asp Asn Phe Glu Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Asp Phe Asp Tyr Trp Gly Gln Gly Thr Leu Val
            100                 105                 110

Thr Val Ser Ser
            115
```

<210> SEQ ID NO 7
<211> LENGTH: 116
<212> TYPE: PRT
<213> ORGANISM: Homo sapiens

<400> SEQUENCE: 7

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Lys Phe
                20                  25                  30

Gly Met His Trp Val Arg Gln Ala Pro Asp Lys Gly Leu Glu Trp Val
            35                  40                  45
```

-continued

Ala Val Ile Trp Tyr Asp Gly Thr Tyr Lys Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Gly Ser Phe Asp Tyr Trp Gly Gln Gly Thr Leu Val
             100                 105                 110

Thr Val Ser Ser
        115

<210> SEQ ID NO 8
<211> LENGTH: 116
<212> TYPE: PRT
<213> ORGANISM: Homo sapiens

<400> SEQUENCE: 8

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Lys Phe
             20                  25                  30

Gly Met His Trp Val Arg Gln Ala Pro Asp Lys Gly Leu Glu Trp Val
         35                  40                  45

Ala Val Ile Trp Tyr Asp Gly Ser Tyr Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ala Tyr Tyr Cys
                 85                  90                  95

Ala Arg Gly Gly Gly Ser Phe Asp Tyr Trp Gly Gln Gly Thr Leu Val
             100                 105                 110

Thr Val Ser Ser
        115

<210> SEQ ID NO 9
<211> LENGTH: 116
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Asp Lys Gly Leu Glu Trp Val
         35                  40                  45

Ala Val Ile Trp Tyr Asp Gly Ser Tyr Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Gly Ser Phe Asp Tyr Trp Gly Gln Gly Thr Leu Val
             100                 105                 110

Thr Val Ser Ser
        115

<210> SEQ ID NO 10
<211> LENGTH: 116
<212> TYPE: PRT
<213> ORGANISM: Homo sapiens

<400> SEQUENCE: 10

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Arg Gly Gly Gly Ser Phe Asp Tyr Trp Gly Gln Gly Thr Leu Val
            100                 105                 110

Thr Val Ser Ser
        115

<210> SEQ ID NO 11
<211> LENGTH: 116
<212> TYPE: PRT
<213> ORGANISM: Homo sapiens

<400> SEQUENCE: 11

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Phe Tyr Ala Asp Ser Val
    50                  55                  60

Lys Gly Arg Phe Thr Ile Ser Arg Asp Asn Ser Lys Asn Met Gln Tyr
65                  70                  75                  80

Leu Gln Met Asp Ser Leu Arg Ala Glu Asp Thr Ala Val Tyr Tyr Cys
                85                  90                  95

Ala Arg Gly Gly Gly Asp Phe Asp Tyr Trp Gly Gln Gly Ile Leu Val
            100                 105                 110

Thr Val Ser Ser
        115

<210> SEQ ID NO 12
<211> LENGTH: 116
<212> TYPE: PRT
<213> ORGANISM: Homo sapiens

<400> SEQUENCE: 12

Gln Val Gln Leu Val Glu Ser Gly Gly Val Val Gln Pro Gly Arg
1               5                   10                  15

Ser Leu Arg Val Ser Cys Glu Ala Ser Gly Phe Thr Phe Ser Asn Tyr
            20                  25                  30

```
Gly Met His Trp Val Arg Gln Ala Pro Gly Lys Gly Leu Glu Trp Val
        35                  40                  45

Ala Val Ile Trp Tyr Asp Gly Ser Lys Lys Phe Tyr Ala Asp Ser Val
 50                  55                  60

Lys Gly Arg Phe Thr Ile Ser Arg Asp Asn Ser Gln Asn Thr Leu Ser
65                  70                  75                  80

Leu Gln Met Ser Ser Leu Arg Ala Glu Asp Thr Ala Val Tyr Tyr Cys
                85                  90                  95

Ala Arg Gly Gly Gly Asp Phe Asp Phe Trp Gly Gln Gly Thr Leu Val
            100                 105                 110

Thr Val Ser Ser
        115

<210> SEQ ID NO 13
<211> LENGTH: 116
<212> TYPE: PRT
<213> ORGANISM: Homo sapiens

<400> SEQUENCE: 13

Gln Val Gln Leu Val Glu Ser Gly Gly Gly Val Val Gln Pro Gly Arg
 1               5                  10                  15

Ser Leu Arg Val Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Phe Tyr Ala Asp Ser Val
 50                  55                  60

Lys Gly Arg Phe Thr Ile Ser Arg Asp Asn Ser Gln Asn Thr Leu Ser
65                  70                  75                  80

Leu Gln Met Ser Ser Leu Arg Ala Glu Asp Thr Ala Val Tyr Tyr Cys
                85                  90                  95

Ala Arg Gly Gly Gly Asp Phe Asp Phe Trp Gly Gln Gly Thr Leu Val
            100                 105                 110

Thr Val Ser Ser
        115

<210> SEQ ID NO 14
<211> LENGTH: 116
<212> TYPE: PRT
<213> ORGANISM: Homo sapiens

<400> SEQUENCE: 14

Gln Val Gln Leu Val Glu Ser Gly Gly Gly Val Val Gln Pro Gly Arg
 1               5                  10                  15

Ser Leu Arg Val Ser Cys Ala Ala Ser Gly Phe Thr Phe Ser Asn Tyr
                20                  25                  30

Gly Met His Trp Val Arg Gln Ala Pro Asp Lys Gly Leu Glu Trp Val
        35                  40                  45

Ala Val Ile Trp Tyr Asp Gly Ser Lys Lys Phe Tyr Ala Asp Ser Val
 50                  55                  60

Lys Gly Arg Phe Thr Ile Ser Arg Asp Asn Ser Gln Asn Thr Leu Ser
65                  70                  75                  80

Leu Gln Met Ser Ser Leu Arg Ala Glu Asp Thr Ala Val Tyr Tyr Cys
                85                  90                  95

Ala Arg Gly Gly Gly Asp Phe Asp Phe Trp Gly Gln Gly Thr Leu Val
            100                 105                 110
```

Thr Val Ser Ser
        115

<210> SEQ ID NO 15
<211> LENGTH: 116
<212> TYPE: PRT
<213> ORGANISM: Homo sapiens

<400> SEQUENCE: 15

Gln Val Gln Leu Val Glu Ser Gly Gly Gly Val Val Gln Pro Gly Arg
1               5                   10                  15

Ser Leu Arg Val Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Phe Tyr Ala Asp Ser Val
    50                  55                  60

Lys Gly Arg Phe Thr Ile Ser Arg Asp Asn Ser Gln Asn Thr Leu Ser
65                  70                  75                  80

Leu Gln Met Ser Ser Leu Arg Ala Glu Asp Thr Ala Val Tyr Tyr Cys
                85                  90                  95

Ala Arg Gly Gly Gly Asp Phe Asp Phe Trp Gly Gln Gly Thr Leu Val
            100                 105                 110

Thr Val Ser Ser
        115

<210> SEQ ID NO 16
<211> LENGTH: 116
<212> TYPE: PRT
<213> ORGANISM: Homo sapiens

<400> SEQUENCE: 16

Gln Val Gln Leu Val Glu Ser Gly Gly Gly Val Val Gln Pro Gly Arg
1               5                   10                  15

Ser Leu Arg Val Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Phe Tyr Ala Asp Ser Val
    50                  55                  60

Lys Gly Arg Phe Thr Ile Ser Arg Asp Asn Ser Gln Asn Thr Leu Ser
65                  70                  75                  80

Leu Gln Met Ser Ser Leu Arg Ala Glu Asp Thr Ala Val Tyr Tyr Cys
                85                  90                  95

Ala Arg Gly Gly Gly Asp Phe Asp Phe Trp Gly Gln Gly Thr Leu Val
            100                 105                 110

Thr Val Ser Ser
        115

<210> SEQ ID NO 17
<211> LENGTH: 109
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                20                  25                  30
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105

<210> SEQ ID NO 18
<211> LENGTH: 119
<212> TYPE: PRT
<213> ORGANISM: Homo sapiens

<400> SEQUENCE: 18

Ala Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Phe Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Glu Val Met Gly Pro Ile Phe Phe Asp Tyr Trp Gly Gln Gly
            100                 105                 110

Thr Leu Val Thr Val Ser Ser
        115

<210> SEQ ID NO 19
<211> LENGTH: 108
<212> TYPE: PRT
<213> ORGANISM: Homo sapiens

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gln Gly Thr Leu Val Thr Val Ser Ser
            100                 105
```

<210> SEQ ID NO 20
<211> LENGTH: 119
<212> TYPE: PRT
<213> ORGANISM: Homo sapiens

<400> SEQUENCE: 20

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Ser
            20                  25                  30

Tyr Trp Ser Trp Ile Arg Gln Pro Ala Gly Lys Gly Leu Glu Trp Ile
        35                  40                  45

Gly Arg Ile His Ser Thr Gly Lys Thr Ala Tyr Asn Pro Ser Leu Lys
    50                  55                  60

Ser Arg Val Ile Met Ser Leu Asp Thr Ser Lys Asn Leu Phe Ser Leu
65                  70                  75                  80

Lys Leu Thr Ser Val Thr Ala Ala Asp Thr Ala Val Tyr Tyr Cys Ala
                85                  90                  95

Arg Asp Tyr Asp Phe Leu Thr Gly Tyr Phe Asp Tyr Trp Gly Gln Gly
            100                 105                 110

Thr Leu Val Thr Val Ser Ser
        115
```

<210> SEQ ID NO 21
<211> LENGTH: 119
<212> TYPE: PRT
<213> ORGANISM: Homo sapiens

<400> SEQUENCE: 21

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Ala Gly Lys Gly Leu Glu Trp Ile
        35                  40                  45

Gly Arg Ile His Thr Thr Gly Lys Thr Ala Tyr Asn Pro Ser Leu Lys
    50                  55                  60

Ser Arg Val Ile Met Ser Val Asp Thr Ser Lys Asn Leu Phe Ser Leu
65                  70                  75                  80

Lys Leu Thr Ser Val Thr Ala Ala Asp Thr Ala Val Tyr Tyr Cys Ala
                85                  90                  95

Arg Asp Tyr Asp Phe Leu Thr Gly Tyr Phe Asp Tyr Trp Gly Gln Gly
            100                 105                 110

Thr Leu Val Thr Val Ser Ser
        115
```

<210> SEQ ID NO 22
<211> LENGTH: 119
<212> TYPE: PRT
<213> ORGANISM: Homo sapiens

<400> SEQUENCE: 22

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Ala Gly Lys Gly Leu Glu Trp Ile
```

```
                    35                  40                  45
Gly Arg Ile His Thr Thr Gly Lys Thr Ala Tyr Asn Ser Ser Leu Lys
    50                  55                  60

Ser Arg Val Ile Met Ser Val Asp Thr Ser Lys Asn Leu Phe Ser Leu
65                  70                  75                  80

Lys Leu Thr Ser Val Thr Ala Ala Asp Thr Ala Val Tyr Tyr Cys Ala
                85                  90                  95

Arg Asp Tyr Asp Phe Leu Thr Gly Tyr Phe Asp Tyr Trp Gly Gln Gly
            100                 105                 110

Thr Leu Val Thr Val Ser Ser
        115

<210> SEQ ID NO 23
<211> LENGTH: 109
<212> TYPE: PRT
<213> ORGANISM: Homo sapiens

<400> SEQUENCE: 23

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 24
<211> LENGTH: 119
<212> TYPE: PRT
<213> ORGANISM: Homo sapiens

<400> SEQUENCE: 24

Gln Val Gln Leu Val Glu Ser Gly Gly Asp Leu Val Lys Pro Gly Gly
1               5                   10                  15

Ser Leu Arg Leu Ser Cys Ala Ala Ser Gly Phe Ser Phe Ser Gly Tyr
            20                  25                  30

Tyr Leu Ser Trp Ile Arg Gln Ala Pro Gly Lys Gly Leu Glu Trp Val
        35                  40                  45

Ser Tyr Ile Ser Leu Ser Gly Ser Phe Ile Lys Tyr Ala Asp Ser Val
    50                  55                  60

Lys Gly Arg Phe Thr Ile Ser Arg Asp Asn Ala Lys Lys Thr Leu His
65                  70                  75                  80

Leu Gln Met Asn Ser Leu Arg Ala Glu Asp Thr Ala Val Tyr Tyr Cys
                85                  90                  95

Ala Arg Arg Thr Gly Thr Thr Val Phe Asp Tyr Trp Gly Gln Gly
            100                 105                 110

Thr Leu Val Thr Val Ser Ser
        115
```

<210> SEQ ID NO 25
<211> LENGTH: 119
<212> TYPE: PRT
<213> ORGANISM: Homo sapiens

<400> SEQUENCE: 25

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Val Tyr
            20                  25                  30

Tyr Met Asn Trp Ile Arg Gln Ala Pro Gly Lys Gly Leu Glu Trp Val
        35                  40                  45

Ser Tyr Ile Ser Thr Ser Ser Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Ser Thr Thr Val Phe Asp Tyr Trp Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Homo sapiens

<400> SEQUENCE: 26

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ile Asn Tyr
            20                  25                  30

Tyr Met Thr Trp Ile Arg Gln Ala Pro Gly Lys Gly Leu Glu Trp Val
        35                  40                  45

Ser Tyr Ile Ser Leu Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Arg Ala Ala Thr Val Thr Thr Phe Asp Tyr Trp Gly Gln Gly
            100                 105                 110

Thr Leu Val Thr Val Ser Ser
        115

<210> SEQ ID NO 27
<211> LENGTH: 103
<212> TYPE: PRT
<213> ORGANISM: Homo sapiens

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

```
Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Tyr Tyr Cys Phe Gly Gln
                85                  90                  95

Gly Thr Arg Leu Glu Ile Lys
                100

<210> SEQ ID NO 28
<211> LENGTH: 112
<212> TYPE: PRT
<213> ORGANISM: Homo sapiens

<400> SEQUENCE: 28

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Trp Cys Met Gln Ser
                85                  90                  95

Ile Gln Leu Pro Ile Thr Phe Gly Gln Gly Thr Arg Leu Glu Ile Lys
            100                 105                 110

<210> SEQ ID NO 29
<211> LENGTH: 112
<212> TYPE: PRT
<213> ORGANISM: Homo sapiens

<400> SEQUENCE: 29

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Phe Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Ile Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Phe Pro Ile Thr Phe Gly Gln Gly Thr Arg Leu Glu Ile Lys
            100                 105                 110

<210> SEQ ID NO 30
<211> LENGTH: 112
<212> TYPE: PRT
<213> ORGANISM: Homo sapiens

<400> SEQUENCE: 30
```

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Phe Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Ile Asp Phe Thr Leu Lys Ile
65              70                  75                  80

Ser Arg Val Glu Ala Glu Asp Val Gly Val Tyr Tyr Cys Met Gln Ser
                85                  90                  95

Ile Gln Phe Pro Ile Thr Phe Gly Gln Gly Thr Arg Leu Glu Ile Lys
            100                 105                 110

<210> SEQ ID NO 31
<211> LENGTH: 112
<212> TYPE: PRT
<213> ORGANISM: Homo sapiens

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Arg
            20                  25                  30

Asp Gly Lys Thr Phe Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ser
                85                  90                  95

Ile Gln Phe Pro Ile Thr Phe Gly Gln Gly Thr Arg Leu Glu Ile Lys
            100                 105                 110

<210> SEQ ID NO 32
<211> LENGTH: 112
<212> TYPE: PRT
<213> ORGANISM: Homo sapiens

<400> SEQUENCE: 32

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Phe Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Gly Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ser
                85                  90                  95

Ile Gln Phe Pro Ile Thr Phe Gly Gln Gly Thr Arg Leu Glu Ile Glu
            100                 105                 110

```
<210> SEQ ID NO 33
<211> LENGTH: 100
<212> TYPE: PRT
<213> ORGANISM: Homo sapiens

<400> SEQUENCE: 33

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Leu Thr Phe Gly Gly Gly Thr Lys
                85                  90                  95

Val Glu Ile Cys
            100

<210> SEQ ID NO 34
<211> LENGTH: 109
<212> TYPE: PRT
<213> ORGANISM: Homo sapiens

<400> SEQUENCE: 34

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Thr Ile Ser Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Thr Arg Ala Thr Gly Ile Pro Ala Arg Phe Ser
50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Asn Trp Pro
                85                  90                  95

Pro Leu Thr Thr Phe Gly Gly Gly Arg Lys Val Glu Ile
            100                 105

<210> SEQ ID NO 35
<211> LENGTH: 109
<212> TYPE: PRT
<213> ORGANISM: Homo sapiens

<400> SEQUENCE: 35

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Leu Ser Gly Lys
            20                  25                  30

Tyr Leu Ala Trp Tyr Gln Gln Lys Pro Gly Gln Ala Pro Ser Arg Leu
        35                  40                  45

Ile Tyr Gly Thr Ser Thr Arg Ala Thr Gly Val Pro Ala Arg Phe Ser
50                  55                  60

Gly Ser Gly Ser Gly Thr Glu Phe Thr Leu Thr Ile Ser Ser Leu Gln
```

-continued

```
                65                  70                  75                  80
        Ser Glu Asp Ser Ala Val Tyr Tyr Cys Gln Gln Tyr Asn Asn Trp Pro
                        85                  90                  95

Pro Leu Thr Thr Phe Gly Gly Gly Thr Lys Val Glu Ile
                        100                 105

<210> SEQ ID NO 36
<211> LENGTH: 109
<212> TYPE: PRT
<213> ORGANISM: Homo sapiens

<400> SEQUENCE: 36

Glu Ile Val Met Thr Gln Ser Pro Ala Thr Leu Ser Val Ser Leu Gly
1               5                   10                  15

Glu Arg Ala Thr Leu Ser Cys Arg Ala Ser Gln Asn Ile Ser Gly Asn
                20                  25                  30

Tyr Leu Ala Trp Tyr Gln Gln Arg Pro Gly Gln Ala Pro Arg Arg Leu
            35                  40                  45

Ile Tyr Ser Ala Ser Ser Arg Ala Thr Gly Ile Pro Asp Arg Phe Ser
        50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Asn Trp Pro
                85                  90                  95

Pro Leu Thr Thr Phe Gly Gly Gly Thr Lys Val Met Ile
                100                 105

<210> SEQ ID NO 37
<211> LENGTH: 109
<212> TYPE: PRT
<213> ORGANISM: Homo sapiens

<400> SEQUENCE: 37

Lys Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Gly Asn
                20                  25                  30

Tyr Leu Ala Trp Tyr Gln Gln Arg Pro Gly Gln Ala Pro Arg Leu Leu
            35                  40                  45

Ile Tyr Gly Ala Ser Thr Arg Ala Thr Gly Ile Pro Ala Arg Phe Ser
        50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Gly Lys Trp Pro
                85                  90                  95

Pro Leu Thr Thr Phe Gly Gly Gly Thr Lys Val Glu Ile
                100                 105

<210> SEQ ID NO 38
<211> LENGTH: 109
<212> TYPE: PRT
<213> ORGANISM: Homo sapiens

<400> SEQUENCE: 38

Lys Ile Val Met Thr Gln Ser Pro Val Thr Leu Ser Val Ser Pro Gly
1               5                   10                  15

Glu Arg Ala Thr Leu Ser Cys Arg Ala Cys Gln Ser Val Ser Gly Ser
                20                  25                  30
```

```
Tyr Leu Ala Trp Tyr Gln Gln Arg Pro Gly Gln Ala Pro Arg Leu Leu
            35                  40                  45

Ile Tyr Gly Ala Ser Thr Arg Ala Thr Gly Ile Pro Ala Arg Phe Ser
 50                  55                  60

Gly Ser Gly Ser Gly Thr Glu Phe Thr Leu Thr Ile Ser Ser Leu Gln
 65                  70                  75                  80

Ser Glu Asp Phe Ala Val Tyr Tyr Cys Gln Gln Tyr Gly Lys Trp Pro
                 85                  90                  95

Pro Leu Thr Thr Phe Gly Gly Gly Thr Lys Val Glu Ile
                100                 105
```

<210> SEQ ID NO 39
<211> LENGTH: 109
<212> TYPE: PRT
<213> ORGANISM: Homo sapiens

<400> SEQUENCE: 39

```
Lys Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Gly Asn
            20                  25                  30

Tyr Leu Ala Trp Tyr Gln Arg Pro Gly Gln Ala Pro Arg Leu Leu
            35                  40                  45

Ile Tyr Gly Ala Ser Thr Arg Ala Thr Gly Ile Pro Ala Arg Phe Ser
 50                  55                  60

Gly Ser Gly Ser Gly Thr Glu Phe Thr Leu Thr Ile Ser Ser Leu Gln
 65                  70                  75                  80

Ser Glu Asp Phe Ala Val Tyr Tyr Cys Gln Gln Tyr Gly Lys Trp Pro
                 85                  90                  95

Pro Leu Thr Thr Phe Gly Gly Gly Thr Lys Val Glu Ile
                100                 105
```

<210> SEQ ID NO 40
<211> LENGTH: 109
<212> TYPE: PRT
<213> ORGANISM: Homo sapiens

<400> SEQUENCE: 40

```
Lys Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Leu Ser Gly Ser
            20                  25                  30

Tyr Leu Ala Trp Tyr Gln Gln Arg Pro Gly Gln Ala Pro Arg Leu Leu
            35                  40                  45

Ile Tyr Gly Ala Ser Thr Arg Ala Thr Gly Ile Pro Ala Arg Phe Ser
 50                  55                  60

Gly Ser Gly Ser Gly Thr Glu Phe Thr Leu Thr Ile Ser Ser Leu Gln
 65                  70                  75                  80

Ser Glu Asp Phe Ala Val Tyr Tyr Cys Gln Gln Tyr Gly Lys Trp Pro
                 85                  90                  95

Pro Leu Thr Thr Phe Gly Gly Gly Thr Lys Val Glu Ile
                100                 105
```

<210> SEQ ID NO 41
<211> LENGTH: 109
<212> TYPE: PRT
<213> ORGANISM: Homo sapiens

<400> SEQUENCE: 41

Lys Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Gly Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Gly Lys Trp Pro
                85                  90                  95

Pro Leu Thr Thr Phe Gly Gly Gly Thr Lys Val Glu Ile
            100                 105

<210> SEQ ID NO 42
<211> LENGTH: 107
<212> TYPE: PRT
<213> ORGANISM: Homo sapiens

<400> SEQUENCE: 42

Glu Val Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Arg Pro Gly Gln Ala Pro Arg Leu Leu Ile
        35                  40                  45

Tyr Gly Ala Ser Thr Arg Val Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Thr Phe Gly Gly Gly Thr Lys Val Glu Ile
            100                 105

<210> SEQ ID NO 43
<211> LENGTH: 107
<212> TYPE: PRT
<213> ORGANISM: Homo sapiens

<400> SEQUENCE: 43

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Asn Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Lys Phe Ser Gly
    50                  55                  60

Ser Gly Ser Gly Thr Glu Phe Thr Leu Thr Ile Ser Ser Leu Gln Ser
65                  70                  75                  80

Glu Asn Phe Ala Val Tyr Tyr Cys Gln Gln Tyr Asn Lys Trp Pro Leu
                85                  90                  95

-continued

Thr Thr Phe Gly Gly Gly Thr Lys Val Glu Ile
            100                 105

<210> SEQ ID NO 44
<211> LENGTH: 107
<212> TYPE: PRT
<213> ORGANISM: Homo sapiens

<400> SEQUENCE: 44

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Ser Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Thr Phe Gly Gly Gly Thr Lys Val Glu Ile
            100                 105

<210> SEQ ID NO 45
<211> LENGTH: 109
<212> TYPE: PRT
<213> ORGANISM: Homo sapiens

<400> SEQUENCE: 45

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Gly Ser
            20                  25                  30

Tyr Leu Ala Trp Tyr Gln Gln Lys Pro Gly Gln Ala Pro Arg Leu Leu
        35                  40                  45

Ile Tyr Ser Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Asn Trp Pro
                85                  90                  95

Pro Leu Thr Thr Phe Gly Gly Gly Thr Lys Val Glu Ile
            100                 105

<210> SEQ ID NO 46
<211> LENGTH: 99
<212> TYPE: PRT
<213> ORGANISM: Homo sapiens

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

```
              50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Phe Gly Gly Gly Thr Lys Val
                 85                  90                  95

Glu Ile Lys

<210> SEQ ID NO 47
<211> LENGTH: 108
<212> TYPE: PRT
<213> ORGANISM: Homo sapiens

<400> SEQUENCE: 47

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Ile Ile Ser Ser
                 20                  25                  30

Ala Leu Ala Trp Tyr Gln Gln Lys Pro Gly Gln Ala Pro Arg Leu Leu
             35                  40                  45

Ile Tyr Gly Ala Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr His Cys Gln Gln Tyr Gly Ser Thr Pro
                 85                  90                  95

Leu Thr Phe Gly Gly Gly Thr Lys Val Glu Ile Lys
            100                 105

<210> SEQ ID NO 48
<211> LENGTH: 103
<212> TYPE: PRT
<213> ORGANISM: Homo sapiens

<400> SEQUENCE: 48

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gly Gln
                 85                  90                  95

Gly Thr Arg Val Glu Ile Lys
            100

<210> SEQ ID NO 49
<211> LENGTH: 112
<212> TYPE: PRT
<213> ORGANISM: Homo sapiens

<400> SEQUENCE: 49

Asp Val Val Met Thr Gln Ser Pro Leu Ser Leu Pro Val Thr Leu Gly
  1               5                  10                  15
```

-continued

Gln Pro Ala Ser Ile Ser Cys Arg Ser Ser Gln Ser Leu Val Tyr Gly
            20                  25                  30

Asp Gly Asn Thr Tyr Leu Asn Trp Phe Gln Gln Arg Pro Gly His Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Thr Phe Gly Gln Gly Thr Arg Val Glu Ile Lys
            100                 105                 110

<210> SEQ ID NO 50
<211> LENGTH: 112
<212> TYPE: PRT
<213> ORGANISM: Homo sapiens

<400> SEQUENCE: 50

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly His Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Thr Phe Gly Gln Gly Thr Arg Val Glu Ile Lys
            100                 105                 110

<210> SEQ ID NO 51
<211> LENGTH: 112
<212> TYPE: PRT
<213> ORGANISM: Homo sapiens

<400> SEQUENCE: 51

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Arg Val Glu Ile Lys
            100                 105                 110

<210> SEQ ID NO 52
<211> LENGTH: 98

-continued

```
<212> TYPE: PRT
<213> ORGANISM: Homo sapiens

<400> SEQUENCE: 52

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Phe Gly Gln Gly Thr Arg Leu Glu
                 85                  90                  95

Ile Lys

<210> SEQ ID NO 53
<211> LENGTH: 108
<212> TYPE: PRT
<213> ORGANISM: Homo sapiens

<400> SEQUENCE: 53

Lys Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp His Gln Gln Lys Pro Gly Gln Pro Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Lys Trp Pro Pro
                 85                  90                  95

Val Thr Phe Gly Gln Gly Thr Arg Leu Glu Ile Lys
             100                 105

<210> SEQ ID NO 54
<211> LENGTH: 396
<212> TYPE: DNA
<213> ORGANISM: Homo sapiens

<400> SEQUENCE: 54
atggaatttg actttgctg ggttttcctc gttgctcttt taagaggtgt ccagtgtcag    60
gtgcagctgg tggagtctgg gggaggcgtg gtccagcctg gaggtccct gagactctcc   120 tgtgcagcgt ctggattcac cttcagtaac tatggcatgc actgggtccg ccaggctcca   180 ggcaagggc tggagtgggt ggctgttata tggtatgatg gaagtaagag attctatgca   240
ggctccgtga agggccgatt caccatctcc agagacaatt ccaagaacac gctgtatctg   300
caaatgaaca gcctgagagc cgaggacacg gctgtgtatt actgtgcgag aactacagac   360
tactggggcc aggaaccat ggtcaccgtc tcctca                              396

<210> SEQ ID NO 55
<211> LENGTH: 132
```

<212> TYPE: PRT
<213> ORGANISM: Homo sapiens

<400> SEQUENCE: 55

```
Met Glu Phe Gly Leu Cys Trp Val Phe Leu Val Ala Leu Leu Arg Gly
 1               5                  10                  15
Val Gln Cys Gln Val Gln Leu Val Glu Ser Gly Gly Gly Val Val Gln
             20                  25                  30
Pro Gly Arg Ser Leu Arg Leu Ser Cys Ala Ala Ser Gly Phe Thr Phe
         35                  40                  45
Ser Asn Tyr Gly Met His Trp Val Arg Gln Ala Pro Gly Lys Gly Leu
     50                  55                  60
Glu Trp Val Ala Val Ile Trp Tyr Asp Gly Ser Lys Arg Phe Tyr Ala
 65                  70                  75                  80
Gly Ser Val Lys Gly Arg Phe Thr Ile Ser Arg Asp Asn Ser Lys Asn
                 85                  90                  95
Thr Leu Tyr Leu Gln Met Asn Ser Leu Arg Ala Glu Asp Thr Ala Val
            100                 105                 110
Tyr Tyr Cys Ala Arg Thr Thr Asp Tyr Trp Gly Gln Gly Thr Met Val
        115                 120                 125
Thr Val Ser Ser
    130
```

<210> SEQ ID NO 56
<211> LENGTH: 398
<212> TYPE: DNA
<213> ORGANISM: Homo sapiens

<400> SEQUENCE: 56

```
tgagggtccc cgctcagctc ctggggctgc taatgctctg gatacctgga tccaatgcag     60
atattgtgat gacccagact ccactctctc tgtccgtcac ccctggacag ccggcctcca    120
tctcctgcaa gtctagtcag agcctcctgc atagtgatgg aaagacctat ttgtattggt    180
acctgcagaa gccaggccag cctccacagc tcctgatcta tgaagtttcc aaccggttct    240
ctggagtgcc agataggttc agtggcagcg ggtcagggac agatttcaca ctgaaaatca    300
gccgggtgga ggctgaggat gttgggcttt attggtgcat gcaaagtata cagcttccga    360
tcaccttcgg ccaggggaca cgactggaga ttaaacga                            398
```

<210> SEQ ID NO 57
<211> LENGTH: 132
<212> TYPE: PRT
<213> ORGANISM: Homo sapiens

<400> SEQUENCE: 57

```
Met Arg Val Pro Ala Gln Leu Leu Gly Leu Leu Met Leu Trp Ile Pro
 1               5                  10                  15
Gly Ser Asn Ala Asp Ile Val Met Thr Gln Thr Pro Leu Ser Leu Ser
             20                  25                  30
Val Thr Pro Gly Gln Pro Ala Ser Ile Ser Cys Lys Ser Ser Gln Ser
         35                  40                  45
Leu Leu His Ser Asp Gly Lys Thr Tyr Leu Tyr Trp Tyr Leu Gln Lys
     50                  55                  60
Pro Gly Gln Pro Pro Gln Leu Leu Ile Tyr Glu Val Ser Asn Arg Phe
 65                  70                  75                  80
Ser Gly Val Pro Asp Arg Phe Ser Gly Ser Gly Ser Gly Thr Asp Phe
                 85                  90                  95
```

Thr Leu Lys Ile Ser Arg Val Glu Ala Glu Asp Val Gly Leu Tyr Trp
            100                 105                 110

Cys Met Gln Ser Ile Gln Leu Pro Ile Thr Phe Gly Gln Gly Thr Arg
        115                 120                 125

Leu Glu Ile Lys
    130

<210> SEQ ID NO 58
<211> LENGTH: 405
<212> TYPE: DNA
<213> ORGANISM: Homo sapiens

<400> SEQUENCE: 58
atggagttgg gactgcgctg ggttttcctc gttgctcttt taagaggtgt ccagtgtcag      60
gtgcagttgg tggagtctgg gggaggcgtg gtccagcctg gaggtccct gagactctcc     120 tgtgcagcgt ctggattcac cttcagtaac tatggcatgc actgggtccg ccaggctcca     180 ggcaagggc tggagtgggt ggcagttata tggtatgatg aagtaataa atactatgca      240 gactccgtga agggccgatt caccatctcc agagacaatt cgaagaacac gctgtatctg     300
caaatgaaca gcctgagagc cgaggacacg gctgtgtatt actgtgcgag agggggggt      360 gactttgact actggggcca gggaaccctg gtcaccgtct cctca                    405

<210> SEQ ID NO 59
<211> LENGTH: 135
<212> TYPE: PRT
<213> ORGANISM: Homo sapiens

<400> SEQUENCE: 59

Met Glu Leu Gly Leu Arg Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Gly Gly Asp Phe Asp Tyr Trp Gly Gln Gly
        115                 120                 125

Thr Leu Val Thr Val Ser Ser
    130                 135

<210> SEQ ID NO 60
<211> LENGTH: 387
<212> TYPE: DNA
<213> ORGANISM: Homo sapiens

<400> SEQUENCE: 60
atggaagccc agctcagct tctcttcctc ctgctactct ggctcccaga tattactgga      60
gaaatagtga tgacgcagtc tccagccacc ctgtctgtgt ctccagggga aagagtcacc     120

```
ctctcctgca gggccagtca gactattagc ggcagctact tagcctggta ccaacagaaa      180
cctggccagg ctccccggct cctcatctat ggtgcattta ccagggccac tggtatccca      240
gccaggttca gtggcagtgg gtctgggaca gaattcactc tcaccatcag cagcctgcag      300
tctgaagatt ttgcagttta ttactgtcag cagtataata actggcctcc gctcactttc      360
ggcggaggga ccagggtgga gatcaaa                                          387
```

<210> SEQ ID NO 61
<211> LENGTH: 129
<212> TYPE: PRT
<213> ORGANISM: Homo sapiens

<400> SEQUENCE: 61

```
Met Glu Ala Pro Ala Gln Leu Leu Phe Leu Leu Leu Leu Trp Leu Pro
 1               5                  10                  15

Asp Ile Thr Gly Glu Ile Val Met Thr Gln Ser Pro Ala Thr Leu Ser
            20                  25                  30

Val Ser Pro Gly Glu Arg Val Thr Leu Ser Cys Arg Ala Ser Gln Thr
        35                  40                  45

Ile Ser Gly Ser Tyr Leu Ala Trp Tyr Gln Gln Lys Pro Gly Gln Ala
    50                  55                  60

Pro Arg Leu Leu Ile Tyr Gly Ala Phe Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Asn Asn Trp Pro Pro Leu Thr Phe Gly Gly Gly Thr Arg Val Glu Ile
        115                 120                 125

Lys
```

<210> SEQ ID NO 62
<211> LENGTH: 405
<212> TYPE: DNA
<213> ORGANISM: Homo sapiens

<400> SEQUENCE: 62

```
atggagttgg ggctccgctg gattttcctc gttgctcttt taagaggtgt ccagtgtcag       60
gtgcagctgg tggagtctgg gggaggcgtg gtccagcctg gaggtccct gagactctcc      120 tgtgcagcgt ctggattcac cttcagtaaa tttggcatgc actgggtccg ccaggctcca      180 gacaagggc tggagtgggt ggcagttata tggtatgatg aacttataa atactatgca      240 gactccgtga agggccgatt caccatctcc agagacaatt ccaagaacac gctgtatctg      300
caaatgaaca gcctgagagc cgaggacacg gctgtgtatt actgtgcgag aggaggtgga      360
tcttttgact attgggcca gggaaccctg gtcaccgtct cctca                       405
```

<210> SEQ ID NO 63
<211> LENGTH: 135
<212> TYPE: PRT
<213> ORGANISM: Homo sapiens

<400> SEQUENCE: 63

```
Met Glu Leu Gly Leu Arg Trp Ile Phe Leu Val Ala Leu Leu Arg Gly
 1               5                  10                  15

Val Gln Cys Gln Val Gln Leu Val Glu Ser Gly Gly Gly Val Val Gln
            20                  25                  30
```

```
Pro Gly Arg Ser Leu Arg Leu Ser Cys Ala Ala Ser Gly Phe Thr Phe
            35                  40                  45

Ser Lys Phe Gly Met His Trp Val Arg Gln Ala Pro Asp Lys Gly Leu
 50                  55                  60

Glu Trp Val Ala Val Ile Trp Tyr Asp Gly Thr Tyr Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Gly Gly Gly Ser Phe Asp Tyr Trp Gly Gln Gly
            115                 120                 125

Thr Leu Val Thr Val Ser Ser
            130                 135

<210> SEQ ID NO 64
<211> LENGTH: 396
<212> TYPE: DNA
<213> ORGANISM: Homo sapiens

<400> SEQUENCE: 64
atgaggctcc ctgctcagct cctggggctg ctaatgctct ggatacctga atccagtgca      60
gatattgtga tgacccagac tccactctct ctgtccgtca cccctggaca gccggcctcc     120
atctcctgca gtctagtca gagcctcctg catagtgatg aaagaccctt tttgtattgg      180
tacctgcaga agccaggcca gcctccacag ctcctgatct atgaagtctc caaccggttc    240
tctggagtgc cagataggtt cagtggcagc gggtcaggga tagatttcac actgaaaatc    300
agccgggtgg aggctgagga tgttggggtt tattactgca tgcaaagtat acagttccg    360 atcaccttcg gccaagggac acgactggag attaaa                              396

<210> SEQ ID NO 65
<211> LENGTH: 132
<212> TYPE: PRT
<213> ORGANISM: Homo sapiens

<400> SEQUENCE: 65

Met Arg Leu Pro Ala Gln Leu Leu Gly Leu Leu Met Leu Trp Ile Pro
 1               5                  10                  15

Glu Ser Ser Ala Asp Ile Val Met Thr Gln Thr Pro Leu Ser Leu Ser
             20                  25                  30

Val Thr Pro Gly Gln Pro Ala Ser Ile Ser Cys Lys Ser Ser Gln Ser
            35                  40                  45

Leu Leu His Ser Asp Gly Lys Thr Phe Leu Tyr Trp Tyr Leu Gln Lys
 50                  55                  60

Pro Gly Gln Pro Pro Gln Leu Leu Ile Tyr Glu Val Ser Asn Arg Phe
 65                  70                  75                  80

Ser Gly Val Pro Asp Arg Phe Ser Gly Ser Gly Ser Gly Ile Asp Phe
                 85                  90                  95

Thr Leu Lys Ile Ser Arg Val Glu Ala Glu Asp Val Gly Val Tyr Tyr
            100                 105                 110

Cys Met Gln Ser Ile Gln Phe Pro Ile Thr Phe Gly Gln Gly Thr Arg
            115                 120                 125

Leu Glu Ile Lys
            130
```

<210> SEQ ID NO 66
<211> LENGTH: 405
<212> TYPE: DNA
<213> ORGANISM: Homo sapiens

<400> SEQUENCE: 66

| | | | | | |
|---|---|---|---|---|---|
| atggaattgg | gacttcgctg | ggttttcctc | gttgctcttt | taagaggtgt | ccagtgtcag | 60 |
| gtgcagctgg | tggagtctgg | gggaggcgtg | gtccagcctg | ggaggtccct | gagactctcc | 120 |
| tgtgcagcgt | ctggattcac | cttcagtaaa | tttggcatgc | actgggtccg | ccaggctcca | 180 |
| gacaaggggc | tggagtgggt | ggcagttata | tggtatgatg | aagttataaa | atactatgca | 240 |
| gactccgtga | aggccgatt | caccatctcc | agagacaatt | ccaagaacac | gctgtatctg | 300 |
| caaatgaaca | gcctgagagc | cgaggacacg | gctgcgtatt | actgtgcgag | aggaggtgga | 360 |
| tcttttgact | actggggcca | gggaaccctg | gtcaccgtct | cctca | | 405 |

<210> SEQ ID NO 67
<211> LENGTH: 135
<212> TYPE: PRT
<213> ORGANISM: Homo sapiens

<400> SEQUENCE: 67

Met Glu Leu Gly Leu Arg Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Lys Phe Gly Met His Trp Val Arg Gln Ala Pro Asp Lys Gly Leu
    50                  55                  60

Glu Trp Val Ala Val Ile Trp Tyr Asp Gly Ser Tyr Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Ala
            100                 105                 110

Tyr Tyr Cys Ala Arg Gly Gly Gly Ser Phe Asp Tyr Trp Gly Gln Gly
        115                 120                 125

Thr Leu Val Thr Val Ser Ser
    130                 135

<210> SEQ ID NO 68
<211> LENGTH: 396
<212> TYPE: DNA
<213> ORGANISM: Homo sapiens

<400> SEQUENCE: 68

| | | | | | |
|---|---|---|---|---|---|
| atgagggtcc | ccgctcagct | cctggggctg | ctaatgctct | ggatacctgg | atccagtgca | 60 |
| gatattgtga | tgacccagac | tccactctct | ctgtccgtca | cccctggaca | gccggcctcc | 120 |
| atctcctgca | agtctagtca | gagcctcctg | catagtgatg | gaaagacctt | tttgtattgg | 180 |
| tacctgcaga | agccaggcca | gcctccacag | ctcctgatct | atgaagtctc | caaccggttc | 240 |
| tctggagtgc | cagataggtt | cagtggcagc | gggtcaggga | cagatttcac | actgaaaatc | 300 |
| agccgggtgg | aggctgagga | tgttggggtt | tattactgca | tgcaaagtat | acagtttccg | 360 |
| atcaccttcg | gccaagggac | acgactggag | attaaa | | | 396 |

<210> SEQ ID NO 69
<211> LENGTH: 132
<212> TYPE: PRT
<213> ORGANISM: Homo sapiens

<400> SEQUENCE: 69

Met Arg Val Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Ser Asp Gly Lys Thr Phe Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Ile Asp Phe
                85                  90                  95

Thr Leu Lys Ile Ser Arg Val Glu Ala Glu Asp Val Gly Val Tyr Tyr
            100                 105                 110

Cys Met Gln Ser Ile Gln Phe Pro Ile Thr Phe Gly Gln Gly Thr Arg
        115                 120                 125

Leu Glu Ile Lys
    130

<210> SEQ ID NO 70
<211> LENGTH: 405
<212> TYPE: DNA
<213> ORGANISM: Homo sapiens

<400> SEQUENCE: 70
atggagttgg ggctttgctg ggttttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagtagc tatggcatgc actgggtccg ccaggctcca     180 gacaagggc tggagtgggt ggcagttata tggtatgatg aagttataa atactatgca       240 gactccgtga aggccgatt caccatctcc agagacaatt ccaagaacac gctgtatctg      300
caaatgaaca gcctgagagc cgaggacacg gctgtgtatt actgtgcgag aggaggtgga    360
tcttttgact actggggcca gggaaccctg gtcaccgtct cctca                     405

<210> SEQ ID NO 71
<211> LENGTH: 135
<212> TYPE: PRT
<213> ORGANISM: Homo sapiens

<400> SEQUENCE: 71

Met Glu Leu Gly Leu Cys Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Asp Lys Gly Leu
    50                  55                  60

Glu Trp Val Ala Val Ile Trp Tyr Asp Gly Ser Tyr Lys Tyr Tyr Ala
65                  70                  75                  80

```
Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Gly Gly Ser Phe Asp Tyr Trp Gly Gln Gly
        115                 120                 125

Thr Leu Val Thr Val Ser Ser
        130             135

<210> SEQ ID NO 72
<211> LENGTH: 396
<212> TYPE: DNA
<213> ORGANISM: Homo sapiens

<400> SEQUENCE: 72
atgagggtcc ccgctcagct cctggggctg ctaatgctct ggataccttgg atccagtgct    60 gatattgtga tgacccagac tccactctct ctgtccgtca cccctggaca gccggcctcc    120
atctcctgca agtctagtca gagcctccta catagagatg gaaagacctt tttgtattgg    180
tacctgcaga agccaggcca gcctccacag ctcctgatct atgaagtttc caaccggttc    240
tctggagtgc cagataggtt cagtggcagc gggtcaggga cagatttcac actgaaaatc    300
agccgggtgg aggctgagga tgttggggtt tattactgca tgcaaagtat acagtttccg    360
atcaccttcg gccaagggac acgactggag attaaa                              396

<210> SEQ ID NO 73
<211> LENGTH: 132
<212> TYPE: PRT
<213> ORGANISM: Homo sapiens

<400> SEQUENCE: 73

Met Arg Val Pro Ala Gln Leu Leu Gly Leu Leu Met Leu Trp Ile Pro
  1               5                  10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Arg Asp Gly Lys Thr Phe Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ser Ile Gln Phe Pro Ile Thr Phe Gly Gln Gly Thr Arg
        115                 120                 125

Leu Glu Ile Lys
        130

<210> SEQ ID NO 74
<211> LENGTH: 404
<212> TYPE: DNA
<213> ORGANISM: Homo sapiens

<400> SEQUENCE: 74
tggaattggg gctgcgctgg gttttcctcg ttgctctttt aagaggtgtc cagtgtcagg    60
```

```
tgcagctggt ggagtctggg ggaggcgtgg tccagcctgg gaggtccctg agactctcct      120
gtgcagcgtc tggattcacc ttcagtcgct atggcatgca ctgggtccgc caggctccag      180 gcaagggct ggagtgggtg gcagttatat ggtatgatgg aagtaataaa tactatgcag       240
actccgtgaa gggccgattc accatctcca gagacaattc caagaacacg ctatatctgc      300
aagtgaacag cctgagagcc gaggacacgg ctgtgtatta ctgtgcgaga ggaggtggat      360
cttttgacta ctggggccag ggaaccctgg tcaccgtctc ctca                       404

<210> SEQ ID NO 75
<211> LENGTH: 135
<212> TYPE: PRT
<213> ORGANISM: Homo sapiens

<400> SEQUENCE: 75

Met Glu Leu Gly Leu Arg Trp Val Phe Leu Val Ala Leu Leu Arg Gly
  1               5                  10                  15

Val Gln Cys Gln Val Gln Leu Val Glu Ser Gly Gly Gly Val Val Gln
                 20                  25                  30

Pro Gly Arg Ser Leu Arg Leu Ser Cys Ala Ala Ser Gly Phe Thr Phe
             35                  40                  45

Ser Arg Tyr Gly Met His Trp Val Arg Gln Ala Pro Gly Lys Gly Leu
         50                  55                  60

Glu Trp Val Ala Val Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Val Asn Ser Leu Arg Ala Glu Asp Thr Ala Val
            100                 105                 110

Tyr Tyr Cys Ala Arg Gly Gly Gly Ser Phe Asp Tyr Trp Gly Gln Gly
        115                 120                 125

Thr Leu Val Thr Val Ser Ser
    130                 135

<210> SEQ ID NO 76
<211> LENGTH: 396
<212> TYPE: DNA
<213> ORGANISM: Homo sapiens

<400> SEQUENCE: 76
atgagggtcc ccgctcagct cctggggctg ctaatgctct ggatacctgg atccagtgca       60
gatattgtga tgacccagac tccactctct ctgtccgtca cccctggaca gccggcctcc      120
atctcctgca gtctagtca gagcctcctg catagtgatg gaaagacctt tttgtattgg       180
tacctgcaga agccaggcca gcctccacag ctcctgatct atgaagtttc caaccggttc      240
tctggagtgc cagataggtt tggtggcagc gggtcaggga cagatttac actgaaaatc      300 agccgggtgg aggctgagga tgttggggtt tattactgca tgcaaagtat acagtttccg      360
atcaccttcg gccaagggac acgactggag attgaa                                396

<210> SEQ ID NO 77
<211> LENGTH: 132
<212> TYPE: PRT
<213> ORGANISM: Homo sapiens

<400> SEQUENCE: 77

Met Arg Val Pro Ala Gln Leu Leu Gly Leu Leu Met Leu Trp Ile Pro
  1               5                  10                  15
```

```
          1               5                  10                 15
Gly Ser Ser Ala Asp Ile Val Met Thr Gln Thr Pro Leu Ser Leu Ser
                 20                 25                 30

Val Thr Pro Gly Gln Pro Ala Ser Ile Ser Cys Lys Ser Ser Gln Ser
             35                 40                 45

Leu Leu His Ser Asp Gly Lys Thr Phe Leu Tyr Trp Tyr Leu Gln Lys
         50                 55                 60

Pro Gly Gln Pro Pro Gln Leu Leu Ile Tyr Glu Val Ser Asn Arg Phe
 65                 70                 75                 80

Ser Gly Val Pro Asp Arg Phe Gly Gly Ser Gly Ser Gly Thr Asp Phe
                 85                 90                 95

Thr Leu Lys Ile Ser Arg Val Glu Ala Glu Asp Val Gly Val Tyr Tyr
            100                105                110

Cys Met Gln Ser Ile Gln Phe Pro Ile Thr Phe Gly Gln Gly Thr Arg
            115                120                125

Leu Glu Ile Glu
        130

<210> SEQ ID NO 78
<211> LENGTH: 405
<212> TYPE: DNA
<213> ORGANISM: Homo sapiens

<400> SEQUENCE: 78
atggagttgg gactgcgctg gattttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagtaac tatggcatgc actgggtccg ccaggctcca     180
ggcaaggggc tggagtgggt ggcagttata tggtatgatg gaagtaaaaa attctatgca     240
gactccgtga agggccgatt caccatctcc agagacaatt ccaagaacat gcagtatctg     300
caaatggaca gcctgagagc cgaggacacg gctgtgtatt actgtgcgag aggcgggggg     360
gactttgact actggggcca gggaatcctg gtcaccgtct cctca                    405

<210> SEQ ID NO 79
<211> LENGTH: 135
<212> TYPE: PRT
<213> ORGANISM: Homo sapiens

<400> SEQUENCE: 79

Met Glu Leu Gly Leu Arg Trp Ile Phe Leu Val Ala Leu Leu Arg Gly
 1               5                  10                 15

Val Gln Cys Gln Val Gln Leu Val Glu Ser Gly Gly Gly Val Val Gln
                 20                 25                 30

Pro Gly Arg Ser Leu Arg Leu Ser Cys Ala Ala Ser Gly Phe Thr Phe
             35                 40                 45

Ser Asn Tyr Gly Met His Trp Val Arg Gln Ala Pro Gly Lys Gly Leu
         50                 55                 60

Glu Trp Val Ala Val Ile Trp Tyr Asp Gly Ser Lys Lys Phe Tyr Ala
 65                 70                 75                 80

Asp Ser Val Lys Gly Arg Phe Thr Ile Ser Arg Asp Asn Ser Lys Asn
                 85                 90                 95

Met Gln Tyr Leu Gln Met Asp Ser Leu Arg Ala Glu Asp Thr Ala Val
            100                105                110

Tyr Tyr Cys Ala Arg Gly Gly Gly Asp Phe Asp Tyr Trp Gly Gln Gly
            115                120                125
```

```
Ile Leu Val Thr Val Ser Ser
    130             135
```

<210> SEQ ID NO 80
<211> LENGTH: 387
<212> TYPE: DNA
<213> ORGANISM: Homo sapiens

<400> SEQUENCE: 80

```
atggaaaccc cagcgcagct tctcttcctc ctgctactct ggctcccaga taccactgga      60
gaaatagtga tgacgcagtc tccagccacc ctgtctgtgt ctccagggga aagagccacc     120
ctctcctgca gggccagtca gaatcttagc ggcaagtact tagcctggta ccagcagaaa     180
cctggccagg ctcccagtcg cctcatctat ggtacatcca ccagggccac tggtgtccca     240
gccaggttca gtggcagtgg gtctgggaca gagttcactc tcaccatcag cagcctgcag     300
tctgaagatt ctgcagttta ttactgtcag cagtataata ttggcctcc gctcactttc      360
ggcggaggga ccaaggtgga gatcaaa                                          387
```

<210> SEQ ID NO 81
<211> LENGTH: 129
<212> TYPE: PRT
<213> ORGANISM: Homo sapiens

<400> SEQUENCE: 81

```
Met Glu Thr Pro Ala Gln Leu Leu Phe Leu Leu Leu Trp Leu Pro
  1               5                  10                  15

Asp Thr Thr Gly Glu Ile Val Met Thr Gln Ser Pro Ala Thr Leu Ser
                 20                  25                  30

Val Ser Pro Gly Glu Arg Ala Thr Leu Ser Cys Arg Ala Ser Gln Asn
             35                  40                  45

Leu Ser Gly Lys Tyr Leu Ala Trp Tyr Gln Gln Lys Pro Gly Gln Ala
         50                  55                  60

Pro Ser Arg Leu Ile Tyr Gly Thr Ser Thr Arg Ala Thr Gly Val Pro
 65                  70                  75                  80

Ala Arg Phe Ser Gly Ser Gly Ser Gly Thr Glu Phe Thr Leu Thr Ile
                 85                  90                  95

Ser Ser Leu Gln Ser Glu Asp Ser Ala Val Tyr Tyr Cys Gln Gln Tyr
            100                 105                 110

Asn Asn Trp Pro Pro Leu Thr Phe Gly Gly Gly Thr Lys Val Glu Ile
        115                 120                 125

Lys
```

<210> SEQ ID NO 82
<211> LENGTH: 405
<212> TYPE: DNA
<213> ORGANISM: Homo sapiens

<400> SEQUENCE: 82

```
atggaattgg gactgagctg gttttcctc gttgctcttt taagaggtgt ccagggtcag       60
gtgcagctgg tggagtctgg gggaggcgtg gtccagcctg gaagtccct gagactctcc      120
tgtgcagcgt ctggattcac cttcagaaac tatggcatgc actgggtccg ccaggctcca     180
ggcaagggc tggagtgggt ggcagttata tggtatgatg aagtaagaa attctatgca       240
gattccgtga aggccgatt caccatctcc agagacaatt ccaagaacac gctgaatctg      300
caaatgaaca gcctgagagc cgaggacacg gctgtgtatt actgtgtgag aggcgggggg     360
```

```
gactttgact actggggcca gggaaccctg gtcaccgtct cctca          405
```

<210> SEQ ID NO 83
<211> LENGTH: 135
<212> TYPE: PRT
<213> ORGANISM: Homo sapiens

<400> SEQUENCE: 83

Met Glu Leu Gly Leu Ser Trp Val Phe Leu Val Ala Leu Leu Arg Gly
1               5                   10                  15

Val Gln Gly Gln Val Gln Leu Val Glu Ser Gly Gly Gly Val Val Gln
            20                  25                  30

Pro Gly Lys Ser Leu Arg Leu Ser Cys Ala Ala Ser Gly Phe Thr Phe
        35                  40                  45

Arg Asn Tyr Gly Met His Trp Val Arg Gln Ala Pro Gly Lys Gly Leu
    50                  55                  60

Glu Trp Val Ala Val Ile Trp Tyr Asp Gly Ser Lys Lys Phe Tyr Ala
65                  70                  75                  80

Asp Ser Val Lys Gly Arg Phe Thr Ile Ser Arg Asp Asn Ser Lys Asn
                85                  90                  95

Thr Leu Asn Leu Gln Met Asn Ser Leu Arg Ala Glu Asp Thr Ala Val
            100                 105                 110

Tyr Tyr Cys Val Arg Gly Gly Gly Asp Phe Asp Tyr Trp Gly Gln Gly
        115                 120                 125

Thr Leu Val Thr Val Ser Ser
    130                 135

<210> SEQ ID NO 84
<211> LENGTH: 387
<212> TYPE: DNA
<213> ORGANISM: Homo sapiens

<400> SEQUENCE: 84

```
atggaaaccc cagcgcagct tctcttcctc ctgctactct ggctcccaga tagcactgga     60
gaaattgtga tgacgcagtc tccagccacc ctgtctgtgt ctctagggga aagagccacc    120
ctctcctgca gggccagtca gaatatcagc ggcaactact tagcctggta tcagcagaga    180
cctggccagg ctcccagacg cctcatctat agtgcatcct ccaggccac tggtatccca     240
gacaggttca gtggcagtgg gtctgggaca gagttcactc tcaccatcag cagcctacag    300
tctgaagatt ttgcagtttta ttactgtcag cagtataata ctggccccc gctcactttc    360
ggcggaggga ccaaggtgga gatgaaa                                        387
```

<210> SEQ ID NO 85
<211> LENGTH: 129
<212> TYPE: PRT
<213> ORGANISM: Homo sapiens

<400> SEQUENCE: 85

Met Glu Thr Pro Ala Gln Leu Leu Phe Leu Leu Leu Leu Trp Leu Pro
1               5                   10                  15

Asp Ser Thr Gly Glu Ile Val Met Thr Gln Ser Pro Ala Thr Leu Ser
            20                  25                  30

Val Ser Leu Gly Glu Arg Ala Thr Leu Ser Cys Arg Ala Ser Gln Asn
        35                  40                  45

Ile Ser Gly Asn Tyr Leu Ala Trp Tyr Gln Gln Arg Pro Gly Gln Ala
    50                  55                  60

```
Pro Arg Arg Leu Ile Tyr Ser Ala Ser Ser Arg Ala Thr Gly Ile Pro
 65                  70                  75                  80

Asp Arg Phe Ser Gly Ser Gly Ser Gly Thr Glu Phe Thr Leu Thr Ile
                 85                  90                  95

Ser Ser Leu Gln Ser Glu Asp Phe Ala Val Tyr Tyr Cys Gln Gln Tyr
            100                 105                 110

Asn Asn Trp Pro Pro Leu Thr Phe Gly Gly Gly Thr Lys Val Glu Met
        115                 120                 125

Lys
```

<210> SEQ ID NO 86
<211> LENGTH: 414
<212> TYPE: DNA
<213> ORGANISM: Homo sapiens

<400> SEQUENCE: 86

```
atggagtttg ggctctgctg gattttctt gtggctattt taaaaggtgt ccagtgtgcg      60
gtgcagctgt tggagtctgg gggaggcttg atacagcctg ggggtccct gagactctcc    120
tgtgcagcct ctggattcac ctttagcagc tatgccatga gctgggtccg ccaggctcca    180
gggaaggggc tggagtgggt ctcagctatt agtggtagtg gtggtagcac attctacgca    240
gactccgtga ggggccggtt caccatctcc agagacaatt ccaagaacac gctgtatctg    300
caaatgaaca gcctgagagt cgaggacacg gccgtatatt actgtgcgaa agaagtaatg    360
ggacctatct tttttgacta ctggggccag ggaaccctgg tcaccgtctc ctca          414
```

<210> SEQ ID NO 87
<211> LENGTH: 138
<212> TYPE: PRT
<213> ORGANISM: Homo sapiens

<400> SEQUENCE: 87

```
Met Glu Phe Gly Leu Cys Trp Ile Phe Leu Val Ala Ile Leu Lys Gly
 1               5                  10                  15

Val Gln Cys Ala Val Gln Leu Leu Glu Ser Gly Gly Gly Leu Ile Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Phe Tyr Ala
 65                  70                  75                  80

Asp Ser Val Arg Gly Arg Phe Thr Ile Ser Arg Asp Asn Ser Lys Asn
                 85                  90                  95

Thr Leu Tyr Leu Gln Met Asn Ser Leu Arg Val Glu Asp Thr Ala Val
            100                 105                 110

Tyr Tyr Cys Ala Lys Glu Val Met Gly Pro Ile Phe Phe Asp Tyr Trp
        115                 120                 125

Gly Gln Gly Thr Leu Val Thr Val Ser Ser
        130                 135
```

<210> SEQ ID NO 88
<211> LENGTH: 384
<212> TYPE: DNA
<213> ORGANISM: Homo sapiens

<400> SEQUENCE: 88

```
atggaaaccc cagcgcagct tctcttcctc ctgctactct ggctcccaga taccaccgga      60
gaaattgttt tgacgcagtc tccaggcacc ctgtctttgt ctccagggga agagccacc      120 ctctcctgca gggccagtca gagtattatc agcagcgcct tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta tcactgtcag cagtatggta gcacccgct cactttcggc      360 ggagggacca aggtggagat caaa                                            384
```

<210> SEQ ID NO 89
<211> LENGTH: 128
<212> TYPE: PRT
<213> ORGANISM: Homo sapiens

<400> SEQUENCE: 89

```
Met Glu Thr Pro Ala Gln Leu Leu Phe Leu Leu Leu Trp Leu Pro
 1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Ile Ile Ser Ser Ala Leu Ala Trp Tyr Gln Gln Lys Pro Gly Gln Ala
     50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr His Cys Gln Gln Tyr
            100                 105                 110

Gly Ser Thr Pro Leu Thr Phe Gly Gly Gly Thr Lys Val Glu Ile Lys
        115                 120                 125
```

<210> SEQ ID NO 90
<211> LENGTH: 405
<212> TYPE: DNA
<213> ORGANISM: Homo sapiens

<400> SEQUENCE: 90

```
atggaattgg gactgtgctg gcttttcctc gttgctcttt taagaggtgt ccagtgtcag      60
gtgcagctgg tggagtctgg gggaggcgtg gtccagcctg ggaggtccct gagagtctcc     120
tgtgaagcgt ctggattcac cttcagtaac tatggcatgc actgggtccg ccaggctcca     180 ggcaagggc tggaatgggt ggcagttata tggtatgatg aagtaaaaa attctatgca       240 gactccgtga aggccgatt caccatctcc agagacaatt cccagaacac gctgtctctg      300
caaatgagca gcctgagagc cgaggacacg gctgtgtatt actgtgcgag aggcggtggg     360
gactttgact ctgggggcca gggaaccctg gtcaccgtct cctca                     405
```

<210> SEQ ID NO 91
<211> LENGTH: 135
<212> TYPE: PRT
<213> ORGANISM: Homo sapiens

<400> SEQUENCE: 91

```
Met Glu Leu Gly Leu Cys Trp Leu Phe Leu Val Ala Leu Leu Arg Gly
 1               5                  10                  15
```

Val Gln Cys Gln Val Gln Leu Val Glu Ser Gly Gly Val Val Gln
            20                  25                  30

Pro Gly Arg Ser Leu Arg Val Ser Cys Glu Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Val Ile Trp Tyr Asp Gly Ser Lys Lys Phe Tyr Ala
65                  70                  75                  80

Asp Ser Val Lys Gly Arg Phe Thr Ile Ser Arg Asp Asn Ser Gln Asn
                85                  90                  95

Thr Leu Ser Leu Gln Met Ser Ser Leu Arg Ala Glu Asp Thr Ala Val
            100                 105                 110

Tyr Tyr Cys Ala Arg Gly Gly Asp Phe Asp Phe Trp Gly Gln Gly
        115                 120                 125

Thr Leu Val Thr Val Ser Ser
    130                 135

<210> SEQ ID NO 92
<211> LENGTH: 387
<212> TYPE: DNA
<213> ORGANISM: Homo sapiens

<400> SEQUENCE: 92
atggaaaccc cagcgcagct tctcttcctc ctgctactct ggctcccaga tacctctgga      60
aaaatagtga tgacgcagtc tccagccacc ctgtctgtgt ctccagggga agagccacc     120 ctctcctgta gggccagtca gagtgttagc ggcaactact tagcctggta ccagcagaga     180
cctggccagg ctcccaggct cctcatctat ggtgcatcca ccagggccac tggcatccca     240
gccaggttca gtggcagtgg gtctgggaca gagttcactc tcaccatcag cagcctgcag     300
tctgaagatt ttgcagttta ttactgtcag cagtatggta atggcctcc gctcactttc     360 ggcggaggga ccaaggtgga gatcaaa                                         387

<210> SEQ ID NO 93
<211> LENGTH: 129
<212> TYPE: PRT
<213> ORGANISM: Homo sapiens
<220> FEATURE:
<221> NAME/KEY: UNSURE
<222> LOCATION: (0)...(0)
<223> OTHER INFORMATION: Xaa is any amino acid.

<400> SEQUENCE: 93

Met Glu Thr Pro Ala Gln Xaa Xaa Phe Leu Leu Xaa Leu Trp Leu Pro
1               5                   10                  15

Xaa Xaa Xaa Gly Lys Ile Val Met Thr Gln Ser Pro Xaa Thr Leu Xaa
            20                  25                  30

Val Xaa Pro Gly Glu Xaa Ala Thr Xaa Ser Cys Arg Ala Ser Xaa Ser
        35                  40                  45

Val Ser Gly Asn Tyr Leu Xaa Trp Xaa Gln Gln Xaa Pro Gly Gln Ala
    50                  55                  60

Pro Arg Leu Leu Xaa Tyr Gly Ala Ser Thr Arg Ala Thr Gly Xaa Pro
65                  70                  75                  80

Xaa Arg Phe Xaa Gly Xaa Gly Xaa Gly Thr Xaa Xaa Xaa Xaa Thr Ile
                85                  90                  95

Ser Ser Leu Xaa Xaa Glu Asn Phe Ala Val Xaa Tyr Cys Xaa Gln Tyr
            100                 105                 110

```
Gly Lys Trp Pro Pro Xaa Thr Phe Gly Gly Gly Thr Lys Val Glu Ile
            115                 120                 125
Lys
```

<210> SEQ ID NO 94
<211> LENGTH: 405
<212> TYPE: DNA
<213> ORGANISM: Homo sapiens

<400> SEQUENCE: 94

| | | |
|---|---|---|
| atggagtttg ggctgcgctg ggttttcctc gttgctcttt taagaggtgt ccagtgtcag | 60 |
| gtgcagctgg tggagtctgg gggaggcgtg gtccagcctg gaggtccct gagagtctcc | 120 |
| tgtgcagcgt ctggattcac cttcagtaac tatggcatgc actgggtccg ccaggctcca | 180 |
| ggcaaggggc tggagtgggt ggcagttata tggtatgatg gaagtaaaaa attctatgca | 240 |
| gactccgtga aggccgatt caccatctcc agagacaatt cccagaacac gctgtctctg | 300 |
| caaatgagca gcctgagagc cgaggacacg gctgtgtatt actgtgcgag aggcggtggg | 360 |
| gactttgact ctggggcca gggaaccctg gtcaccgtct cctca | 405 |

<210> SEQ ID NO 95
<211> LENGTH: 135
<212> TYPE: PRT
<213> ORGANISM: Homo sapiens

<400> SEQUENCE: 95

```
Met Glu Phe Gly Leu Arg Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Val Ser Cys Ala Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Val Ile Trp Tyr Asp Gly Ser Lys Lys Phe Tyr Ala
65                  70                  75                  80

Asp Ser Val Lys Gly Arg Phe Thr Ile Ser Arg Asp Asn Ser Gln Asn
                85                  90                  95

Thr Leu Ser Leu Gln Met Ser Ser Leu Arg Ala Glu Asp Thr Ala Val
            100                 105                 110

Tyr Tyr Cys Ala Arg Gly Gly Gly Asp Phe Asp Phe Trp Gly Gln Gly
        115                 120                 125

Thr Leu Val Thr Val Ser Ser
    130                 135
```

<210> SEQ ID NO 96
<211> LENGTH: 387
<212> TYPE: DNA
<213> ORGANISM: Homo sapiens

<400> SEQUENCE: 96

| | | |
|---|---|---|
| atggaaaccc cagctcagct tctcttcctc ctgctactct ggttcccaga tacctctgga | 60 |
| aaaatagtga tgacgcagtc tccagtcacc ctgtctgtgt ctccagggga aagagccacc | 120 |
| ctctcctgta gggcctgtca gagtgttagc ggcagctact tagcctggta ccagcagaga | 180 |
| cctggccagg ctcccaggct cctcatctat ggtgcatcca ccaggccac tggtatccca | 240 |

```
gccaggttca gtggcagtgg gtctgggaca gagttcactc tcaccatcag cagcctgcag    300
tctgaagatt ttgcagttta ttactgtcag cagtatggta aatggcctcc gctcactttc    360
ggcggaggga ccaaggtgga gatcaaa                                         387
```

<210> SEQ ID NO 97
<211> LENGTH: 129
<212> TYPE: PRT
<213> ORGANISM: Homo sapiens

<400> SEQUENCE: 97

```
Met Glu Thr Pro Ala Gln Leu Leu Phe Leu Leu Leu Trp Phe Pro
 1               5                  10                  15

Asp Thr Ser Gly Lys Ile Val Met Thr Gln Ser Pro Val Thr Leu Ser
                20                  25                  30

Val Ser Pro Gly Glu Arg Ala Thr Leu Ser Cys Arg Ala Cys Gln Ser
                35                  40                  45

Val Ser Gly Ser Tyr Leu Ala Trp Tyr Gln Gln Arg Pro Gly Gln Ala
        50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
                100                 105                 110

Gly Lys Trp Pro Pro Leu Thr Phe Gly Gly Gly Thr Lys Val Glu Ile
            115                 120                 125

Lys
```

<210> SEQ ID NO 98
<211> LENGTH: 405
<212> TYPE: DNA
<213> ORGANISM: Homo sapiens

<400> SEQUENCE: 98

```
atggagtttg gactgtgctg ggttttcctc gttgctcttt taagaggtgt ccagtgtcag    60
gtgcagctgg tggagtctgg gggaggcgtg gtccagcctg ggaggtccct gagagtctcc    120
tgtgcagcgt ctggattcac cttcagtaac tatggcatgc actgggtccg ccaggctcca    180 gacaagggc tggagtgggt ggcagttata tggtatgatg gaagtaaaaa attctatgca    240
gactccgtga agggccgatt caccatctcc agagacaatt cccagaacac gctgtctctg    300
caaatgagca gcctgagagc cgaggacacg gctgtttatt actgtgcgag aggcggtggg    360
gactttgact tctggggcca gggaaccctg gtcaccgtct cctca                    405
```

<210> SEQ ID NO 99
<211> LENGTH: 135
<212> TYPE: PRT
<213> ORGANISM: Homo sapiens

<400> SEQUENCE: 99

```
Met Glu Phe Gly Leu Cys Trp Val Phe Leu Val Ala Leu Leu Arg Gly
 1               5                  10                  15

Val Gln Cys Gln Val Gln Leu Val Glu Ser Gly Gly Gly Val Val Gln
                20                  25                  30

Pro Gly Arg Ser Leu Arg Val Ser Cys Ala Ala Ser Gly Phe Thr Phe
            35                  40                  45
```

```
Ser Asn Tyr Gly Met His Trp Val Arg Gln Ala Pro Asp Lys Gly Leu
 50                  55                  60

Glu Trp Val Ala Val Ile Trp Tyr Asp Gly Ser Lys Lys Phe Tyr Ala
 65                  70                  75                  80

Asp Ser Val Lys Gly Arg Phe Thr Ile Ser Arg Asp Asn Ser Gln Asn
                 85                  90                  95

Thr Leu Ser Leu Gln Met Ser Ser Leu Arg Ala Glu Asp Thr Ala Val
            100                 105                 110

Tyr Tyr Cys Ala Arg Gly Gly Gly Asp Phe Asp Phe Trp Gly Gln Gly
            115                 120                 125

Thr Leu Val Thr Val Ser Ser
            130                 135

<210> SEQ ID NO 100
<211> LENGTH: 387
<212> TYPE: DNA
<213> ORGANISM: Homo sapiens

<400> SEQUENCE: 100
atgaggctcc ctgctcagct tctcttcctc ctgctactct ggctcccaga tacctctgga      60 aaatagtga tgacgcagtc tccagccacc ctgtctgtgt ctccagggga agagccacc      120 ctctcctgta gggccagtca gagtgttagc ggcaactact tagcctggta ccagcggaga     180
cctggccagg ctcccaggct cctcatctat ggtgcatcca ccagggccac tggtatccca     240
gccaggttca gtggcagtgg gtctgggaca gagttcactc tcaccatcag cagcctgcag     300
tctgaagatt ttgcagttta ttactgtcag cagtatggta atggcctcc gctcactttc      360 ggcggaggga ccaaggtgga gatcaaa                                         387

<210> SEQ ID NO 101
<211> LENGTH: 129
<212> TYPE: PRT
<213> ORGANISM: Homo sapiens

<400> SEQUENCE: 101

Met Arg Leu Pro Ala Gln Leu Leu Phe Leu Leu Leu Leu Trp Leu Pro
  1               5                  10                  15

Asp Thr Ser Gly Lys Ile Val Met Thr Gln Ser Pro Ala Thr Leu Ser
             20                  25                  30

Val Ser Pro Gly Glu Arg Ala Thr Leu Ser Cys Arg Ala Ser Gln Ser
         35                  40                  45

Val Ser Gly Asn Tyr Leu Ala Trp Tyr Gln Arg Arg Pro Gly Gln Ala
     50                  55                  60

Pro Arg Leu Leu Ile Tyr Gly Ala Ser Thr Arg Ala Thr Gly Ile Pro
 65                  70                  75                  80

Ala Arg Phe Ser Gly Ser Gly Ser Gly Thr Glu Phe Thr Leu Thr Ile
             85                  90                  95

Ser Ser Leu Gln Ser Glu Asp Phe Ala Val Tyr Tyr Cys Gln Gln Tyr
            100                 105                 110

Gly Lys Trp Pro Pro Leu Thr Phe Gly Gly Gly Thr Lys Val Glu Ile
            115                 120                 125

Lys

<210> SEQ ID NO 102
<211> LENGTH: 441
<212> TYPE: DNA
<213> ORGANISM: Homo sapiens
```

-continued

<400> SEQUENCE: 102

```
atgaagcatc tgtggttctt ccttctggtc cactccatgg agttgggget gegetggggt      60
ttcctcgttg ctcttttaag aggtgtccag tgtcaggtgc agctggtgga gtctggggga    120
ggcgtggtcc agcctgggag gtccctgaga gtctcctgtg cagcgtctgg attcacette    180
agtaactatg gcatgcactg ggtccgccag gctccaggca aggggctgga gtgggtggca    240
gttatatggt atgatggaag taaaaaattc tatgcagact ccgtgaaggg ccgattcacc    300
atctccagag acaattccca gaacacgctg tctctgcaaa tgagcagcct gagagccgag    360
gacacggctg tgtattactg tgcgagaggc ggtgggggact ttgacttctg gggccaggga    420
accctggtca ccgtctcctc a                                              441
```

<210> SEQ ID NO 103
<211> LENGTH: 147
<212> TYPE: PRT
<213> ORGANISM: Homo sapiens

<400> SEQUENCE: 103

```
Met Lys His Leu Trp Phe Phe Leu Leu Val His Ser Met Glu Leu Gly
  1               5                  10                  15

Leu Arg Trp Gly Phe Leu Val Ala Leu Leu Arg Gly Val Gln Cys Gln
             20                  25                  30

Val Gln Leu Val Glu Ser Gly Gly Gly Val Val Gln Pro Gly Arg Ser
         35                  40                  45

Leu Arg Val Ser Cys Ala Ala Ser Gly Phe Thr Phe Ser Asn Tyr Gly
     50                  55                  60

Met His Trp Val Arg Gln Ala Pro Gly Lys Gly Leu Glu Trp Val Ala
 65                  70                  75                  80

Val Ile Trp Tyr Asp Gly Ser Lys Lys Phe Tyr Ala Asp Ser Val Lys
                 85                  90                  95

Gly Arg Phe Thr Ile Ser Arg Asp Asn Ser Gln Asn Thr Leu Ser Leu
            100                 105                 110

Gln Met Ser Ser Leu Arg Ala Glu Asp Thr Ala Val Tyr Tyr Cys Ala
        115                 120                 125

Arg Gly Gly Gly Asp Phe Asp Phe Trp Gly Gln Gly Thr Leu Val Thr
    130                 135                 140

Val Ser Ser
145
```

<210> SEQ ID NO 104
<211> LENGTH: 387
<212> TYPE: DNA
<213> ORGANISM: Homo sapiens

<400> SEQUENCE: 104

```
atggaaaccc cagctcagct tctcttcctc ctgctactct ggctcccaga taccactgga     60
aaaatagtga tgacgcagtc tccagccacc ctgtctgtgt ctccagggga aagagccacc    120
ctctcctgca gggccagtca gagtcttagc ggcagctact tagcctggta ccagcagaga    180
cctggccagg ctcccaggct cctcatctat ggtgcatcca ccagggccac tggtatccca    240
gccaggttca gtggcagtgg gtctgggaca gagttcactc tcaccatcag cagcctgcag    300
tctgaagatt ttgcagtttta ttactgtcag cagtataata gtggcctcc gctcactttc    360
ggcggaggga ccaaggtgga gatcaaa                                        387
```

<210> SEQ ID NO 105
<211> LENGTH: 129
<212> TYPE: PRT
<213> ORGANISM: Homo sapiens

<400> SEQUENCE: 105

Met Glu Thr Pro Ala Gln Leu Leu Phe Leu Leu Leu Trp Leu Pro
1               5                   10                  15

Asp Thr Thr Gly Lys Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Leu Ser Gly Ser Tyr Leu Ala Trp Tyr Gln Gln Arg Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Asn Lys Trp Pro Pro Leu Thr Phe Gly Gly Gly Thr Lys Val Glu Ile
        115                 120                 125

Lys

<210> SEQ ID NO 106
<211> LENGTH: 414
<212> TYPE: DNA
<213> ORGANISM: Homo sapiens

<400> SEQUENCE: 106
atgaagcacc tgtggttctt cctcctgctg gtggcagctc ccaaatgggt cctgtcacag    60
gtgcagctgc aggagtcggg cccaggactg gtgaagcctt cggagaccct gtccctcacc   120
tgcactgtct ctggtggctc catcagtggt tcctactgga gttggatccg gcagcccgcc   180
ggaaagggac tggagtggat tgggcgtatc cattccactg gaagaccgc ctacaacccc   240 tccctcaaga gtcgagtcat catgtcatta gacacgtcca agaacctgtt ctccctgaag   300
ctgacctctg tgaccgccgc ggacacggcc gtgtattact gtgcgagaga ttacgatttt   360
ctgactggtt actttgacta ctggggccag ggaaccctgg tcaccgtctc ctca         414

<210> SEQ ID NO 107
<211> LENGTH: 138
<212> TYPE: PRT
<213> ORGANISM: Homo sapiens

<400> SEQUENCE: 107

Met Lys His Leu Trp Phe Phe Leu Leu Leu Val Ala Ala Pro Lys Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Gly Ser Tyr Trp Ser Trp Ile Arg Gln Pro Ala Gly Lys Gly Leu
    50                  55                  60

Glu Trp Ile Gly Arg Ile His Ser Thr Gly Lys Thr Ala Tyr Asn Pro
65                  70                  75                  80

```
Ser Leu Lys Ser Arg Val Ile Met Ser Leu Asp Thr Ser Lys Asn Leu
                85                  90                  95

Phe Ser Leu Lys Leu Thr Ser Val Thr Ala Ala Asp Thr Ala Val Tyr
            100                 105                 110

Tyr Cys Ala Arg Asp Tyr Asp Phe Leu Thr Gly Tyr Phe Asp Tyr Trp
        115                 120                 125

Gly Gln Gly Thr Leu Val Thr Val Ser Ser
    130                 135
```

<210> SEQ ID NO 108
<211> LENGTH: 396
<212> TYPE: DNA
<213> ORGANISM: Homo sapiens

<400> SEQUENCE: 108

```
atgagggtcc ccgctcagct cctggggctg ctaatgctct gggtcccagg atccagtggg      60
gatgttgtga tgactcagtc tccactctcc ctgcccgtca cccttggaca gccggcctcc     120
atctcctgca ggtctagtca aagcctcgta tacggtgatg aaacaccta cttgaattgg      180
tttcaacaga ggccaggcca ctctccaagg cgcctaattt ataaggtttc taactgggac     240
tctggggtcc cagacagatt cagcggcagt gggtcaggca ctgatttcac actgaaaatc     300
agcagggtgg aggctgagga tgttggaatt tattactgca tgcaaggtac acactggcct     360
ccgacgttcg gccaagggac caggtggaa atcaaa                                396
```

<210> SEQ ID NO 109
<211> LENGTH: 132
<212> TYPE: PRT
<213> ORGANISM: Homo sapiens

<400> SEQUENCE: 109

```
Met Arg Val Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Tyr Gly Asp Gly Asn Thr Tyr Leu Asn Trp Phe Gln Gln Arg
    50                  55                  60

Pro Gly His Ser Pro Arg Arg Leu Ile Tyr Lys Val Ser Asn Trp Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Ile Tyr Tyr
            100                 105                 110

Cys Met Gln Gly Thr His Trp Pro Pro Thr Phe Gly Gln Gly Thr Arg
        115                 120                 125

Val Glu Ile Lys
    130
```

<210> SEQ ID NO 110
<211> LENGTH: 414
<212> TYPE: DNA
<213> ORGANISM: Homo sapiens

<400> SEQUENCE: 110

```
atgaagcacc tgtggttctt cctcctgctg gtggcagctc ccaaatgggt cctgtcccag      60
```

| | |
|---|---:|
| gtgcagctgc aggagtcggg cccaggactg gtgaagcctt cggagaccct gtccctcacc | 120 |
| tgcactgtct ctggtggctc catcagtggt tactactgga gttggatccg gcagcccgcc | 180 |
| ggtaagggac tggagtggat tgggcgtatc cataccactg gaagaccgc ctacaacccc | 240 |
| tccctcaaga gtcgagtcat catgtcagta gacacgtcca agaacctgtt ctccctgaag | 300 |
| ctgacctctg tgaccgccgc ggacacggcc gtgtattact gtgcgagaga ttacgatttt | 360 |
| ctgactggtt actttgacta ctggggccag ggaaccctgg tcaccgtctc ctca | 414 |

<210> SEQ ID NO 111
<211> LENGTH: 138
<212> TYPE: PRT
<213> ORGANISM: Homo sapiens

<400> SEQUENCE: 111

Met Lys His Leu Trp Phe Phe Leu Leu Leu Val Ala Ala Pro Lys Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Gly Tyr Tyr Trp Ser Trp Ile Arg Gln Pro Ala Gly Lys Gly Leu
    50                  55                  60

Glu Trp Ile Gly Arg Ile His Thr Thr Gly Lys Thr Ala Tyr Asn Pro
65                  70                  75                  80

Ser Leu Lys Ser Arg Val Ile Met Ser Val Asp Thr Ser Lys Asn Leu
                85                  90                  95

Phe Ser Leu Lys Leu Thr Ser Val Thr Ala Ala Asp Thr Ala Val Tyr
            100                 105                 110

Tyr Cys Ala Arg Asp Tyr Asp Phe Leu Thr Gly Tyr Phe Asp Tyr Trp
        115                 120                 125

Gly Gln Gly Thr Leu Val Thr Val Ser Ser
    130                 135

<210> SEQ ID NO 112
<211> LENGTH: 396
<212> TYPE: DNA
<213> ORGANISM: Homo sapiens

<400> SEQUENCE: 112

| | |
|---|---:|
| atgagggtcc ctgctcagct cctggggctg ctaatgctct gggtcccagg atccagtggg | 60 |
| gatgttgtga tgactcagtc tccactctcc ctgcccgtca cccttggaca gccggcctcc | 120 |
| atctcctgca ggtctagtca aagcctcgta tacagtgatg gaaacaccta cttgaattgg | 180 |
| tttcaacaga ggccaggcca ctctccaagg cgcctaattt ataaggtttc taactgggac | 240 |
| tctggggtcc cagacagatt cagcggcagt gggtcaggca ctgatttcac actgaaaatc | 300 |
| agcagggtgg aggctgagga tgttgggatt tattactgca tgcaaggtac acactggcct | 360 |
| ccgacgttcg gccaagggac cagggtggaa atcaaa | 396 |

<210> SEQ ID NO 113
<211> LENGTH: 132
<212> TYPE: PRT
<213> ORGANISM: Homo sapiens

<400> SEQUENCE: 113

Met Arg Val Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Tyr Ser Asp Gly Asn Thr Tyr Leu Asn Trp Phe Gln Gln Arg
    50                  55                  60

Pro Gly His Ser Pro Arg Arg Leu Ile Tyr Lys Val Ser Asn Trp Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Ile Tyr Tyr
            100                 105                 110

Cys Met Gln Gly Thr His Trp Pro Pro Thr Phe Gly Gln Gly Thr Arg
        115                 120                 125

Val Glu Ile Lys
    130

<210> SEQ ID NO 114
<211> LENGTH: 414
<212> TYPE: DNA
<213> ORGANISM: Homo sapiens

<400> SEQUENCE: 114
atgaagcatc tgtggttctt cctcctgctg gtggcagctc ccaaatgggt cctgtcccag      60
gtgcagctgc aggagtcggg cccaggactg gtgaagcctt cggagaccct gtccctcacc     120
tgcactgtct ctggtggctc catcagtggt tactactgga gttggatccg gcagcccgcc     180
ggtaagggac tggagtggat tggtcgtatc cacaccactg gaagaccgc ctacaattcc      240 tccctcaaga gtcgagtcat catgtcagta gacacgtcca agaacctgtt ctccctgaag     300
ctgacctctg tgaccgccgc ggacacggcc gtgtattact gtgcgagaga ttacgatttt     360
ttgactggtt actttgacta ctggggccag ggaaccctgg tcaccgtctc ctca           414

<210> SEQ ID NO 115
<211> LENGTH: 138
<212> TYPE: PRT
<213> ORGANISM: Homo sapiens

<400> SEQUENCE: 115

Met Lys His Leu Trp Phe Phe Leu Leu Leu Val Ala Ala Pro Lys Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Gly Tyr Tyr Trp Ser Trp Ile Arg Gln Pro Ala Gly Lys Gly Leu
    50                  55                  60

Glu Trp Ile Gly Arg Ile His Thr Thr Gly Lys Thr Ala Tyr Asn Ser
65                  70                  75                  80

Ser Leu Lys Ser Arg Val Ile Met Ser Val Asp Thr Ser Lys Asn Leu
                85                  90                  95

Phe Ser Leu Lys Leu Thr Ser Val Thr Ala Ala Asp Thr Ala Val Tyr
            100                 105                 110

Tyr Cys Ala Arg Asp Tyr Asp Phe Leu Thr Gly Tyr Phe Asp Tyr Trp
        115                 120                 125

```
Gly Gln Gly Thr Leu Val Thr Val Ser Ser
        130                 135
```

```
<210> SEQ ID NO 116
<211> LENGTH: 396
<212> TYPE: DNA
<213> ORGANISM: Homo sapiens

<400> SEQUENCE: 116
atgagggtcc ctgctcagct cctggggctg ctaatgctct gggtcccagg atccagtggg      60
gatgttgtga tgactcagtc tccactctcc ctgcccgtca cccttggaca gccggcctcc     120
atctcctgca ggtctagtca aagcctcgta tacagtgatg gaaacaccta cttgaattgg     180
tttcagcaga ggccaggcca atctccaagg cgcctaattt ataaggtttc taactgggac     240
tctggggtcc cagacagatt cagcggcagt ggggcaggca ctgatttcac actgaaaatc     300
agcagggtgg aggctgagga tgttggagtt tattactgca tgcaaggtac acactggcct     360
ccgacgttcg gccaagggac caggtggaa atcaaa                                396
```

```
<210> SEQ ID NO 117
<211> LENGTH: 132
<212> TYPE: PRT
<213> ORGANISM: Homo sapiens

<400> SEQUENCE: 117

Met Arg Val Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Tyr Ser Asp Gly Asn Thr Tyr Leu Asn Trp Phe Gln Gln Arg
    50                  55                  60

Pro Gly Gln Ser Pro Arg Arg Leu Ile Tyr Lys Val Ser Asn Trp Asp
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
            100                 105                 110

Cys Met Gln Gly Thr His Trp Pro Pro Thr Phe Gly Gln Gly Thr Arg
        115                 120                 125

Val Glu Ile Lys
    130
```

```
<210> SEQ ID NO 118
<211> LENGTH: 405
<212> TYPE: DNA
<213> ORGANISM: Homo sapiens

<400> SEQUENCE: 118
atggagttgg ggctgtgctg ggttttcctc gttgctcttt taagaggtgt ccagtgtcag      60
gtgcagctgg tggagtctgg gggaggcgtg gtccagcctg ggaggtccct gagagtctcc     120
tgtgcagcgt ctggattcac cttcagtaac tatggcatgc actgggtccg ccaggctcca     180 ggcaagggc tggagtgggt ggcagttata tggtatgatg gaagtaaaaa attctatgca      240
gactccgtga aggccgatt caccatctcc agagacaatt cccagaacac gctgtctctg      300
caaatgagca gcctgagagc cgaggacacg gctgtgtatt actgtgcgag aggcggtggg     360
```

```
gactttgact tctggggcca gggaaccctg gtcaccgtct cctca            405
```

<210> SEQ ID NO 119
<211> LENGTH: 135
<212> TYPE: PRT
<213> ORGANISM: Homo sapiens

<400> SEQUENCE: 119

| Met | Glu | Leu | Gly | Leu | Cys | Trp | Val | Phe | Leu | Val | Ala | Leu | Leu | Arg | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Val Gln Cys Gln Val Gln Leu Val Glu Ser Gly Gly Gly Val Val Gln
            20                      25                      30

Pro Gly Arg Ser Leu Arg Val Ser Cys Ala Ala Ser Gly Phe Thr Phe
        35                      40                      45

Ser Asn Tyr Gly Met His Trp Val Arg Gln Ala Pro Gly Lys Gly Leu
    50                      55                      60

Glu Trp Val Ala Val Ile Trp Tyr Asp Gly Ser Lys Lys Phe Tyr Ala
65                  70                      75                      80

Asp Ser Val Lys Gly Arg Phe Thr Ile Ser Arg Asp Asn Ser Gln Asn
                85                      90                      95

Thr Leu Ser Leu Gln Met Ser Ser Leu Arg Ala Glu Asp Thr Ala Val
            100                     105                     110

Tyr Tyr Cys Ala Arg Gly Gly Gly Asp Phe Asp Phe Trp Gly Gln Gly
        115                     120                     125

Thr Leu Val Thr Val Ser Ser
    130                     135

<210> SEQ ID NO 120
<211> LENGTH: 387
<212> TYPE: DNA
<213> ORGANISM: Homo sapiens

<400> SEQUENCE: 120

```
atggaaaccc cagctcagct tctcttcctc ctgctactct ggctcccaga tacctctgga    60
aaaatagtga tgacgcagtc tccagccacc ctgtctgtgt ctccagggga agagccacc    120
ctctcctgta gggccagtca gagtgttagc ggcaactact tagcctggta ccagcagaga    180
cctggccagg ctcccaggct cctcatctat ggtgcatcca ccagggccac tggcatccca    240
gccaggttca gtggcagtgg gtctgggaca gagttcactc tcaccatcag cagcctgcag    300
tctgaagatt ttgcagttta ttactgtcag caatatggta atggcctcc gctcactttc    360
ggcggaggga ccaaggtgga gatcaaa                                        387
```

<210> SEQ ID NO 121
<211> LENGTH: 129
<212> TYPE: PRT
<213> ORGANISM: Homo sapiens

<400> SEQUENCE: 121

Met Glu Thr Pro Ala Gln Leu Leu Phe Leu Leu Leu Leu Trp Leu Pro
1                   5                   10                  15

Asp Thr Ser Gly Lys Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Gly Asn Tyr Leu Ala Trp Tyr Gln Gln Arg Pro Gly Gln Ala
    50                  55                  60

```
Pro Arg Leu Leu Ile Tyr Gly Ala Ser Thr Arg Ala Thr Gly Ile Pro
 65                  70                  75                  80

Ala Arg Phe Ser Gly Ser Gly Ser Gly Thr Glu Phe Thr Leu Thr Ile
                 85                  90                  95

Ser Ser Leu Gln Ser Glu Asp Phe Ala Val Tyr Tyr Cys Gln Gln Tyr
            100                 105                 110

Gly Lys Trp Pro Pro Leu Thr Phe Gly Gly Gly Thr Lys Val Glu Ile
        115                 120                 125

Lys

<210> SEQ ID NO 122
<211> LENGTH: 405
<212> TYPE: DNA
<213> ORGANISM: Homo sapiens
<220> FEATURE:
<221> NAME/KEY: unsure
<222> LOCATION: (0)...(0)
<223> OTHER INFORMATION: n = A, T, C or G

<400> SEQUENCE: 122
atggagtttg ggctnagctg ggttttcctc gttgctcttt taagaggtgt ccagtgtcag    60
gtgcagctgg cggagtctgg gggaggcgtg gtccagcctg ggaggtccct gagactctcc   120
tgtgcagcgt ctggattcac cttcagtaac tatggcatgc actgggtccg ccaggctcca   180
ggcaaggggc tggagtgggt ggcaattata tggtatgatg gaagtaaaaa attctatgca   240
gactccgtga agggccgatt caccatctcc agagacaatt ccaacaacac gctgtatctg   300
cacgtgaaca gcctgagagt cgaggacacg gctgtgtatt actgtgcgag agggggcggt   360
gacattgact tctggggcca gggaaccctg gtcaccgtct cctca                  405

<210> SEQ ID NO 123
<211> LENGTH: 135
<212> TYPE: PRT
<213> ORGANISM: Homo sapiens

<400> SEQUENCE: 123

Met Glu Phe Gly Leu Ser Trp Val Phe Leu Val Ala Leu Leu Arg Gly
  1               5                  10                  15

Val Gln Cys Gln Val Gln Leu Ala Glu Ser Gly Gly Val Val Gln
             20                  25                  30

Pro Gly Arg Ser Leu Arg Leu Ser Cys Ala Ala Ser Gly Phe Thr Phe
             35                  40                  45

Ser Asn Tyr Gly Met His Trp Val Arg Gln Ala Pro Gly Lys Gly Leu
 50                  55                  60

Glu Trp Val Ala Ile Ile Trp Tyr Asp Gly Ser Lys Lys Phe Tyr Ala
 65                  70                  75                  80

Asp Ser Val Lys Gly Arg Phe Thr Ile Ser Arg Asp Asn Ser Asn Asn
                 85                  90                  95

Thr Leu Tyr Leu His Val Asn Ser Leu Arg Val Glu Asp Thr Ala Val
            100                 105                 110

Tyr Tyr Cys Ala Arg Gly Gly Gly Asp Ile Asp Phe Trp Gly Gln Gly
        115                 120                 125

Thr Leu Val Thr Val Ser Ser
        130                 135

<210> SEQ ID NO 124
<211> LENGTH: 384
```

```
<212> TYPE: DNA
<213> ORGANISM: Homo sapiens

<400> SEQUENCE: 124
atggaagccc cagcgcagct tctcttcctc ctgctactct ggctcccaga tatcactgga      60
aaaatagtga tgacgcagtc tccagccacc ctgtctgtgt ctccagggga agagccacc      120 ctctcctgca gggccagtca gagtgttagc agcaacttag cctggcacca gcagaaacct     180
ggccagcctc ccaggctcct catctatggt gcatcaacca gggccactgg tatcccagcc     240
aggttcagtg gcagtgggtc tgggacagag ttcactctca ccatcagcag cctgcagtct     300
gaagattttg cagtttatta ctgtcagcag tataataagt ggcctccggt caccttcggc     360
caagggacac gactggagat taaa                                            384

<210> SEQ ID NO 125
<211> LENGTH: 128
<212> TYPE: PRT
<213> ORGANISM: Homo sapiens

<400> SEQUENCE: 125

Met Glu Ala Pro Ala Gln Leu Leu Phe Leu Leu Leu Leu Trp Leu Pro
 1               5                  10                  15

Asp Ile Thr Gly Lys Ile Val Met Thr Gln Ser Pro Ala Thr Leu Ser
             20                  25                  30

Val Ser Pro Gly Glu Arg Ala Thr Leu Ser Cys Arg Ala Ser Gln Ser
         35                  40                  45

Val Ser Ser Asn Leu Ala Trp His Gln Gln Lys Pro Gly Gln Pro Pro
     50                  55                  60

Arg Leu Leu Ile Tyr Gly Ala Ser Thr Arg Ala Thr Gly Ile Pro Ala
 65                  70                  75                  80

Arg Phe Ser Gly Ser Gly Ser Gly Thr Glu Phe Thr Leu Thr Ile Ser
                 85                  90                  95

Ser Leu Gln Ser Glu Asp Phe Ala Val Tyr Tyr Cys Gln Gln Tyr Asn
            100                 105                 110

Lys Trp Pro Pro Val Thr Phe Gly Gln Gly Thr Arg Leu Glu Ile Lys
        115                 120                 125

<210> SEQ ID NO 126
<211> LENGTH: 414
<212> TYPE: DNA
<213> ORGANISM: Homo sapiens

<400> SEQUENCE: 126
atggagttgg ggcttagctg ggttttcctt gttgctatta taaaaggtgt ccagtgtcag     60
gtgcacctgg tggagtctgg gggaggcttg gtcaagcctg agggtccct gagactctcc     120 tgcgcagcct ctggattcac cttcattaac tactacatga cctggatccg ccaggctcca     180 gggaagggc tggagtgggt tcatacatt agtcttagtg gcagtaccat atactacgca      240
gactctgtga aggccgatt caccatctcc agggacaacg ccaagaactc actgtttctg     300
caaatgaaca gcctgagagc cgaggacacg gccgtgtatt actgtgcgag aagggcggct     360
acggtgacta cttttgacta ctggggccag ggaaccctgg tcaccgtctc ctca          414

<210> SEQ ID NO 127
<211> LENGTH: 138
<212> TYPE: PRT
<213> ORGANISM: Homo sapiens
```

```
<400> SEQUENCE: 127

Met Glu Leu Gly Leu Ser Trp Val Phe Leu Val Ala Ile Ile Lys Gly
 1               5                  10                  15

Val Gln Cys Gln Val His Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ile Asn Tyr Tyr Met Thr Trp Ile Arg Gln Ala Pro Gly Lys Gly Leu
     50                  55                  60

Glu Trp Val Ser Tyr Ile Ser Leu Ser Gly Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Phe Leu Gln Met Asn Ser Leu Arg Ala Glu Asp Thr Ala Val
            100                 105                 110

Tyr Tyr Cys Ala Arg Arg Ala Ala Thr Val Thr Thr Phe Asp Tyr Trp
        115                 120                 125

Gly Gln Gly Thr Leu Val Thr Val Ser Ser
    130                 135

<210> SEQ ID NO 128
<211> LENGTH: 381
<212> TYPE: DNA
<213> ORGANISM: Homo sapiens

<400> SEQUENCE: 128
atggaaactc cagcgcagct tctcttcctc ctgctactct ggctcccaga taccactgga      60
gaaatagtga tgacgcagtc tccagccacc ctgtctgtgt ctccagggga aagagccacc     120
ctctcctgca gggccagtca gagtgttagg agcaacttag cctggtccca gcagaagcct     180
ggccaggctc ccaggctcct catctatggt gcatccacca gggccactgg tatcccagcc     240
aggttcagtg gcagtgggtc tgggacagag ttcactctca ccatcagtag cctgcagtct     300
gaagattttg cagtttatta ctgtcagcag tataataact ggcctctcac tttcggcgga     360
gggaccaagg tggagatcaa a                                              381

<210> SEQ ID NO 129
<211> LENGTH: 127
<212> TYPE: PRT
<213> ORGANISM: Homo sapiens

<400> SEQUENCE: 129

Met Glu Thr Pro Ala Gln Leu Leu Phe Leu Leu Leu Trp Leu Pro
 1               5                  10                  15

Asp Thr Thr Gly Glu Ile Val Met Thr Gln Ser Pro Ala Thr Leu Ser
             20                  25                  30

Val Ser Pro Gly Glu Arg Ala Thr Leu Ser Cys Arg Ala Ser Gln Ser
         35                  40                  45

Val Arg Ser Asn Leu Ala Trp Ser Gln Gln Lys Pro Gly Gln Ala Pro
     50                  55                  60

Arg Leu Leu Ile Tyr Gly Ala Ser Thr Arg Ala Thr Gly Ile Pro Ala
 65                  70                  75                  80

Arg Phe Ser Gly Ser Gly Ser Gly Thr Glu Phe Thr Leu Thr Ile Ser
                 85                  90                  95

Ser Leu Gln Ser Glu Asp Phe Ala Val Tyr Tyr Cys Gln Gln Tyr Asn
            100                 105                 110
```

```
Asn Trp Pro Leu Thr Phe Gly Gly Gly Thr Lys Val Glu Ile Lys
        115                 120                 125

<210> SEQ ID NO 130
<211> LENGTH: 414
<212> TYPE: DNA
<213> ORGANISM: Homo sapiens

<400> SEQUENCE: 130
atggaattgg ggctgcgctg gggtttccat gttgctatta taaaaggtgt ccagtgtcag      60
gtgcagctgg tggagtctgg gggaggcttg gtcaagcctg agggtccct gagactctcc     120 tgtgcagcct ctggattcac cttcaatgtc tactacatga actggatccg ccaggctcca    180
gggaaggggc tggagtgggt ttcatacatt agtactagta gtagtgccat ttactacgca    240
gactctgtga agggccgatt caccatctcc agggacaatg ccaagaactc actgtatctg    300
caaatgaaca gcctgagagc cgaggacacg gccgtgtatt actgtgcgag aaggactgga    360
tctacgacgg tctttgacta ctggggccag ggaaccctgg tcaccgtctc ctca          414

<210> SEQ ID NO 131
<211> LENGTH: 138
<212> TYPE: PRT
<213> ORGANISM: Homo sapiens

<400> SEQUENCE: 131

Met Glu Leu Gly Leu Arg Trp Gly Phe His Val Ala Ile Ile Lys Gly
 1               5                  10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Asn Val Tyr Tyr Met Asn Trp Ile Arg Gln Ala Pro Gly Lys Gly Leu
    50                  55                  60

Glu Trp Val Ser Tyr Ile Ser Thr Ser Ser Ser Ala Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Arg Thr Gly Ser Thr Thr Val Phe Asp Tyr Trp
        115                 120                 125

Gly Gln Gly Thr Leu Val Thr Val Ser Ser
    130                 135

<210> SEQ ID NO 132
<211> LENGTH: 402
<212> TYPE: DNA
<213> ORGANISM: Homo sapiens

<400> SEQUENCE: 132
atggaaaccc cagcgcagct tatggaaacc ccagcgcagc ttctcttcct cctgctactc      60
tggctcccag ataccactgg agaaatagta ttgacgcagt ctccagccac cctgtctgtg    120
tctccagggg aaagagccac cctctcctgc agggccagtc agagtattaa caacaactta    180
gcctggtacc agcagaaacc tggccaggct cccaggctcc tcatctatgg tgcatccacc    240
agggccactg gtatcccagc caagttcagt ggcagtgggt ctgggacaga attcactctc    300
```

```
accatcagca gcctgcagtc tgaaaatttt gcagtttatt actgtcagca gtataataag    360
tggccgctca ctttcggcgg agggaccaag gtggagatca aa                        402
```

<210> SEQ ID NO 133
<211> LENGTH: 134
<212> TYPE: PRT
<213> ORGANISM: Homo sapiens

<400> SEQUENCE: 133

| | | | | | | | | | | | | | | |
|---|---|---|---|---|---|---|---|---|---|---|---|---|---|---|
| Met | Glu | Thr | Pro | Ala | Gln | Leu | Met | Glu | Thr | Pro | Ala | Gln | Leu | Phe |
| 1 | | | | 5 | | | | | 10 | | | | | 15 |
| Leu | Leu | Leu | Leu | Trp | Leu | Pro | Asp | Thr | Thr | Gly | Glu | Ile | Val | Leu | Thr |
| | | | 20 | | | | | 25 | | | | | 30 | | |
| Gln | Ser | Pro | Ala | Thr | Leu | Ser | Val | Ser | Pro | Gly | Glu | Arg | Ala | Thr | Leu |
| | | 35 | | | | | 40 | | | | | 45 | | | |
| Ser | Cys | Arg | Ala | Ser | Gln | Ser | Ile | Asn | Asn | Asn | Leu | Ala | Trp | Tyr | Gln |
| | 50 | | | | | 55 | | | | | 60 | | | | |
| Gln | Lys | Pro | Gly | Gln | Ala | Pro | Arg | Leu | Leu | Ile | Tyr | Gly | Ala | Ser | Thr |
| 65 | | | | | 70 | | | | | 75 | | | | | 80 |
| Arg | Ala | Thr | Gly | Ile | Pro | Ala | Lys | Phe | Ser | Gly | Ser | Gly | Ser | Gly | Thr |
| | | | | 85 | | | | | 90 | | | | | 95 | |
| Glu | Phe | Thr | Leu | Thr | Ile | Ser | Ser | Leu | Gln | Ser | Glu | Asn | Phe | Ala | Val |
| | | | 100 | | | | | 105 | | | | | 110 | | |
| Tyr | Tyr | Cys | Gln | Gln | Tyr | Asn | Lys | Trp | Pro | Leu | Thr | Phe | Gly | Gly | Gly |
| | | 115 | | | | | 120 | | | | | 125 | | | |
| Thr | Lys | Val | Glu | Ile | Lys |
| | 130 |

<210> SEQ ID NO 134
<211> LENGTH: 414
<212> TYPE: DNA
<213> ORGANISM: Homo sapiens

<400> SEQUENCE: 134

```
atggagttgg ggctgtgctg ggttttcctt gttgctatta taaaaggtgt cctgtgtcag    60
gtgcagctgg tggagtctgg gggagacttg gtcaagcctg agggtccct gagactctcc    120 tgtgcagcct ctggattcag cttcagtggc tactacttga gctggatccg ccaggctcca    180 gggaagggc tggagtgggt tcatacatt agtctaagtg gtagtttcat aaagtatgca    240
gactctgtga aggccgatt caccatctcc agggacaacg ccaagaaaac actgcatctg    300
caaatgaaca gcctgagagc cgaggacacg gccgtgtatt actgtgcgag aaggactgga    360
actacgacgg tctttgacta ctggggccag ggaaccctgg tcaccgtctc ctca         414
```

<210> SEQ ID NO 135
<211> LENGTH: 138
<212> TYPE: PRT
<213> ORGANISM: Homo sapiens

<400> SEQUENCE: 135

| | | | | | | | | | | | | | | |
|---|---|---|---|---|---|---|---|---|---|---|---|---|---|---|
| Met | Glu | Leu | Gly | Leu | Cys | Trp | Val | Phe | Leu | Val | Ala | Ile | Ile | Lys | Gly |
| 1 | | | | 5 | | | | | 10 | | | | | 15 | |
| Val | Leu | Cys | Gln | Val | Gln | Leu | Val | Glu | Ser | Gly | Gly | Asp | Leu | Val | Lys |
| | | | 20 | | | | | 25 | | | | | 30 | | |
| Pro | Gly | Gly | Ser | Leu | Arg | Leu | Ser | Cys | Ala | Ala | Ser | Gly | Phe | Ser | Phe |
| | | 35 | | | | | 40 | | | | | 45 | | | |
| Ser | Gly | Tyr | Tyr | Leu | Ser | Trp | Ile | Arg | Gln | Ala | Pro | Gly | Lys | Gly | Leu |

```
                50                  55                  60
Glu Trp Val Ser Tyr Ile Ser Leu Ser Gly Ser Phe Ile Lys Tyr Ala
 65                  70                  75                  80

Asp Ser Val Lys Gly Arg Phe Thr Ile Ser Arg Asp Asn Ala Lys Lys
                 85                  90                  95

Thr Leu His Leu Gln Met Asn Ser Leu Arg Ala Glu Asp Thr Ala Val
            100                 105                 110

Tyr Tyr Cys Ala Arg Arg Thr Gly Thr Thr Val Phe Asp Tyr Trp
        115                 120                 125

Gly Gln Gly Thr Leu Val Thr Val Ser Ser
        130                 135
```

<210> SEQ ID NO 136
<211> LENGTH: 381
<212> TYPE: DNA
<213> ORGANISM: Homo sapiens

<400> SEQUENCE: 136

```
atggatoccc cagcgcagct tctcttcctc ctgctactct ggctcccaga taccgctgga      60
gaagtagtga tgacgcagtc tccagccacc ctgtctgtgt ctccagggga agagccacc     120
ctctcctgca gggccagtca gagtgttaac agcaacttag cctggtacca gcagagacct    180
ggccaggctc ccaggctcct catctatggt gcatccacca gggtcactgg tatcccagcc    240
aggttcagcg gcagtgggtc tgggacagag ttcactctca ccatcagcag cctgcagtct    300
gaagattttg cagtttatta ctgtcagcag tataataact ggccgctcac tttcggcgga    360
gggaccaagg tggagatcaa a                                              381
```

<210> SEQ ID NO 137
<211> LENGTH: 127
<212> TYPE: PRT
<213> ORGANISM: Homo sapiens

<400> SEQUENCE: 137

```
Met Asp Thr Pro Ala Gln Leu Leu Phe Leu Leu Leu Trp Leu Pro
  1               5                  10                  15

Asp Thr Ala Gly Glu Val Val Met Thr Gln Ser Pro Ala Thr Leu Ser
             20                  25                  30

Val Ser Pro Gly Glu Arg Ala Thr Leu Ser Cys Arg Ala Ser Gln Ser
         35                  40                  45

Val Asn Ser Asn Leu Ala Trp Tyr Gln Gln Arg Pro Gly Gln Ala Pro
 50                  55                  60

Arg Leu Leu Ile Tyr Gly Ala Ser Thr Arg Val Thr Gly Ile Pro Ala
 65                  70                  75                  80

Arg Phe Ser Gly Ser Gly Ser Gly Thr Glu Phe Thr Leu Thr Ile Ser
                 85                  90                  95

Ser Leu Gln Ser Glu Asp Phe Ala Val Tyr Tyr Cys Gln Gln Tyr Asn
            100                 105                 110

Asn Trp Pro Leu Thr Phe Gly Gly Gly Thr Lys Val Glu Ile Lys
        115                 120                 125
```

<210> SEQ ID NO 138
<211> LENGTH: 405
<212> TYPE: DNA
<213> ORGANISM: Homo sapiens

<400> SEQUENCE: 138

```
atggagttgg ggctgtgctg ggttttcctc gttgctcttt taagaggtgt ccagtgtcag    60
gtacaactgg tggagtctgg gggaggcgtg gtccagcctg ggaggtccct gagactctcc   120
tgtgcagcgt ctggattcac cttcagtaat tatggcatgc actgggtccg ccaggctcca   180 ggcaagggc tggagtgggt ggcagttata tggtatgatg gaagtaagaa attctatgca    240
gactccgtga agggccgatt caccatctcc agagacaatt ttgagaaaac gctgtatctg   300
caaatgaaca gcctgagagc cgaggacacg gctgtgtatt actgtgcgag agggggcggt   360
gactttgact actggggcca gggaaccctg gtcaccgtct cctca                  405
```

<210> SEQ ID NO 139
<211> LENGTH: 135
<212> TYPE: PRT
<213> ORGANISM: Homo sapiens

<400> SEQUENCE: 139

```
Met Glu Leu Gly Leu Cys Trp Val Phe Leu Val Ala Leu Leu Arg Gly
 1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Val Ile Trp Tyr Asp Gly Ser Lys Lys Phe Tyr Ala
65                  70                  75                  80

Asp Ser Val Lys Gly Arg Phe Thr Ile Ser Arg Asp Asn Phe Glu Lys
                85                  90                  95

Thr Leu Tyr Leu Gln Met Asn Ser Leu Arg Ala Glu Asp Thr Ala Val
            100                 105                 110

Tyr Tyr Cys Ala Arg Gly Gly Gly Asp Phe Asp Tyr Trp Gly Gln Gly
        115                 120                 125

Thr Leu Val Thr Val Ser Ser
    130                 135
```

<210> SEQ ID NO 140
<211> LENGTH: 387
<212> TYPE: DNA
<213> ORGANISM: Homo sapiens

<400> SEQUENCE: 140

```
atggaagccc cagcgcagct tctcttcctc ctgctactct ggctcccaga taccactgga    60
gaaatagtga tgacgcagtc tccagccacc ctgtctgtgt ctccagggga aagagccacc   120
ctctcctgca gggccagtca gagtcttagc ggcagctact tagcctggta ccagcagaaa   180
cctggccagg ctcccaggct cctcatctat agtgcatcca ccagggccac tggtatccca   240
gccaggttca gtggcagtgg gtctgggaca gagttcactc tcaccatcag cagcctgcag   300
tctgaagatt ttgcagttta ttactgtcag cagtataata actggcctcc gctcactttc   360
ggcggaggga ccaaggtgga gatcaaa                                      387
```

<210> SEQ ID NO 141
<211> LENGTH: 129
<212> TYPE: PRT
<213> ORGANISM: Homo sapiens

<400> SEQUENCE: 141

-continued

Met Glu Ala Pro Ala Gln Leu Phe Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Leu Ser Gly Ser Tyr Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
                100                 105                 110

Asn Asn Trp Pro Pro Leu Thr Phe Gly Gly Gly Thr Lys Val Glu Ile
            115                 120                 125

Lys

<210> SEQ ID NO 142
<211> LENGTH: 46
<212> TYPE: PRT
<213> ORGANISM: Homo sapiens

<400> SEQUENCE: 142

Val Ser Ser Val Gln Thr Pro His Leu Pro Thr His Ala Asp Ser Gln
1               5                   10                  15

Thr Pro Ser Ala Gly Thr Asp Thr Gln Thr Phe Ser Gly Ser Ala Ala
            20                  25                  30

Asn Ala Lys Leu Asn Pro Thr Pro Gly Ser Asn Ala Ile Ser
            35                  40                  45

<210> SEQ ID NO 143
<211> LENGTH: 46
<212> TYPE: PRT
<213> ORGANISM: Homo sapiens

<400> SEQUENCE: 143

Val Ser Ser Ala Leu Thr Pro His Leu Pro Thr His Ala Asp Ser Gln
1               5                   10                  15

Thr Pro Ser Thr Gly Thr Asp Thr Gln Thr Pro Ser Gly Ser Ala Ala
            20                  25                  30

Asn Thr Thr Leu Ser Pro Thr Pro Arg Ser Asn Asp Ile Ser
            35                  40                  45

<210> SEQ ID NO 144
<211> LENGTH: 19
<212> TYPE: PRT
<213> ORGANISM: Homo sapiens

<400> SEQUENCE: 144

Val Ser Ser Val Gln Thr Pro His Leu Pro Thr His Ala Asp Ser Gln
1               5                   10                  15

Thr Pro Cys

<210> SEQ ID NO 145
<211> LENGTH: 20
<212> TYPE: PRT
<213> ORGANISM: Homo sapiens -continued

```
<400> SEQUENCE: 145

Val Ser Ser Val Gln Thr Pro His Leu Pro Thr His Ala Asp Ser Gln
1               5                   10                  15

Thr Pro Ser Ala
            20

<210> SEQ ID NO 146
<211> LENGTH: 20
<212> TYPE: PRT
<213> ORGANISM: Homo sapiens

<400> SEQUENCE: 146

Ala Asp Ser Gln Thr Pro Ser Ala Gly Thr Asp Thr Gln Thr Phe Ser
1               5                   10                  15

Gly Ser Ala Ala
            20

<210> SEQ ID NO 147
<211> LENGTH: 20
<212> TYPE: PRT
<213> ORGANISM: Homo sapiens

<400> SEQUENCE: 147

Phe Ser Gly Ser Ala Ala Asn Ala Lys Leu Asn Pro Thr Pro Gly Ser
1               5                   10                  15

Asn Ala Ile Ser
            20
```

US 7,265,212 B2

ANTI-CD45RB ANTIBODIES

RELATED APPLICATIONS

This application claims priority to U.S. Provisional Application No. 60/337,276 filed on Dec. 3, 2001.

FIELD OF THE INVENTION

The present invention relates to novel fully human antibodies which specifically recognize the RB isoform of CD45. The invention further relates to methods of using the antibodies to treat autoimmune diseases and transplant rejection.

BACKGROUND OF THE INVENTION

The prevention of cell, tissue or organ transplant rejection and the treatment of autoimmune diseases require either the induction or the restoration of immunological tolerance respectively. In the thymus, tolerance is established through the deletion of auto-reactive T lymphocytes during maturation. In the periphery, tolerance is maintained through several mechanisms including the deletion of auto-reactive T cells, the induction of T cell anergy, or the failure to respond to antigen known as T cell indifference. In the latter case, the autoantigen is present and the T cells are able to respond but the T cells lack the appropriate co-stimulatory signals to respond. Overall, the breakdown of tolerance associated with autoimmune disorders and the lack of tolerance for allografts associated with transplant rejection, are thought to be primarily T-cell mediated immune responses.

CD45 is a transmembrane protein tyrosine phosphatase expressed primarily on cells of hematopoietic origin and is thought to plays a critical role in regulating T-cell activation. CD45 exists as several different isoforms that are generated by the alternate splicing of exons 4-6, also known as A, B and C, from a single primary transcript. A total of 8 isoforms have been described including CD45RO, CD45RA, CD45RB, CD45RC, CD45RAB, CD45RBC, CD45RAC and CD45RABC. These isoforms have different extracellular domains but they have identical cytoplasmic domains including the protein tyrosine phosphatase domains. In humans, naïve helper T-cells and memory T-cells express predominately CD45RA and CD45RO, respectively. The expression of CD45RB appears to be higher on naïve helper T-cells and appears to be down-regulated as the cells become activated.

The literature supports a protective role for anti-CD45RB antibodies in transplant rejection (Zhang et al., Transplant Proc. 27:389 (1995), Lazarovits et al. Nature, 380:717 (1996)). Lazarovits et al. demonstrated the ability of MB23G2, a rat anti-mouse CD45RB antibody, to prevent the rejection of murine renal allografts. This study also demonstrated that MB4B4, another rat anti-mouse CD45RB antibody, was ineffective at preventing renal allograft rejection indicating that not all anti-CD45RB antibodies will show therapeutic efficacy. The antibody MB23G2 has also shown efficacy in promoting the long term survival of pancreatic islet cell allografts (Basadonna et al., PNAS 95:3821 (1998)). The specific mechanism of tolerance induction of the anti-CD45RB antibodies is currently unknown. Tolerance induction by anti-CD45RB antibodies has been correlated with increased tyrosine phosphatase activity (Lazarovits et al., Kidney Int. 55:1303 (1999)). Tolerance may also arise through a specific deletion of alloreactive peripheral blood mononuclear cells or through the induction of T regulatory cells.

Poppema and Lazarovits previously isolated and characterized a murine IgG1 antibody which is directed against human CD45RB, identified as antibody 6G3 (Lazarovits, et al. U.S. Pat. No. 6,024,957, herein incorporated by reference). However, this is a mouse antibody and as such may be highly immunogenic in humans. 6G3, and other antibodies specific for CD45RB, have been shown to prolong renal allograft survival or pancreatic islet cell allografts in cynomolgous monkeys and mice respectively. Functionally, 6G3, and other antibodies specific for CD45RB, will downregulate the expression of CD45RB and L-selectin on peripheral blood mononuclear cells. Interestingly, MB23G2, but not MB4B4, also down-regulates the expression of CD45RB on peripheral blood mononuclear cells supporting the notion that CD45RB down-regulation could be a surrogate marker to identify other anti-CD45RB antibodies capable of transplant protection (Basadonna et al., PNAS 95:3821 (1998)).

Lazarovits, et al. U.S. Pat. No. 6,106,834 identified a method of identifying ligands (antibodies) specific for CD45RB, CD45RO using an immunoaffinity column (ie: with MT3 or 6G3 antibodies). The immunoaffinity column is used to identify an antigen-containing binding partner. Then the binding partner is used to select cross-reactive ligands. However, specific antibodies which recognize the CD45RB isotype were not identified.

Lazarovits, et al. U.S. Pat. No. 6,024,957 describe a method of humanizing the previously identified MT3, or 6G3 antibodies which would be less likely to be recognized by the immune system as foreign. However, these antibodies are still not fully human and may induce a reaction when introduced into the human immune system.

Thus, anti-CD45RB-specific antibodies which are specific for a variety of antigenic determinants of CD45RB are needed which do not recognize the other isoforms of the CD45 antigen. To be of use in humans, these antibodies should be fully human and display similar functional characteristics as 6G3. In addition, large scale concentrations of the antibodies should be producible with a minimum of labor.

SUMMARY OF THE INVENTION

Fully human antibodies which recognize the RB isoform of CD45 were produced. These antibodies may be used to block undesirable reactions in patients with transplant rejection and/or autoimmune diseases.

One embodiment of the invention is antibodies which recognize the RB isoform of CD45. Preferably, these antibodies are fully human antibodies and may be used to block undesirable reactions in patients with transplant rejection and/or autoimmune diseases.

Another embodiment of the invention is antibodies which recognize the RB isoform of CD45, but also have CDRs comprising the sequences shown in FIGS. 1 and 2. The antibodies may comprise a heavy chain amino acid sequence selected from the group consisting of SEQ ID Nos: 55, 59, 63, 67, 71, 75, 79, 83, 87, 91, 95, 99, 103, 107, 111, 115, 119, 123, 127, 131, 135 and 139 and/or a light chain amino acid sequence selected from the group consisting of SEQ ID Nos: 57, 61, 65, 69, 73, 77, 81, 85, 89, 93, 97, 101, 105, 109, 113, 117, 121, 125, 129, 133, 137 and 141. A further embodiment is an isolated monoclonal antibody that binds to CD45RB and comprises a heavy chain amino acid sequence, or a fragment(s) thereof, selected from the group consisting of SEQ ID Nos: 55, 59, 63, 67, 71, 75, 79, 83, 87, 91, 95, 99, 103, 107, 111, 115, 119, 123, 127, 131, 135 and 139, wherein said antibody is conjugated to a therapeutic agent. A further embodiment is an isolated monoclonal antibody that binds to CD45RB and comprises a heavy chain amino acid sequence, or a fragment(s) thereof, selected from the group consisting of SEQ ID Nos: 55, 59, 63, 67, 71, 75, 79, 83, 87, 91, 95, 99, 103, 107, 111, 115, 119, 123, 127, 131, 135 and 139, wherein said antibody is conjugated to a therapeutic agent, wherein the therapeutic agent is toxin. A further embodiment is an isolated monoclonal antibody that binds to CD45RB and comprises a heavy chain amino acid sequence, or a fragment(s) thereof, selected from the group consisting of SEQ ID Nos: 55, 59, 63, 67, 71, 75, 79, 83, 87, 91, 95, 99, 103, 107, 111, 115, 119, 123, 127, 131, 135 and 139, wherein said antibody is conjugated to a therapeutic agent, wherein the therapeutic agent is a radioisotope.

A purified fully human antibody with at least one complementarity-determining region (CDR) selected from the group consisting of those shown in FIGS. 1 and 2.

Yet another embodiment is a method for treating or preventing cell, tissue or organ transplant rejection in a mammal, comprising administering to said mammal at least one fully human antibody comprising at least one CDR selected from the group consisting of those shown in FIGS. 1 and 2.

Still another embodiment is a method for treating autoimmune disease in a mammal, comprising administering to said mammal at least one fully human antibody with at least one CDR selected from the group consisting of those shown in FIGS. 1 and 2.

BRIEF DESCRIPTION OF THE DRAWINGS

FIGS. 1A-1B demonstrates an alignment of variable gamma chains and gene families of the anti-CD45RB monoclonal antibodies generated according to the invention. The amino acid alignments are of Vgamma sequences without leaders and their respective germline sequences. Identity with germline sequences is indicated by a '–', somatic hypermutations are shown by the new amino acid, insertions are shown as '#' and deletions are shown as 'x'.

FIGS. 2A-2B demonstrates an alignment of variable kappa chains and gene families of anti-CD45RB monoclonal antibodies generated according to the invention. The amino acid alignments are of Vkappa sequences without leaders and their respective germline sequences. Identity with germline sequences is indicated by a '–', somatic hypermutations are shown by the new amino acid, insertions are shown as '#' and deletions are shown as 'x'.

FIG. 4 shows FACS analysis of the binding of the mouse monoclonal antibody 6G3 to naïve and activated human T cells (FIG. 4A) and naïve and activated macaque T cells (FIG. 4B).

FIG. 5 shows FACS analysis of the binding of the human antibody sc026 to naïve and activated human (FIG. 5A) and naïve and activated macaque T cells (FIG. 5B).

FIG. 6 shows FACS analysis of the binding of the human antibody sc439 to naïve and activated human (FIG. 6A) and naïve and activated macaque T cells (FIG. 6B).

FIG. 7 shows FACS analysis of the binding of the human antibody sc446 to naïve and activated human (FIG. 7A) and naïve and activated macaque T cells (FIG. 7B).

FIG. 8 shows FACS analysis of the binding of the human antibody sc487 to naïve and activated human (FIG. 8A) and naïve and activated macaque T cells (FIG. 8B).

FIG. 9 shows FACS analysis of the binding of the human antibody sc502 to naïve and activated human (FIG. 9A) and naïve and activated macaque T cells (FIG. 9B).

FIG. 10 shows FACS analysis of the binding of the human antibody sc606 to naïve and activated human (FIG. 10A) and naïve and activated macaque T cells (FIG. 10B).

FIG. 11 shows FACS analysis of the binding of the human antibody sc713 to naïve and activated human (FIG. 11A) and naïve and activated macaque T cells (FIG. 11B).

FIG. 12 shows FACS analysis of the binding of the human antibody sc636 to naïve and activated human (FIG. 12A) and naïve and activated macaque T cells (FIG. 12B).

FIG. 13 shows FACS analysis of the binding of the human antibody sc648 to naïve and activated human (FIG. 13A) and naïve and activated macaque T cells (FIG. 13B).

FIG. 14 shows FACS analysis of the binding of the human antibody sc324 to naïve and activated human (FIG. 14A) and naïve and activated macaque T cells (FIG. 14B).

FIG. 15 show FACS analysis of the binding of the human antibody sc475 to naïve and activated human (FIG. 15A) and naïve and activated macaque T cells (FIG. 15B).

FIG. 16 show FACS analysis of the binding of the human antibody sc569 to naïve and activated human (FIG. 16A) and naïve and activated macaque T cells (FIG. 16B).

DETAILED DESCRIPTION

Figure 3:
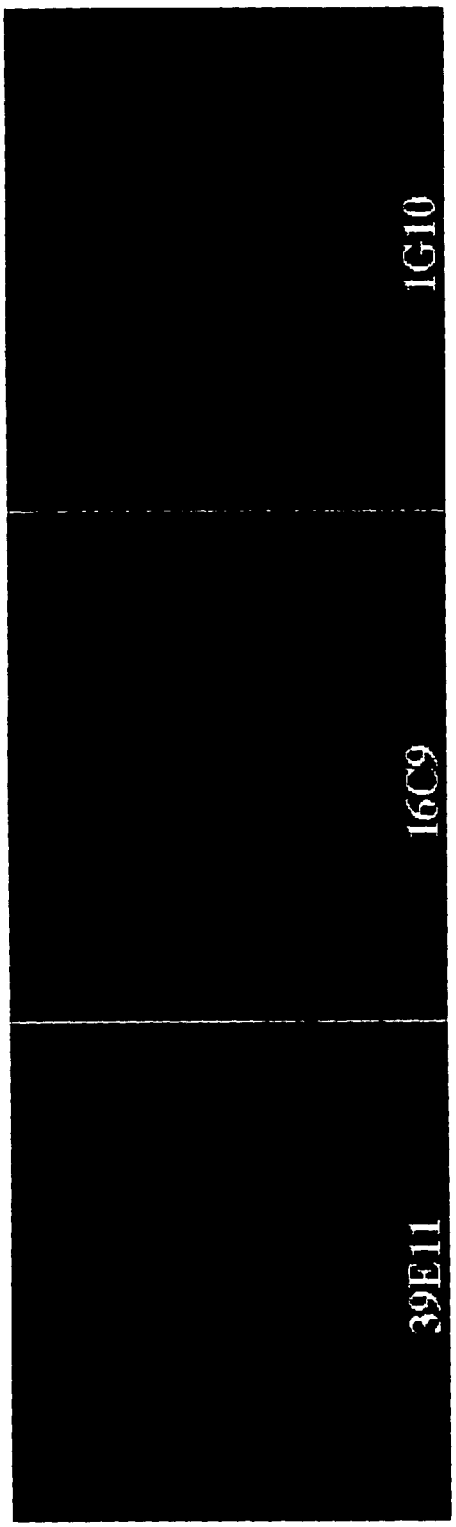
FIG. 3 shows the native binding of antibodies 39E11 (sc324), 16C9 (sc009), and 1G10 (sc026) to CHO cells which were transiently transfected with CD45RB.
Figure 17A:
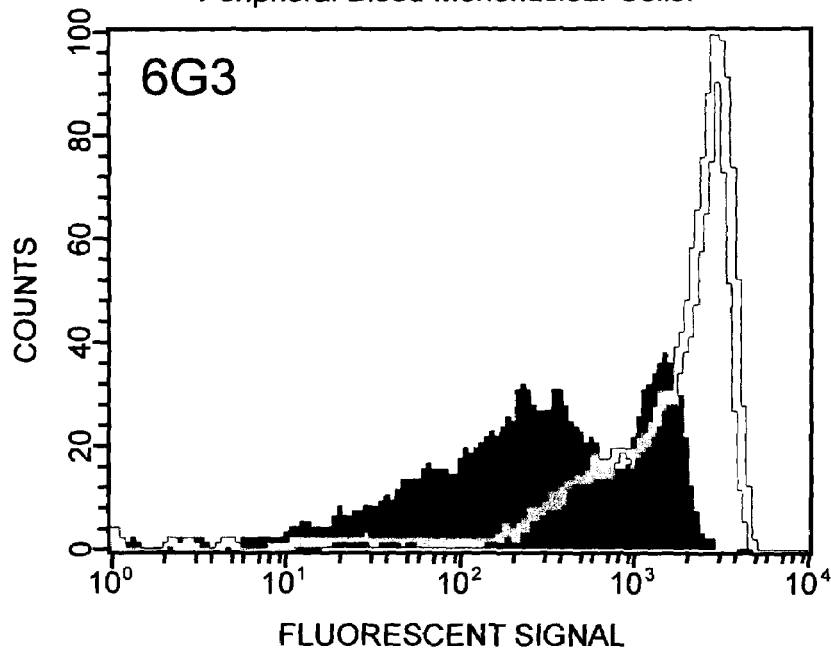
FIG. 17 shows the down-regulation of CD45RB on peripheral blood mononuclear cells (PBMCs) by the mouse monoclonal antibody 6G3 and the human monoclonal antibodies 1G101 (sc026), 325, 413, 487, and 502.
Figure 17B:
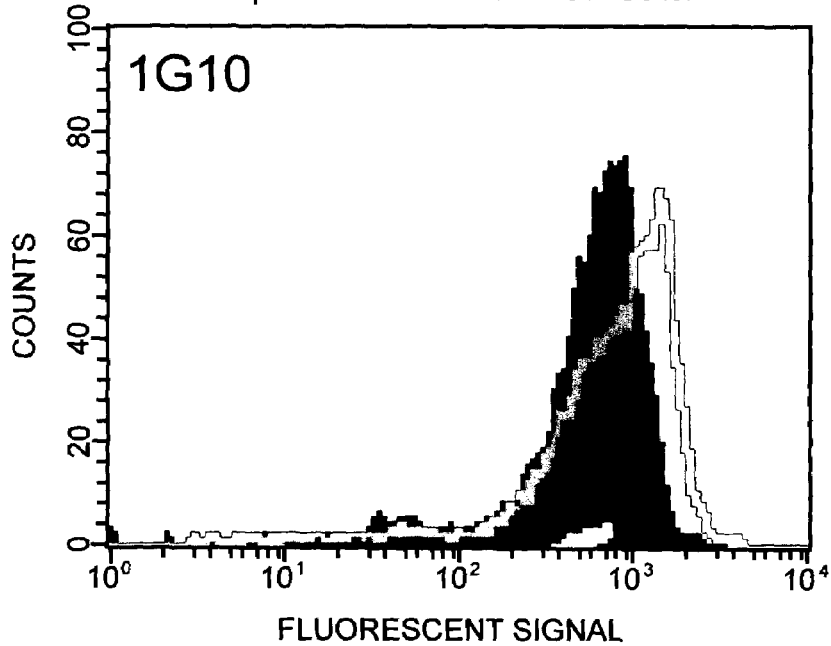
Figure 17C:
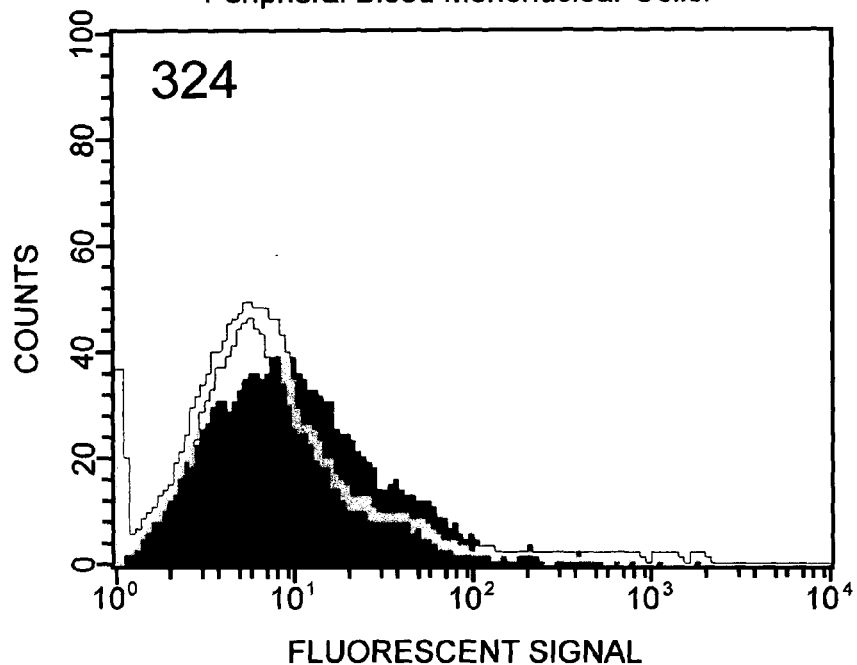
Figure 17D:
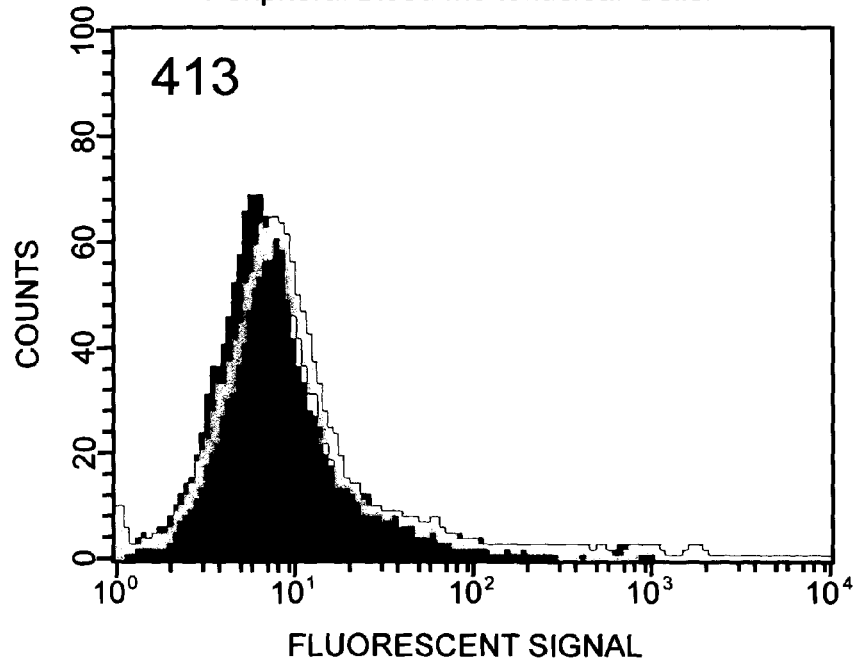
Figure 17E:
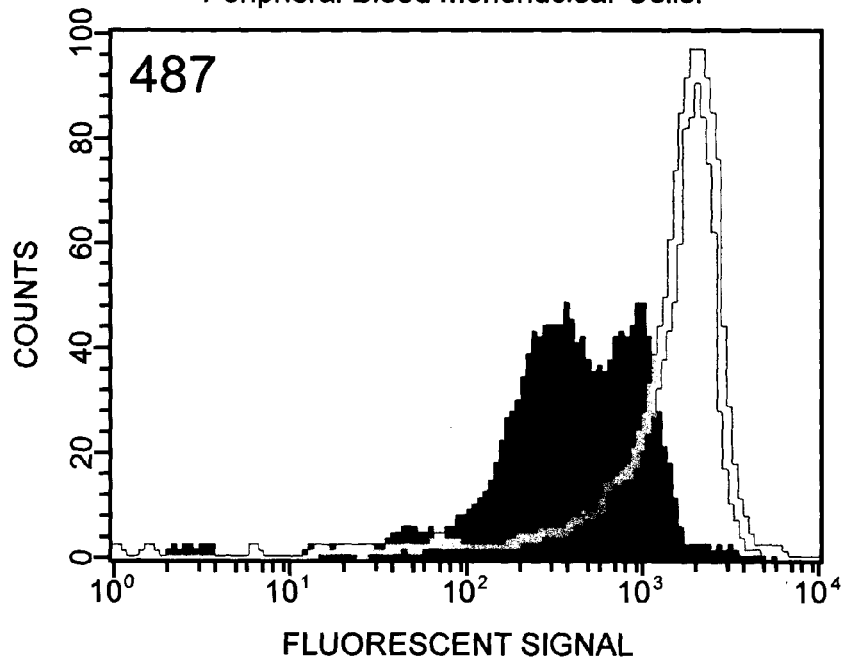
Figure 17F:
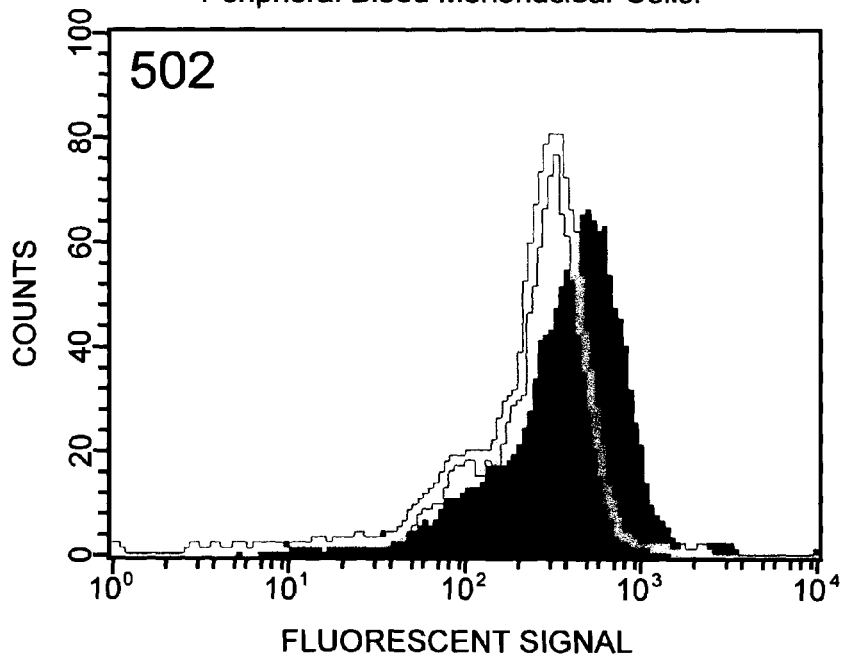
Figure 18A:
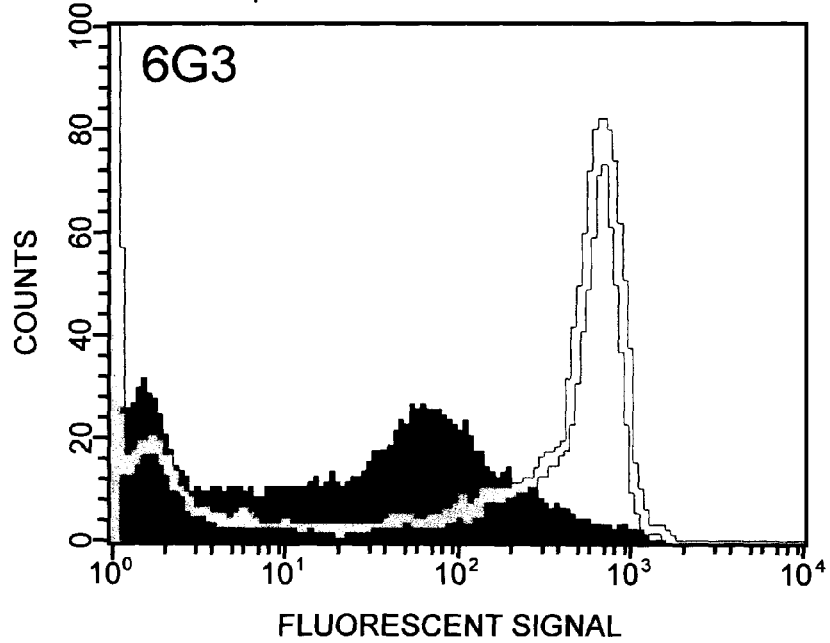
FIG. 18 shows the down-regulation of L-Selectin on peripheral blood mononuclear cells (PBMCs) by the mouse monoclonal antibody 6G3 and the human antibodies 1G10 (sc026), 325, 413, 487, and 502.
Figure 18B:
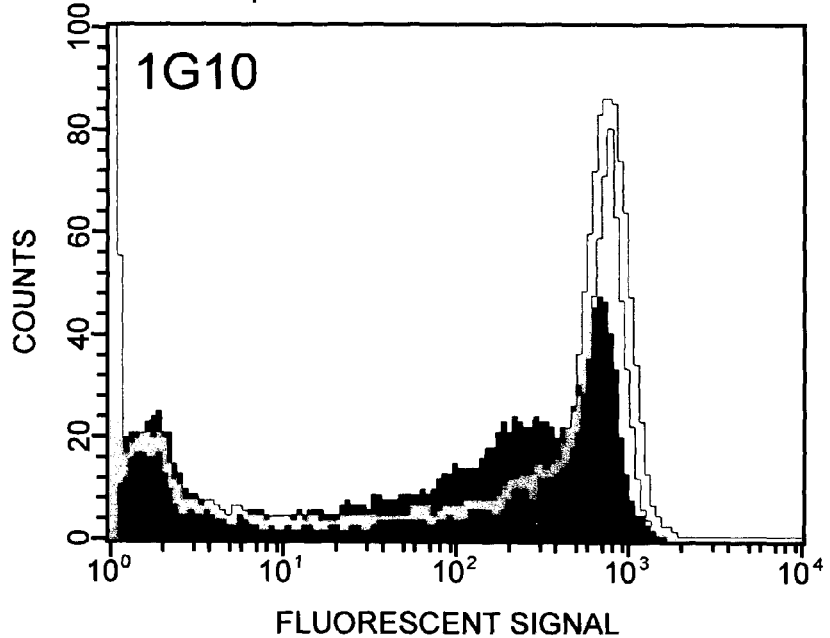
Figure 18C:
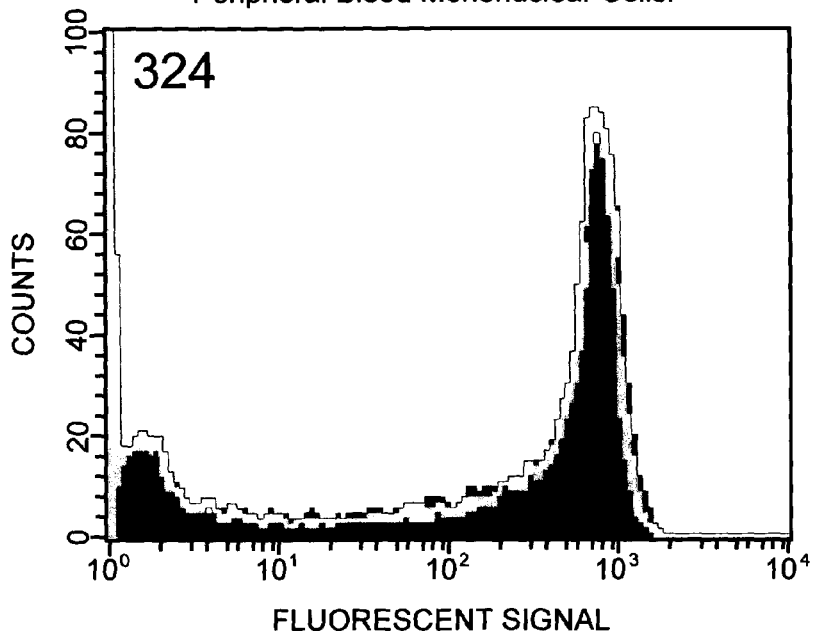
Figure 18D:
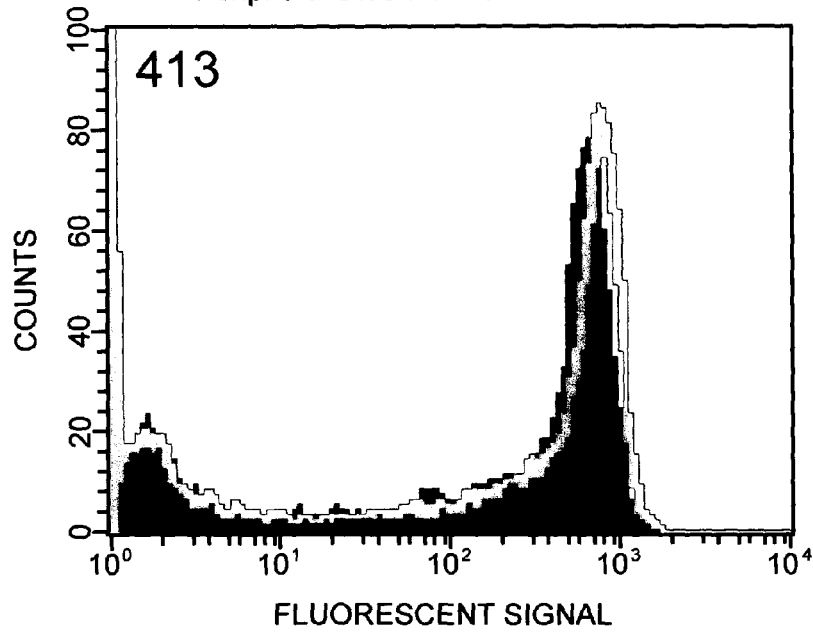
Figure 18E:
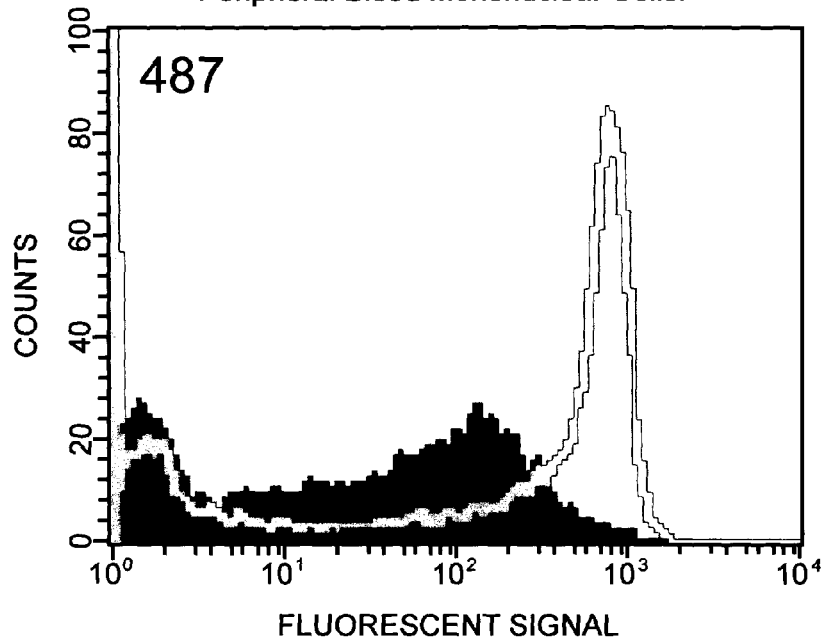
Figure 18F:
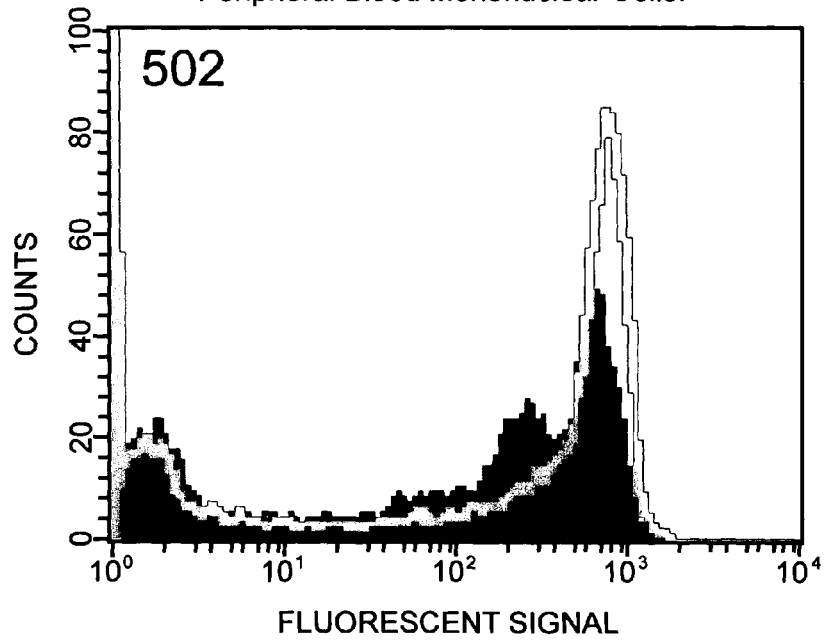

One embodiment of the invention is antibodies which recognize the RB isoform of CD45. Preferably, these antibodies are fully human antibodies and may be used to block undesirable reactions in patients with transplant rejection and/or autoimmune diseases.

The antibodies were produced by immunizing XenoMouse® mice producing human antibodies with IgG2 constant regions (XMG2) (Abgenix, Inc., Fremont, Calif.) with various CD45RB antigens, including T cell lines which express CD45RB, a transfected cell line which expresses CD45RB, and a variety of peptides. In some cases, combinations of the antigens were used for immunization. The lymph nodes and spleens were removed and Memory B cells were isolated and grown in tissue culture. The memory B cells were induced to proliferate and differentiate into plasma cells. The antibody produced by these plasma B cells was screened for their specificity for CD45RB. If specific antibodies were identified, the B cell which expressed them was isolated and the heavy and light chain variable regions sequenced. The antibodies were further analyzed for binding to human T cells as well as for down-regulation of CD45RB and L-Selectin on human T cells.

A total of 22 antibodies were identified as binding specifically to the RB isoform of CD45. The antibodies showed different specificities in binding to human and macaque naïve or activated T cells as well as different abilities to down-regulate the expression of CD45RB and L-selectin. These properties may make each antibody useful for a particular disease or for a stage of a disease.

In addition, the sequence homologous to the human CD45RB 46 mer was identified in macaque. Proteins encoded by this nucleotide sequence were used to screen for antibodies which also bind to macaque T cells. This reagent would be useful to identify antibodies that could directly be used for preclinical validation in monkeys.

Thus, one embodiment is an antibody which comprises at least one heavy chain, or fragment thereof, having the amino acid sequence of SEQ ID NOs: 55, 59, 63, 67, 71, 75, 79, 83, 87, 91, 95, 99, 103, 107, 111, 115, 119, 123, 127, 131, 135 or 139 and/or one light chain or fragment thereof, having the amino acid sequence of SEQ ID NOs: 57, 61, 65, 69, 73, 77, 81, 85, 89, 93, 97, 101, 105, 1113, 117, 121, 125, 129, 133, 137 or 141.

A further embodiment is an antibody which comprises the heavy chain amino acid sequences with the signal sequences removed, SEQ ID Nos: 2, 3, 4, 5, 6, 7, 8, 9, 10, 11, 12, 13, 14, 15, 16, 18, 20, 21, 22, 24, 25 or 26 as shown in FIG. 1 and/or the light chain amino acid sequences with the signal sequences removed, SEQ ID Nos: 28, 29, 30, 31, 32, 34, 35, 36, 37, 38, 39, 40, 1, 42, 43, 44, 45, 47, 49, 50, 51 or 53 as shown in FIG. 2.

A further embodiment is an antibody which comprises one or more of the CDR regions of the heavy or light chain antibodies, as shown in FIGS. 1 and 2.

Antibodies and fragments can be produced using standard methods (see, for example, E. Harlow et al., Antibodies, A Laboratory Manual, Cold Spring Harbor Laboratory, Cold Spring Harbor, N.Y., 1988). However, the isolation, identification, and molecular construction of antibodies has been developed to such an extent that the choices are almost inexhaustible. Therefore, examples of antibody parts, and complexes will be provided with the understanding that this can only represent a sampling of what is available.

In one embodiment, the antibody is a single chain Fv region. Antibody molecules have two generally recognized regions, in each of the heavy and light chains. These regions are the so-called "variable" region which is responsible for binding to the specific antigen in question, and the so-called "constant" region which is responsible for biological effector responses such as complement binding, binding to neutrophils and macrophages, etc. The constant regions are not necessary for antigen binding. The constant regions have been separated from the antibody molecule, and variable binding regions have been obtained. Therefore, the constant regions are clearly not necessary for the binding action of the antibody molecule when it is acting as the ligand portion of the therapeutic complex.

The variable regions of an antibody are composed of a light chain and a heavy chain. Light and heavy chain variable regions have been cloned and expressed in foreign hosts, while maintaining their binding ability. Therefore, it is possible to generate a single chain structure from the multiple chain aggregate (the antibody), such that the single chain structure will retain the three-dimensional architecture of the multiple chain aggregate.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse(tm) strains as published in 1994. See Green et al. Nature Genetics 7:13-21 (1994). The XenoMouse(tm) strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. Nature Genetics 15:146-156 (1997) and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, Ser. No. 07/610,515, filed Nov. 8, 1990, Ser. No. 07/919, 297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495

(1998). See also European Pat. No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. Nos. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Pat. No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

The inventors of Surani et al., cited above and assigned to the Medical Research Counsel (the "MRC"), produced a transgenic mouse possessing an Ig locus through use of the minilocus approach. The inventors on the GenPharm International work, cited above, Lonberg and Kay, following the lead of the present inventors, proposed inactivation of the endogenous mouse Ig locus coupled with substantial duplication of the Surani et al. work.

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals. Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference.

Fv fragments which are single polypeptide chain binding proteins having the characteristic binding ability of multi-chain variable regions of antibody molecules, can be used for the ligand of the present invention. These ligands are produced, for example, following the methods of Ladner et al., U.S. Pat. No. 5,260,203, issued Nov. 9, 1993, using a computer based system and method to determine chemical structures. These chemical structures are used for converting two naturally aggregated but chemically separated light and heavy polypeptide chains from an antibody variable region into a single polypeptide chain which will fold into a three dimensional structure very similar to the original structure of the two polypeptide chains. The two regions may be linked using an amino acid sequence as a bridge.

The single polypeptide chain obtained from this method can then be used to prepare a genetic sequence coding therefor. The genetic sequence can then be replicated in appropriate hosts, further linked to control regions, and transformed into expression hosts, wherein it can be expressed. The resulting single polypeptide chain binding protein, upon refolding, has the binding characteristics of the aggregate of the original two (heavy and light) polypeptide chains of the variable region of the antibody.

In a further embodiment, the antibodies are multivalent forms of single-chain antigen-binding proteins. Multivalent forms of single-chain antigen-binding proteins have significant utility beyond that of the monovalent single-chain antigen-binding proteins. A multivalent antigen-binding protein has more than one antigen-binding site which results in an enhanced binding affinity. The multivalent antibodies can be produced using the method disclosed in Whitlow et al., U.S. Pat. No. 5,869,620, issued Feb. 9, 1999. The method involves producing a multivalent antigen-binding protein by linking at least two single-chain molecules, each single chain molecule having two binding portions of the variable region of an antibody heavy or light chain linked into a single chain protein. In this way the antibodies can have binding sites for different parts of an antigen or have binding sites for multiple antigens.

In one embodiment, the antibody is an oligomer. The oligomer is produced as in PCT/EP97/05897, filed Oct. 24, 1997, by first isolating a specific ligand from a phage-displayed library. Oligomers overcome the problem of the isolation of mostly low affinity ligands from these libraries, by oligomerizing the low-affinity ligands to produce high affinity oligomers. The oligomers are constructed by producing a fusion protein with the ligand fused to a semi-rigid hinge and a coiled coil domain from Cartilage Oligomeric Matrix Protein (COMP). When the fusion protein is expressed in a host cell, it self assembles into oligomers.

Preferably, the oligomers are peptabodies (Terskikh et al., Biochemistry 94:1663-1668 (1997)). Peptabodies can be exemplified as IgM antibodies which are pentameric with each binding site having low-affinity binding, but able to bind in a high affinity manner as a complex. Peptabodies are made using phage-displayed random peptide libraries. A short peptide ligand from the library is fused via a semi-rigid hinge at the N-terminus of the COMP (cartilage oligomeric matrix protein) pentamerization domain. The fusion protein is expressed in bacteria where it assembles into a pentameric antibody which shows high affinity for its target. Depending on the affinity of the ligand, an antibody with very high affinity can be produced.

It will be understood by those skilled in the art that a monoclonal antibody can be subjected to the techniques of recombinant DNA technology to produce other derivative antibodies or chimeric molecules which retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin. For example U.S. Pat. No. 4,816,567 (herein incorporated by reference) discloses one method for producing chimeric antibodies, though it is to be understood that there are a wide variety of methods and vectors available.

The antibodies may be used in the form of pharmaceutical compositions. The pharmaceutical composition may include at least one antibody which recognizes the CD45RB isoform. For example, the pharmaceutical composition may contain two different antibodies: one which recognizes one antigenic determinant on the CD45RB antigen, the other antibody which recognizes a different antigenic determinant. Alternatively, the pharmaceutical composition may contain more than two different antibodies.

The pharmaceutical composition may additionally contain other treatments for the disease, including anti-inflammatories, immune modulators, and any other pharmaceuticals which are used to treat autoimmune diseases. The pharmaceutical composition may alternatively include any pharmaceuticals which are used to reduce the action of the immune system on transplanted cells, organs or tissues. The pharmaceutical composition may contain substances which make the patient more comfortable during treatment, reduce side-effects, or enhance uptake.

The pharmaceutical compositions may contain additives, excipients, or other substances which allow for more effective administration.

The antibodies or pharmaceutical compositions may be used for the treatment of diseases which involve T cells, including but not limited to autoimmune diseases, transplant rejection, and infections. The autoimmune diseases include but are not limited to: rheumatoid arthritis, autoimmune diabetes, scleroderma, multiple sclerosis, lupus, fibromyalgia and fibrositis, and ankylosing spondylitis.

The pharmaceutical preparation may be administered topically, locally, or systemically. For example for the treatment of autoimmune skin disorders, the preparation may be administered topically. Alternatively, the preparation may be administer intranasally, inhaled, ingested, or injected. The disease for which the pharmaceutical preparation is being administered may determine the best mode of administration.

The dosage will vary depending on the mode of administration, the disease, the patient, and the severity of the condition. In general, however, a dosage from about 0.01 mg/kg body weight to about 25 mg/kg body weight of the antibody or antibody mixture is administered intravenously one time per day to one time per week to one time per month. Another preferable dosage is between 0.2 mg/kg body weight to 10 mg/kg body weight. Still another preferable dosage is between 0.02 mg/kg body weight to 5 mg/kg body weight. Alternatively, the administration may be during a flare-up of the disease. Alternatively, the administration may be in conjunction with the transplantation of the cell, tissue, or organ.

Some of the infections which have an autoimmune component include but are not limited to: rheumatic fever, syphilis, and lyme disease.

Thus, one embodiment is a method for the treatment or prevention of tissue or organ transplant rejection and for treating an autoimmune disease comprising the administration of the monoclonal antibodies that specifically bind to the CD45RB epitope of the CD45RB isoform. Any of the antibodies comprising the sequences of SEQ ID NOs: 55, 59, 63, 67, 71, 75, 79, 83, 87, 91, 95, 99, 103, 107, 111, 115, 119, 123, 127, 131, 135, 139, 57, 61, 65, 69, 73, 77, 81, 85, 89, 93, 97, 101, 105, 109, 113, 117, 121, 125, 129, 133, 137, 141, SEQ ID NOs: 2, 3, 4, 5, 6, 7, 8, 9, 10, 11, 12, 13, 14, 15, 16, 18, 20, 21, 22, 24, 25, 26 shown in FIGS. 1A-1B, SEQ ID NOs: 28, 29, 30, 31, 32, 34, 35, 36, 37, 38, 39, 40, 41, 42, 43, 44, 45, 47, 49, 50, 51 and/or 53 as shown in FIGS. 2A-2B may be used in the method. However, characteristics of certain antibodies may make them particularly suited for use in the treatment of a particular disease or stage of a disease.

Selected embodiments of the antibodies and methods are illustrated in the Examples below:

EXAMPLES

XenoMouse animals were immunized with the antigens with the goal of generating anti-CD45RB specific antibodies (see Example 1). Serological analysis was conducted on these mice to identify anti-CD45RB hyper-immune animals and select the appropriate mice for harvest. B cells isolated from the spleen and lymph nodes of the harvested animals were cultured and those plasma cells secreting CD45RB-specific antibodies were isolated as described in Babcook et al., *Proc. Natl. Acad. Sci. USA*, 93:7843-7848 (1996). The cultured B cells were then allowed to differentiate into plasma cells. After about one week, the resulting plasma cells were frozen and the supernatant was used to identify CD45RB-specific antibodies as described in Example 2. The wells containing anti-CD45RB-specific antibodies for each harvest were identified by ELISA or FMAT technology (see Examples 6 through 13). These wells were analyzed using the hemolytic plaque assay to identify CD45RB 46 mer-specific plasma cells (see Example 3). These single antigen-specific plasma cells were isolated by micromanipulation and their specificity was captured using single cell RT-PCR to isolate and analyze the cDNA encoding both the heavy and light chain variable regions (see Example 5). These variable regions were then cloned into expression constructs and used to generate recombinant monoclonal antibody (see Example 4). The antigen binding of the recombinant antibodies was confirmed, and large amounts of antibodies were produced to further characterize the antibodies that will prove useful as therapy in the treatment of autoimmune diseases and transplant rejection.

Examples 6 and 13 detail the immunization, serology, screening data and recombinant antibodies generated for each harvest that yielded a unique anti-CD45RB specific antibody (Harvests 2, 4, 6-11). Example 14 summarizes the binding specificities of the 22 unique anti-CD45RB antibodies to the different CD45RB peptides, transiently expressed CD45RB in CHO cells or endogenously expressed CD45RB in human or macaque T cells. Example 15 provides detailed FACS analysis of the anti-CD45RB antibodies binding to both naïve and activated human and macaque T cells.

Examples 16 though 17 characterize the biological activities of the anti-CD45RB antibodies. Example 16 provides details of the ability of the anti-CD45RB antibodies to down-regulate the expression of CD45RB and L-Selectin. Example 17 summarizes the effects of the anti-CD45RB antibodies on the proliferation and cytokine production of human peripheral blood mononuclear cells (PBMNC) in response to CD3 cross-linking by anti-CD3 antibody.

Example 1

Immunization of the XenoMouse Animals

Monoclonal antibodies against CD45RB were developed by sequentially immunizing XenoMouse animals (XenoMouse® XG2, Abgenix, Inc. Fremont, Calif.) with various CD45RB antigens (see Table 2). In some cases the mice were immunized with the 5 human CD45RB peptides detailed in Table 3. In other cases, the mice were immunized with a mixture of the peptides and CEM, a T cell line which naturally expresses CD45RB. Alternatively, HEK-293 cells that were transfected with a plasmid to express the full-length CD45RB were used. In addition, TCE was added to provide antigen-independent T cell help to B cells. TCE is a T cell epitope which when conjugated to antigen will provide antigen-specific B cells with MHC class II restricted T cell help. The T cell help will provide antigen-specific B cells with the signals required for clonal expansion, class switching, somatic hypermutation and differentiation to plasma cells.

The immunization schedules are provided in Examples 6 through 13 for the harvests outlined in Table 2 that resulted in the generation of anti-CD45RB-specific antibodies. Typically, the antigens were administered IP or B/IP over a period of at least 3 months and for up to 7 months. The lymph nodes and spleen were typically harvested between about 3 months and about 7 months.

TABLE 2

Summary of the CD45RB Harvests and B cell cultures: The human CD45RB peptides that are referred to in Table 2 are detailed below in Table 3 (46mer, 18mer, 20.1, 20.2 and 20.3).

| Harvest | 1 | 2 | 3 | 4 | 5 | 6 |
|---|---|---|---|---|---|---|
| Mice | K522-3 | K522-2 | K522-4 | K522-1 | L576-8 | L576-6 |
| Immunogen | CEM cells and 293 cells transfected with CD45RB | CEM cells and 293 cells transfected with CD45RB | CEM cells and 293 cells transfected with CD45RB | CEM cells and 293 cells transfected with CD45RB | Peptides + TCE | Peptides + TCE |
| Cultures | 50 plates | 35 plates | 50 plates | 50 plates | 40 plates | 50 plates |

| Harvest | 7 | 8 | 9 | 10 | 11 |
|---|---|---|---|---|---|
| Mice | L577-2 and -14 | L577-6 and -8 | L577-3 and -5 | L577-11 and -15 | L574-1 and -14 |
| Immunogen | Peptides + CEM cells + TCE | Peptides + CEM cells + TCE | Peptides + CEM cells + TCE | Peptides + CEM cells + TCE | CEM cells + TCE |
| Cultures | 50 plates | 105 plates | 80 plates | 80 plates | 100 plates |

Thus, in Table 2, mouse K522-3 was immunized with a mixture of CEMs and HEK-293 cells transiently transfected with a CD45RB expression vector. The lymph nodes and spleen were harvested, and 50 plates were seeded. Similarly, mouse L576-6 was immunized with the five human peptides (Human 46 mer, Human 18 mer, Human 20.3, Human 20.1, and Human 20.2 from Table 3) alone with the TCE epitope. The lymph nodes and spleen were harvested, and 50 plates were seeded. The other mice were immunized as shown in Table 2.

TABLE 3

Peptides used as Immunogens or as Screening Reagents: The RB exon of human CD45 is shown as Human 46mer. The differences between human and macaque 46 mer are shown by the presence of an amino acid whereas identity between species is shown by a '-'. The putative N-linked glycosylation site is shown by '*'.

| | | |
|---|---|---|
| Human 46 mer: | VSSVQTPHLPTHADSQTPSAGTDTQTFSGSAANAKLNPTPGSNAIS | (SEQ ID NO: 142) |
| Macaque 46 mer: | ---AL--------------T------P------TT-S---R--D-- | (SEQ ID NO: 143) |
| Human 18 mer: | VSSVQTPHLPTHADSQTPC | (SEQ ID NO: 144) |
| Human 20.3: | VSSVQTPHLPTHADSQTPSA | (SEQ ID NO: 145) |
| Human 20.1: | ADSQTPSAGTDTQTFSGSAA | (SEQ ID NO: 146) |
| Human 20.2: | FSGSAANAKLNPTPGSNAIS | (SEQ ID NO: 147) |

The * above marks the putative N-linked glycosylation site in the Human 46 mer sequence.

The nucleotide sequence encoding the RB exon of macaque CD45RB (macaque 46 mer) was identified by reverse-transcriptase polymerase chain reaction using human CD45 specific oligonucleotide primers. The cDNA was sequenced and translated to determine the amino acid sequence of the RB exon of macaque CD45RB (Table 3). The DNA encoding the macaque RB exon was used to replace the RB exon in the full length human CD45RB expression construct to generate a chimeric expression construct. This new expression construct and the full length human CD45RB expression construct allowed the transient transfection of both human and macaque CD45RB in CHO cells. The isolation of the nucleotide sequence of the RB exon of macaque CD45RB allowed the synthesis of the macaque 46 mer peptide. This peptide was used in conjunction with the human 46 mer peptide to screen human CD45RB-specific antibodies for cross-reactivity to macaque CD45RB.

Example 2

Screening for Antibodies which Secifically Recognized Human CD45RB

Two screens were used to identify antibodies in the pooled supernatant which specifically recognized CD45RB.

The first screen was the Native Binding Assay and involved identifying whether the antibodies bound to CHO cells expressed either CD45RB or CD45RO. The native binding assay was conducted on CHO cells transiently expressing full length CD45RB. Supernatants were qualitatively assessed and ranked for relative binding by eye or using FMAT technology (see FIG. 3) as follows:

4.84 Native Binding Assay in Transiently Transfected CHO Cells.
1.1 CHO cells were transiently lipofected with full length CD45RB or CD45RO.
1.2 After 48 hours, the cells were trypsinized and seeded in Terasaki dishes (5000 cells/well). The cells were cultured overnight at 37° C.
1.3 Culture media was removed and cells were stained with 10 uL of B-cell culture supernatant for 2 hours on ice.
1.4 The monoclonals 6G3 or PC2 were included as a positive controls; titrating 1:2 from 250 ng/mL. An irrelevant XG2 recombinant control was also included in the assay.
1.5 After the Primary antibody incubation, the media was removed and the cells were fixed with 1% paraformaldehyde (10 uL for 20 min).
1.6 The cells were washed twice with 20 uL PBS.
1.7 The secondary antibody (Goat anti-Human IgG Fc Alexa 488 2 ug/mL) was incubated on ice for 1 hour.
1.8 The cells were washed twice with 20 uL PBS.
1.9 The cells were viewed by fluorescent microscopy.

In FIG. 3, the green staining represents antibody binding to the cell membrane.

Thus, in FIG. 3, antibodies 39E11 (sc324), 16C9 (sc009), and 1G10 (sc026) showed specific binding to CD45RB-expressing CHO cells. The same assay was performed using CD45RO cells to confirm that the antibodies specifically recognized the RB isotype. Thus, if binding was positive on both cells, the antibodies were not RB specific. But, if binding was positive for only the CHO cells expressing CD45RB, they were RB specific. This assay could also be used with an expression construct encoding the RB exon of macaque CD45RB to screen for human and macaque cross-reactivity antibodies from B cell culture supernatants or recombinant antibodies.

Alternatively or in addition, the peptide assay or antigen coated ELISA was performed. The antigen-coated ELISA was performed using synthetic peptides from the RB-exon of CD45RB as follows:

Antigen-specific ELISA Protocol:
1) CD45RB peptides coated O/N onto Corning Costar Universal binding plates (poduct #2503), at these concentrations, 46 mer 2 ug/ml, 20 mers 0.87 ug/ml and the 18 mer at 0.78 ug/ml.
2) Coating solution removed from the plates with several firm flicks, some remaining liquid remains in the wells.
3) UV irradiate the plates 4 minutes at 360 nm.
4) The plates were washed five times with dH$_2$O.
5) Block plates with 250 ul of 2% Milk/PBS, 30 minutes at RT.
6) Wash plate, 5 times with dH2O
7) 40 ul of 2% Milk/PBS added to the plate, then 10 ul of B cell supernatant added to each well, 1 hour at RT.
8) Wash plate, 5 times with dH2O
9) To each well add 50 ul of Gt anti-Human (Fc)-HRP at 1 ug/ml, 1 hour at RT.
10) Wash plate, 5 times with dH2O
11) To each well add 50 ul of TMB substrate.

The antibodies of interest were those which bound to CD45RB peptides.

The first 6 harvests were analyzed by eye. Harvests 7-11 were analyzed using an FMAT fluorescence plate reader.

The specific B cell of interest was identified and isolated as in Example 3.

Example 3

Identification and Isolation of a CD45RB-specific Plasma Cells

After the well of interest was identified, the specific B cell was identified and isolated using the hemolytic plaque assay. The assay was performed using sheep red blood cells (SRBCs) coated with biotinylated peptide antigen. The B cells from the well of interest were thawed and plated. Then the peptide-coated SRBCs were mixed with the plasma cells. Complement was added as well as antisera that recognized the human antibodies. The cells of interest showed a zone of lysis in which the SRBCs were lysed around the plasma cell which was expressing and secreting the antigen specific antibodies.

CD45RB-specific Hemolytic Plaque Assay:

4.84 Biotinylation of Sheep Red Blood Cells (SRBC)
1.1 Completely re-suspend the 25% stock of SRBCs stored in RPMI media by rocking the tube back and forth several times.
1.2 Aliquot 1.0 ml of 25% stock into a 15 ml falcon tube. Spin cells down and remove supernatant then add or remove SRBCs to achieve a 250 ul packed cell pellet. Re-suspend in 4.75 ml PBS pH 8.6.
1.3 In a separate, 50 ml tube, add 20 ml of PBS pH 8.6 and add to this 1.25 mg of Sulfo-NHS biotin. Once biotin has completely dissolved add the 5 ml of SRBCs and rotate at RT for 1 hour.
1.3.1 For peptide plaque assays biotinylation of SRBC's was as described in 1.3, however for the plaque assay using recombinant CD45RB-his biotin on the SRBC's was doubled. Therefore, 5.0 mgs of Sulfo-NHS biotin was used in step 1.3.

1.4 Centrifuge SRBCs at 3000 g for 5 min and draw off the supernatant. Add 25 mls PBS pH 7.4 to wash.

1.5 Repeat the wash cycle 3 times, then add 4.75 ml immune cell media to the 250 ul biotinylated-SRBC (B-SRBC) pellet and gently re-suspend the B-SRBC (5% B-SRBC stock), store at 4 C.

Streptavidin (SA) Coating of B-SRBCs:

2.1 Aliquot 1 ml of the 5% B-SRBC stock into to a fresh eppendorf tube.

2.2 Pellet B-SRBC with a pulse spin at 8000 rpm (6800 rcf) in microfuge, draw off supernatant, re-suspend pellet in 1.0 ml PBS pH 7.4, repeat centrifugation.

2.3 Repeat wash cycle 2 times then re-suspend the B-SRBC pellet in 1.0 ml of PBS pH 7.4, final concentration 5% (v/v).

2.4 Add 10 ul of 10 mg/ml streptavidin stock, mix and rotate at RT for 20 min.

2.4.1 For peptide plaque assays the amount of streptavidin used was as described in 2.4, however for the plaque assay using recombinant CD45RB-his 10 fold more streptavidin was loaded onto the biotinylated-SRBC's. Therefore, 100 uls of 10 mg/ml Sulfo-NHS biotin was used in step 2.4.

2.5 Repeat washing steps 2.0 and 3.0, re-suspended SA-SRBC in 1 ml PBS pH 7.4 (5% (v/v)).

3.0 CD45RB-His Coating of SA-SRBCs:

3.1 For peptide plaque assays the biotinylated peptides were coated onto SRBC's at the following concentrations, 3.2 For recombinant CD45RB-his plaque assays the SA-SRBC were coated with unquantitated Biotinylated-CD45RB-His. Coating was determined by coating the B-CD45RB-his maximally to the point of no red cell agglutination.

3.3 Mix and rotate at RT for 20 min.

3.4 Wash SRBC as in steps 2.0 and 3.0 in streptavidin coating of SRBC.

3.5 Resuspend CD45RB-coated SRBC in RPMI (+10% FCS) to a final concentration of 5% (v/v).

Determination of the Quality of CD45RB-SRBC by Immunofluorescence (IF):

4.1 Add 10 ul of 5% SA-SRBC to a fresh 1.5 ml eppendorf tube containing 40 ul of PBS.

4.2 Add Mu-anti-CD45RB antibody (m6G3) to each sample of SRBCs at 45 ug/ml.

4.3 Rotate at RT for 25 min.

4.4 Wash cells 3 times with 100 ul of PBS.

4.5 Re-suspend cells in 50 ul of PBS and spike in Gt-anti Human IgG Fc antibody conjugated to Alexa488.

4.6 Rotate at RT for 25 min.

4.7 Wash 1 time with 100 ul PBS and re-suspend in 10 ul PBS.

4.8 Spot 10 ul of stained cells on to a clean glass microscope slide, place a glass coverslip over each sample, observe under fluorescent light and score on an arbitrary scale of 0-4.

5.0 Preparation of Plasma Cells:

5.1 Harvest the contents of a single microculture well previously identified by various assays as containing a B cell clone secreting the immunoglobulin of interest 5.2 Using a 100-1000 ul pipetman recover the contents of the well by adding 37 C. RPMI (+10% FCS). Pipet up and down 2-3 times to re-suspend cells in and then transfer to a fresh 1.5 ml eppendorf tube (final vol approx 500-700 ul).

5.3 Centrifuge in microfuge at 1500 rpm (240 rcf) for 2 minutes at room temperature, then rotate tube 180 degrees and spin again for 2 minutes at 1500 rpm. Draw off freeze media.

5.4 Re-suspend the immune cells in 100 ul RPMI (10% FCS) by gently pipetting up and down several times using a 10-100 ul pipettman.

5.5 Centrifuge as in step 3.0, draw off the wash media leaving the cell pellet untouched.

5.6 Repeat steps 5.4 and 5.3.

5.7 Re-suspend cells in 60 ul RPMI (FCS) and store washed immune cells on ice until ready to use.

6.0 Preparation of 4× Stocks of Complement and Enhancing Sera.

6.1 Thaw an aliquot of frozen (−70° C.) Guinea pig serum (source of complement) on ice. Make 4× stock in RPMI (FCS).

6.2 Prepare a 4× stock (1:900) of enhancing sera in RPMI (FCS). Concentration must be determined empirically for each lot.

Plaque Assay:

7.1 Glass slides are prepared in advance. Silicone edges are applied to 2 inch×3 inch glass slides and allowed to cure overnight at RT. Before use the slides are treated with approx. 5 ul of SigmaCoat wiped evenly over glass surface, allowed to dry then wiped vigorously.

7.2 To the 60 ul sample of cells add 60 ul of each of CD45RB-His coated SRBC (5% v/v stock), 4× complement stock and 4× enhancing sera stock. Total volume of mixture is 240 ul.

7.3 Spot the mixture onto the glass slide. Each spot is approx. 3-5 ul. Be sure to avoid air bubbles.

7.4 Overlay the spots with undiluted Paraffin oil. Ensure there is enough oil such that the spots do not breach the surface.

7.5 Incubate the slides at 37 C. for a minimum of 45 minutes. If no plaques are found incubate a further 15 minutes and recheck.

7.6 Micromanipulate the single cells as soon as possible.

Example 4

Antibody Expression and Purification

After isolation of the single plasma cells, mRNA was extracted and reverse transcriptase PCR was conducted to generate cDNA. The cDNA encoding the variable heavy and light chains was specifically amplified using polymerase chain reaction. The variable heavy chain region was cloned into an IgG2 expression vector. This vector was generated by cloning the constant domain of human IgG2 into the multiple cloning site of pcDNA3.1+/Hygro (Invitrogen, Burlington, ON). The variable light chain region was cloned into an IgK expression vector. This vector was generated by cloning the constant domain of human IgK into the multiple cloning site of pcDNA3.1+/Neo (Invitrogen, Burlington, ON). The heavy chain and the light chain expression vectors were then co-lipofected into a 60 mm dish of 70% confluent human embryonal kidney 293 cells and the transfected cells were allowed to secrete a recombinant antibody with the identical specificity as the original plasma cell for 24 hours. The supernatant (3 mL) was harvested from the HEK 293 cells and the secretion of an intact antibody was demonstrated with a sandwich ELISA to specifically detect human IgG. The specificity of the recombinant antibody was assessed through binding of the recombinant antibody in an ELISA to the antigen used to isolate the plasma cell during the hemolytic plaque assay as described in Example 2.

ELISA Method to detect human IgG: The secretion ELISA tests were performed as follows. Plates were coated with 2 mg/mL Goat anti-human IgG H+L O/N as for binding plates. The plates were washed five times with dH$_2$O. Recombinant antibodies were titrated 1:2 for 7 wells from the undiluted supernatant from lipofected cells. The plates were washed five times with dH$_2$O. A goat anti-human IgG Fc-specific HRP-conjugated antibody was added at a final concentration of 1 ug/mL for 1 hour at RT for the secretion ELISA. The plates were washed five times with dH$_2$O. The plates were developed with the addition of TMB for 30 minutes and the ELISA was stopped by the addition of 1 M phosphoric acid. Each ELISA plate was analyzed to determine the optical density of each well at 450 nm.

Purification of anti-CD45RB antibodies. For larger scale production of anti-CD45RB antibodies, the heavy and light chain expression vectors (2.5 ug of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). The recombinant antibodies were purified from the supernatant using a Protein-A Sepharose (Amersham Biosciences, Piscataway, N.J.) affinity chromatography (1 mL). The antibody was eluted from the Protein-A column with 500 mcL of 0.1 M Glycine pH 2.5. The eluate was dialysed in PBS pH 7.4 and was then filter sterilized. The antibody was analyzed by non-reducing SDS-PAGE to assess purity and yield.

Example 5

Sequencing of the Heavy and Light Chain Variable Regions

Once the B cell clone which was expressing the antibody of interest was identified and isolated (in Example 4), the variable light and heavy chain regions with the signal peptide were amplified using PCR and then sequenced.

The amino acid sequences of the heavy and light chain variable regions for the 22 human anti-CD45RB antibodies identified correspond to SEQ ID NOs: 55 and 57, respectively for AB-CD45RB-XG2-009, SEQ ID NO: 59 and 61, respectively for AB-CD45RB-XG2-026, SEQ ID NO: 63 and 65, respectively, for AB-CD45RB-XG2-275, SEQ ID NO: 67 and 69, respectively, for AB-CD45RB-XG2-324, SEQ ID NO: 71 and 73, respectively, for AB-CD45RB-XG2-413, SEQ ID NO: 75 and 77, respectively, for AB-CD45RB-XG2-416, SEQ ID NO: 79 and 81, respectively, for AB-CD45RB-XG2-439, SEQ ID NO: 83 and 85, respectively, for AB-CD45RB-XG2-446, SEQ ID NO: 87 and 89, respectively, for AB-CD45RB-XG2-475, SEQ ID NO: 91 and 93, respectively, for AB-CD45RB-XG2-487, SEQ ID NO: 95 and 97, respectively, for AB-CD45RB-XG2-493, SEQ ID NO: 99 and 101, respectively, for AB-CD45RB-XG2-502, SEQ ID NO: 103 and 105, respectively, for AB-CD45RB-XG2-525, SEQ ID NO: 107 and 109, respectively, for AB-CD45RB-XG2-539, SEQ ID NO: 111 and 113, respectively, for AB-CD45RB-XG2-556, SEQ ID NO: 115 and 117, respectively, for AB-CD45RB-XG2-569, SEQ ID NO: 119 and 121, respectively, for AB-CD45RB-XG2-593, SEQ ID NO: 123 and 125, respectively, for AB-CD45RB-XG2-606, SEQ ID NO: 127 and 129, respectively, for AB-CD45RB-XG2-636, SEQ ID NO: 131 and 133, respectively, for AB-CD45RB-XG2-648, SEQ ID NO: 135 and 137, respectively, for AB-CD45RB-XG2-662 and SEQ ID NO: 139 and 141, respectively, for AB-CD45RB-XG2-662, respectively.

The amino acid sequences of the variable heavy chain of these antibodies, minus the signal peptide, are shown in FIG. 1, and represented by SEQ ID NO: 2, 3, 4, 5, 6, 7, 8, 9, 10, 11, 12, 13, 14, 15, 16, 18, 20, 21, 22, 24, 25 and 26 for AB-CD45RB-XG2-009, AB-CD45RB-XG2-026, AB-CD45RB-XG2-446, AB-CD45RB-XG2-606, AB-CD45RB-XG2-713, AB-CD45RB-XG2-275, AB-CD45RB-XG2-324, AB-CD45RB-XG2-413, AB-CD45RB-XG2-416, AB-CD45RB-XG2-439, AB-CD45RB-XG2-487, AB-CD45RB-XG2-493, AB-CD45RB-XG2-502, AB-CD45RB-XG2-525, AB-CD45RB-XG2-593, AB-CD45RB-XG2-475, AB-CD45RB-XG2-539, AB-CD45RB-XG2-556, AB-CD45RB-XG2-569, AB-CD45RB-XG2-662, AB-CD45RB-XG2-648 and AB-CD45RB-XG2-636, respectively.

The amino acid sequences of the variable light chain of these antibodies, minus the signal peptide, are shown in FIG. 2, and represented by SEQ ID NO: 28, 29, 30, 31, 32, 34, 35, 36, 37, 38, 39, 40, 41, 42, 43, 44, 45, 47, 49, 50, 51 and 53, for AB-CD45RB-XG2-009, AB-CD45RB-XG2-026, AB-CD45RB-XG2-446, AB-CD45RB-XG2-606, AB-CD45RB-XG2-713, AB-CD45RB-XG2-275, AB-CD45RB-XG2-324, AB-CD45RB-XG2-413, AB-CD45RB-XG2-416, AB-CD45RB-XG2-439, AB-CD45RB-XG2-487, AB-CD45RB-XG2-493, AB-CD45RB-XG2-502, AB-CD45RB-XG2-525, AB-CD45RB-XG2-593, AB-CD45RB-XG2-475, AB-CD45RB-XG2-539, AB-CD45RB-XG2-556, AB-CD45RB-XG2-569, AB-CD45RB-XG2-662, AB-CD45RB-XG2-648 and AB-CD45RB-XG2-636, respectively.

The antibodies are identified as "AB-CD45RB-XG2" with a following identifying number. For example, the antibody identified as "AB-CD45RB-XG2-009" correlates with the sequence in FIGS. 1 and 2 identified as single cell (sc) 009". Each region in the antibodies is separately identified as a framework region (FR) or a complementary determining region (CDR). The variable heavy chain (gamma) and the variable light chain (kappa) each contain three CDRs. For the heavy chain, the sections identified as FR1+CDR1+FR2+CDR2+FR3+CDR3+FR4 in FIG. 1 can be assembled with the signal sequence to produce the sequences of SEQ ID Nos: 55, 59, 63, 67, 71, 75, 79, 83, 87, 91, 95, 99, 103, 107, 111, 115, 119, 123, 127, 131, 135 and 139. Similarly for the light chain, the sections identified as FR1+CDR1+FR2+CDR2+FR3+CDR3+FR4 in FIG. 2 can be assembled with the signal sequence to produce the sequences of SEQ ID Nos: 57, 61, 65, 69, 73, 77, 81, 85, 89, 93, 97, 101, 105, 109, 113, 117, 121, 125, 129, 133, 137 and 141.

The heavy chain and light chain variable region nucleotide and amino acid sequences of the human anti-CD45RB antibody designated AB-CD45RB-XG2-009 (sc009) of the invention are represented by the following SEQ ID NO. designations: SEQ ID NO: 54 representing the nucleotide sequence encoding the variable region of the heavy chain, SEQ ID NO: 55 representing the amino acid sequence encoded by the nucleotide sequence of SEQ ID NO: 54, SEQ ID NO: 56 representing the nucleotide sequence encoding the variable region of the light chain, and SEQ ID NO: 57 representing the amino acid sequence encoded by the nucleotide sequence of SEQ ID NO: 56.

The heavy chain and light chain variable region nucleotide and amino acid sequences of the human anti-CD45RB antibody designated AB-CD45RB-XG2-026 (sc026) of the invention are represented by the following SEQ ID NO. designations: SEQ ID NO: 58 representing the nucleotide sequence encoding the variable region of the heavy chain, SEQ ID NO: 59 representing the amino acid sequence encoded by the nucleotide sequence of SEQ ID NO: 58, SEQ ID NO: 60 representing the nucleotide sequence encoding the variable region of the light chain and SEQ ID NO: 61 representing the amino acid sequence encoded by the nucleotide sequence of SEQ ID NO: 61.

The heavy chain and light chain variable region nucleotide and amino acid sequences of the human anti-CD45RB antibody designated AB-CD45RB-XG2-275 (sc275) of the invention are represented by the following SEQ ID NO. designations: SEQ ID NO: 62 representing the nucleotide sequence encoding the variable region of the heavy chain, SEQ ID NO: 63 representing the amino acid sequence encoded by the nucleotide sequence of SEQ ID NO: 62, SEQ ID NO: 64 representing the nucleotide sequence encoding the variable region of the light chain, and SEQ ID NO: 65 representing the amino acid sequence encoded by the nucleotide sequence of SEQ ID NO: 64.

The heavy chain and light chain variable region nucleotide and amino acid sequences of the human anti-CD45RB antibody designated AB-CD45RB-XG2-324 (sc324) of the invention are represented by the following SEQ ID No. designations: SEQ ID NO: 66 representing the nucleotide sequence encoding the variable region of the heavy chain, SEQ ID NO: 67 representing the amino acid sequence encoded by the nucleotide sequence of SEQ ID NO: 66, SEQ ID NO: 68 representing the nucleotide sequence encoding the variable region of the light chain, and SEQ ID NO: 69 representing the amino acid sequence encoded by the nucleotide sequence of SEQ ID NO: 68.

The heavy chain and light chain variable region nucleotide and amino acid sequences of the human anti-CD45RB antibody designated AB-CD45RB-XG2-413 (sc413) of the invention are represented by the following SEQ ID NO. designations: SEQ ID NO: 70 representing the nucleotide sequence encoding the variable region of the heavy chain, SEQ ID NO: 71 representing the amino acid sequence encoded by the nucleotide sequence of SEQ ID NO: 70, SEQ ID NO: 72 representing the nucleotide sequence encoding the variable region of the light chain, and SEQ ID NO: 73 representing the amino acid sequence encoded by the nucleotide sequence of SEQ ID NO: 72.

The heavy chain and light chain variable region nucleotide and amino acid sequences of the human anti-CD45RB antibody designated AB-CD45RB-XG2-416 (sc416) of the invention are represented by the following SEQ ID NO. designations: SEQ ID NO: 74 representing the nucleotide sequence encoding the variable region of the heavy chain, SEQ ID NO: 75 representing the amino acid sequence encoded by the nucleotide sequence of SEQ ID NO: 74, SEQ ID NO: 76 representing the nucleotide sequence encoding the variable region of the light chain, and SEQ ID NO: 77 representing the amino acid sequence encoded by the nucleotide sequence of SEQ ID NO: 76.

The heavy chain and light chain variable region nucleotide and amino acid sequences of the human anti-CD45RB antibody designated AB-CD45RB-XG2-439 (sc439) of the invention are represented by the following SEQ ID NO. designations: SEQ ID NO: 78 representing the nucleotide sequence encoding the variable region of the heavy chain, SEQ ID NO: 79 representing the amino acid sequence encoded by the nucleotide sequence of SEQ ID NO: 78, SEQ ID NO: 80 representing the nucleotide sequence encoding the variable region of the light chain, and SEQ ID NO: 81 representing the amino acid sequence encoded by the nucleotide sequence of SEQ ID NO: 80.

The heavy chain and light chain variable region nucleotide and amino acid sequences of the human anti-CD45RB antibody designated AB-CD45RB-XG2-446 (sc446) of the invention are represented by the following SEQ ID NO. designations: SEQ ID NO: 82 representing the nucleotide sequence encoding the variable region of the heavy chain, SEQ ID NO: 83 representing the amino acid sequence encoded by the nucleotide sequence of SEQ ID NO: 82, SEQ ID NO: 84 representing the nucleotide sequence encoding the variable region of the light chain, and SEQ ID NO: 85 representing the amino acid sequence encoded by the nucleotide sequence of SEQ ID NO: 84.

The heavy chain and light chain variable region nucleotide and amino acid sequences of the human anti-CD45RB antibody designated AB-CD45RB-XG2-475 (sc475) of the invention are represented by the following SEQ ID NO. designations: SEQ ID NO: 86 representing the nucleotide sequence encoding the variable region of the heavy chain, SEQ ID NO: 87 representing the amino acid sequence encoded by the nucleotide sequence of SEQ ID NO: 86, SEQ ID NO: 88 representing the nucleotide sequence encoding the variable region of the light chain, and SEQ ID NO: 89 representing the amino acid sequence encoded by the nucleotide sequence of SEQ ID NO: 88.

The heavy chain and light chain variable region nucleotide and amino acid sequences of the human anti-CD45RB antibody designated AB-CD45RB-XG2-487 (sc487) of the invention, are represented by the following SEQ ID NO. designations: SEQ ID NO: 90 representing the nucleotide sequence encoding the variable region of the heavy chain, SEQ ID NO: 91 representing the amino acid sequence encoded by the nucleotide sequence of SEQ ID NO: 90, SEQ ID NO: 92 representing the nucleotide sequence encoding the variable region of the light chain, and SEQ ID NO: 93 representing the amino acid sequence encoded by the nucleotide sequence of SEQ ID NO: 92.

The heavy chain and light chain variable region nucleotide and amino acid sequences of the human anti-CD45RB antibody designated AB-CD45RB-XG2-493 (sc493) of the invention are represented by the following SEQ ID NO. designations: SEQ ID NO: 94 representing the nucleotide sequence encoding the variable region of the heavy chain, SEQ ID NO: 95 representing the amino acid sequence encoded by the nucleotide sequence of SEQ ID NO: 94, SEQ ID NO: 96 representing the nucleotide sequence encoding the variable region of the light chain, and SEQ ID NO: 97 representing the amino acid sequence encoded by the nucleotide sequence of SEQ ID NO: 96.

The heavy chain and light chain variable region nucleotide and amino acid sequences of the human anti-CD45RB antibody designated AB-CD45RB-XG2-502 (sc502) of the invention are represented by the following SEQ ID NO. designations: SEQ ID NO: 98 representing the nucleotide sequence encoding the variable region of the heavy chain, SEQ ID NO: 99 representing the amino acid sequence encoded by the nucleotide sequence of SEQ ID NO: 98, SEQ ID NO: 100 representing the nucleotide sequence encoding the variable region of the light chain, and SEQ ID NO: 101 representing the amino acid sequence encoded by the nucleotide sequence of SEQ ID NO: 100.

The heavy chain and light chain variable region nucleotide and amino acid sequences of the human anti-CD45RB antibody designated AB-CD45RB-XG2-525 (sc525) of the invention are represented by the following SEQ ID NO. designations: SEQ ID NO: 102 representing the nucleotide sequence encoding the variable region of the heavy chain, SEQ ID NO: 103 representing the amino acid sequence encoded by the nucleotide sequence of SEQ ID NO: 102, SEQ ID NO: 104 representing the nucleotide sequence encoding the variable region of the light chain, and SEQ ID NO: 105 representing the amino acid sequence encoded by the nucleotide sequence of SEQ ID NO: 104.

The heavy chain and light chain variable region nucleotide and amino acid sequences of the human anti-CD45RB antibody designated AB-CD45RB-XG2-539 (sc539) of the invention are represented by the following SEQ ID NO. designations: SEQ ID NO: 106 representing the nucleotide sequence encoding the variable region of the heavy chain, SEQ ID NO: 107 representing the amino acid sequence encoded by the nucleotide sequence of SEQ ID NO: 106, SEQ ID NO: 108 representing the nucleotide sequence encoding the variable region of the light chain, and SEQ ID NO: 109 representing the amino acid sequence encoded by the nucleotide sequence of SEQ ID NO: 108.

The heavy chain and light chain variable region nucleotide and amino acid sequences of the human anti-CD45RB antibody designated AB-CD45RB-XG2-556 (sc556) of the invention are represented by the following SEQ ID NO. designations: SEQ ID NO: 110 representing the nucleotide sequence encoding the variable region of the heavy chain, SEQ ID NO: 111 representing the amino acid sequence encoded by the nucleotide sequence of SEQ ID NO: 110, SEQ ID NO: 112 representing the nucleotide sequence encoding the variable region of the light chain, and SEQ ID NO: 113 representing the amino acid sequence encoded by the nucleotide sequence of SEQ ID NO: 112.

The heavy chain and light chain variable region nucleotide and amino acid sequences of the human anti-CD45RB antibody designated AB-CD45RB-XG2-569 (sc569) of the invention are represented by the following SEQ ID NO. designations: SEQ ID NO: 114 representing the nucleotide sequence encoding the variable region of the heavy chain, SEQ ID NO: 115 representing the amino acid sequence encoded by the nucleotide sequence of SEQ ID NO: 114, SEQ ID NO: 116 representing the nucleotide sequence encoding the variable region of the light chain, and SEQ ID NO: 117 representing the amino acid sequence encoded by the nucleotide sequence of SEQ ID NO: 116.

The heavy chain and light chain variable region nucleotide and amino acid sequences of the human anti-CD45RB antibody designated AB-CD45RB-XG2-593 (sc593) of the invention are represented by the following SEQ ID NO. designations: SEQ ID NO: 118 representing the nucleotide sequence encoding the variable region of the heavy chain, SEQ ID NO: 119 representing the amino acid sequence encoded by the nucleotide sequence of SEQ ID NO: 118, SEQ ID NO: 120 representing the nucleotide sequence encoding the variable region of the light chain, and SEQ ID NO: 121 representing the amino acid sequence encoded by the nucleotide sequence of SEQ ID NO: 120.

The heavy chain and light chain variable region nucleotide and amino acid sequences of the human anti-CD45RB antibody designated AB-CD45RB-XG2-606 (sc606) of the invention are represented by the following SEQ ID NO. designations: SEQ ID NO: 122 representing the nucleotide sequence encoding the variable region of the heavy chain, SEQ ID NO: 123 representing the amino acid sequence encoded by the nucleotide sequence of SEQ ID NO: 122, SEQ ID NO: 124 representing the nucleotide sequence encoding the variable region of the light chain, and SEQ ID NO: 125 representing the amino acid sequence encoded by the nucleotide sequence of SEQ ID NO: 124.

The heavy chain and light chain variable region nucleotide and amino acid sequences of the human anti-CD45RB antibody designated AB-CD45RB-XG2-636 (sc636) of the invention are represented by the following SEQ ID NO. designations: SEQ ID NO: 126 representing the nucleotide sequence encoding the variable region of the heavy chain, SEQ ID NO: 127 representing the amino acid sequence encoded by the nucleotide sequence of SEQ ID NO: 126, SEQ ID NO: 128 representing the nucleotide sequence encoding the variable region of the light chain, and SEQ ID NO: 129 representing the amino acid sequence encoded by the nucleotide sequence of SEQ ID NO: 128.

The heavy chain and light chain variable region nucleotide and amino acid sequences of the human anti-CD45RB antibody designated AB-CD45RB-XG2-648 (sc648) of the invention are represented by the following SEQ ID NO. designations: SEQ ID NO: 130 representing the nucleotide sequence encoding the variable region of the heavy chain, SEQ ID NO: 131 representing the amino acid sequence encoded by the nucleotide sequence of SEQ ID NO: 130, SEQ ID NO: 132 representing the nucleotide sequence encoding the variable region of the light chain, and SEQ ID NO: 133 representing the amino acid sequence encoded by the nucleotide sequence of SEQ ID NO: 132.

The heavy chain and light chain variable region nucleotide and amino acid sequences of the human anti-CD45RB antibody designated AB-CD45RB-XG2-662 (sc662) of the invention are represented by the following SEQ ID NO. designations: SEQ ID NO: 134 representing the nucleotide sequence encoding the variable region of the heavy chain, SEQ ID NO: 135 representing the amino acid sequence encoded by the nucleotide sequence of SEQ ID NO: 134, SEQ ID NO: 136 representing the nucleotide sequence encoding the variable region of the light chain, and SEQ ID NO: 137 representing the amino acid sequence encoded by the nucleotide sequence of SEQ ID NO: 136.

The heavy chain and light chain variable region nucleotide and amino acid sequences of the human anti-CD45RB antibody designated AB-CD45RB-XG2-713 (sc713) of the invention are represented by the following SEQ ID NO. designations: SEQ ID NO: 138 representing the nucleotide sequence encoding the variable region of the heavy chain, SEQ ID NO: 139 representing the amino acid sequence encoded by the nucleotide sequence of SEQ ID NO: 138, SEQ ID NO: 140 representing the nucleotide sequence encoding the variable region of the light chain, and SEQ ID NO: 141 representing the amino acid sequence encoded by the nucleotide sequence of SEQ ID NO: 140.

Example 6

Harvest 2

This example describes the harvest of the XenoMouse K522-2. This mouse of the XenoMouse strain IgG2 (XMG2) was immunized with the following antigens: CEM T cells, HEK-293 cells or TSA cells transiently transfected with full-length CD45RB intraperitoneally (IP) or BIP with no adjuvant. The Immunization Schedule was as follows:

1) CEM cells via BIP; day 18
2) TSA transiently expressing CD45RB via B/IP; day 1
3) TSA transiently expressing CD45RB via B/IP; day 14
4) 293 cells transiently expressing CD45RB via IP; day 56
5) 293 cells transiently expressing CD45RB via IP; day 102

The serum from this animal was analyzed for titers against CEM T cells, untransfected Chinese hamster ovary (CHO) cells, CHO cells transiently expressing CD45RO or CD45RB. The titers were also analyzed against the human 46 mer peptide and CD45RB protein that was affinity purified from CEM T cells using 6G3. The serological response of this mouse is shown in Table 4.

TABLE 4

Serology of the XenoMouse animals K522-1 through 5:

| Mouse ID | CHO cells | CD45RO-CHO cells | CD45RB-CHO cells | CEM T cells | Affinity Purified CD45RB | Human 46mer |
|---|---|---|---|---|---|---|
| K221-1 | <1:100 | 1:300 | 1:300 | 1:1600 | 1:1350 | 1:3200 |
| K221-2 | <1:100 | 1:75 | 1:150 | 1:3200 | 1:150 | 1:400 |
| K221-3 | <1:100 | 1:150 | 1:150 | 1:3200 | 1:450 | 1:3200 |
| K221-4 | <1:100 | 1:75 | 1:75 | 1:800 | 1:150 | 1:200 |
| K221-5 | <1:100 | 1:75 | 1:75 | 1:800 | 1:50 | 1:800 |
| Naive | <1:100 | ND | ND | <1:100 | <1:50 | 1:200 |

The lymph nodes and spleen were harvested on day 107 and the resulting cells were cultured in 35-96 well plates. The B cells were allowed to differentiate into plasma cells and their supernatants were analyzed for the presence of human CD45RB 46 mer-specific antibodies. A total of four anti-CD45RB specific antibodies were identified from this screen and plasma cells producing antibodies against CD45RB were identified using an antigen-specific hemolytic plaque assay followed by the micromanipulation of single antigen-specific plasma cells. The plaque assay results are detailed in Table 5.

TABLE 5

Screening Data and Plaque Data for Harvest 2:

| Well | Tissue | Sheep RBC Coating | Single Cells (SC) Plucked | Recombinant SC Number |
|---|---|---|---|---|
| 16C9 | Lymph | Human 46mer | 008-010 | 009 |
| 15A7 | Lymph | Human 46mer | 011, 012, 016, 017 | — |
| 8D4 | Spleen | Human 46mer | — | — |
| 14D4 | Spleen | Human 46mer | 013, 014 | — |

The antibody AB-CD45RB-XG2-009 (FIG. 1) was isolated from well 16C9. This antibody generated from this well was found to bind specifically to the RB exon of CD45 and AB-CD45RB-XG2-009 was taken forward for further analysis as a recombinant antibody.

Example 7

Harvest 4

This example describes the harvest of the XenoMouse K522-1. This XMG2 mouse was immunized with the antigens CEM T cells, HEK-293 cells or TSA cells transiently transfected with full-length CD45RB BIP or IP. The Adjuvant TiterMax classic (CytRx Corporation, Norcross, Ga.) was used. The Immunization Schedule was as follows:

1) CEM cells via BIP, Day 18

2) TSA transiently expressing CD45RB via B/IP, Day 1

3) TSA transiently expressing CD45RB via B/IP, Day 14

4) Affinity-purified CEM lysate emulsified in TiterMax Classic via IP, 45

5) 293 cells transiently expressing CD45RB via IP, Day 56

6) 293 cells transiently expressing CD45RB via IP; Day 114

7) 293 cells transiently expressing CD45RB via IP; Day 135

The serological response of this mouse is shown in Table 4.

The draining lymph nodes were harvested on day 139 and a total of 35 plates were cultured at 500 CD19+ B cells/well. Eleven wells were identified with CD45RB 46 mer-specific antibodies from this harvest by ELISA. These wells were also analyzed for their ability to bind to human CD45RB transiently over-expressed in CHO cells. These wells were analyzed using the hemolytic plaque assay to identify CD45RB 46 mer-specific plasma cells. These data are shown in Table 6.

TABLE 6

Screening Data and Plaque Data for Harvest 4:

| Well | Primary OD | Secondary OD | CD45RB-CHO Immunofluorescence | Single Cells (SC) Plucked | Recombinant SC Number |
|---|---|---|---|---|---|
| 1G10 | 0.504 | 0.366 | +++ | 025-032 | 026 |
| 3H1 | 1.528 | 0.560 | ++++ | 033-040 | same as 026 |
| 6A5 | 0.310 | 0.179 | 1/2 + | 041-044 | same as 026 |
| 7C5 | 0.313 | 0.143 | + | 052, 074-076 | same as 026 |
| 8H9 | 0.524 | 0.221 | + | 068-073 | — |
| 14H7 | 1.122 | 0.391 | ++ | 063-067 | — |
| 27G14 | 1.496 | 0.453 | +++ | 057-062 | same as 026 |
| 27G12 | 0.655 | 0.290 | + | 053-056 | — |
| 28A6 | 0.923 | 0.395 | ++ | 077-089 | same as 026 |
| 30E11 | 0.691 | 0.366 | + | — | — |
| 38E2 | 0.332 | 0.142 | 1/2 + | 090-094 | — |
| 9F9 | 0.343 | 0.101 | 1/2 + | 095-097 | — |

The antibody AB-CD45RB-XG2-026 (FIG. 2) was isolated from well 1G10. This antibody was found to bind specifically to the RB exon of CD45 and therefore was further analyzed as a recombinant antibody. Other recombinant antibodies were also generated from 3H1, 6A6, 7C5, 30E11 and 38E2; however, these antibodies were all identical to AB-CD45RB-XG2-026.

Example 8

Harvest 6

This example describes the harvest of the XenoMouse L576-6. This XMG2 mouse was immunized with the human CD45RB-specific peptides -18 mer, 20.1, 20.2, 20.3 and 46 mer BIP with Complete Freund's Adjuvant (CFA, Sigma, Oakville, ON) and Incomplete Freund's Adjuvant (IFA, Sigma, Oakville, ON). The Immunization Schedule was as follows:
1) 5 peptides (2 ug of each)+T cell epitope with CFA, Day 1
2) 5 peptides (2 ug of each)+T cell epitope with IFA, Day 14
3) 5 peptides (2 ug of each)+T cell epitope with IFA, Day 29
4) 5 peptides (2 ug of each)+T cell epitope with IFA, Day 43
5) 5 peptides (2 ug of each)+T cell epitope with IFA, Day 57

The serological response of this mouse is shown in Table 7.

TABLE 7

Serology of the XenoMouse animals L576-1 through 15:

| Mouse ID | 6G3 Competition | Human 46mer | Human 18mer | Human 20.1 | Human 20.2 | Human 20.3 |
|---|---|---|---|---|---|---|
| L576-1 | − | 1:4050 | ND | ND | ND | ND |
| L576-2 | − | 1:1350 | ND | ND | ND | ND |
| L576-3 | − | 1:1350 | ND | ND | ND | ND |
| L576-4 | − | 1:4050 | ND | ND | ND | ND |
| L576-5 | + | 1:4050 | ND | ND | ND | ND |
| L576-6 | + | 1:36450 | 1:4000 | 1:32000 | 1:500 | 1:2000 |
| L576-7 | − | 1:36450 | ND | ND | ND | ND |
| L576-8 | +/− | 1:4050 | ND | ND | ND | ND |
| L576-9 | +/− | 1:12150 | ND | ND | ND | ND |
| L576-10 | − | 1:36450 | ND | ND | ND | ND |
| L576-11 | − | 1:4050 | ND | ND | ND | ND |
| L576-12 | − | 1:12150 | ND | ND | ND | ND |
| L576-13 | − | 1:1350 | ND | ND | ND | ND |
| L576-14 | − | 1:36450 | ND | ND | ND | ND |
| L576-15 | − | 1:4050 | ND | ND | ND | ND |

The spleen and draining lymph nodes were harvested on day 83. Plasma cells were isolated directly from the spleen and lymph nodes from L576-6. These cells were plaqued using different peptide antigens in the hemolytic plaque assay as shown in Table 8.

TABLE 8

Direct Plaque Data for Harvest 6:

| Tissue | Sheep RBC Coating | Single Cells Plucked | Recombinant SC Number |
|---|---|---|---|
| Spleen | Human 18mer | 168-178, 393 | — |
|  | Human 20.1 | 155, 156, 179-184, 200-205 | — |
|  | Human 20.2 | 153, 154, 185-189, 192-197, 206-211, 378-385, 406-412 | — |
|  | Human 20.3 | — | — |
|  | Human 46mer | 164-167, 190, 191, 198, 199 | — |
|  | Human 18mer and 20.2 | 413-421 | 413, 416 |
| Inguinal Lymph Nodes | Human 18mer | 163 | — |
|  | Human 20.1 | 160 | — |
|  | Human 20.2 | — | — |
|  | Human 46mer | 157, 158 | — |
| Pooled Lymph Nodes | Human 18mer | — | — |
|  | Human 20.1 | 159, 161, 162 | — |
|  | Human 20.2 | — | — |
|  | Human 46mer | — | — |

A total of 50 plates were cultured from the lymph nodes of XenoMouse animal L576-6 at 500 CD19+ B cells/well. There were 5 plates set up from the splenic B-lymphocytes, 11 plates from the inguinal lymph nodes, 13 plates from the para-aortic lymph nodes and 12 plates from the remaining pooled lymph nodes (popliteal, mesenteric, axillary, scapular and cervical). Eighteen wells with CD45RB peptide-specific antibodies were identified from this harvest by ELISA (Table 9). These wells were de-convoluted to identify specifically which peptide each well bound. These wells were also analyzed for their ability to bind to human CD45RB transiently over-expressed in CHO cells. These wells were analyzed using the hemolytic plaque assay to identify CD45RB 46 mer-specific plasma cells.

TABLE 9

Screening Data for Harvest 6:

| Well | Tissue | Primary OD | Secondary OD | CD45RB-CHO Immunofluorescence | 18mer OD | 20.1 OD | 20.2 OD | 46mer OD |
|---|---|---|---|---|---|---|---|---|
| 3C8 | Spleen | 0.697 | 1.278 | + | 0.086 | 0.358 | 0.033 | 0.124 |
| 3E1 | Spleen | 0.524 | 1.591 | − | 0.034 | 0.039 | 0.035 | 0.136 |
| 4A4 | Spleen | 2.084 | 0.297 | − | 0.035 | 0.036 | 0.038 | 0.061 |
| 6F11 | Inguinal | 0.544 | 0.305 | − | 0.039 | 0.036 | 0.038 | 0.077 |
| 7F8 | Inguinal | 0.778 | 0.304 | − | ND | 0.096 | ND | 0.204 |
| 9E2 | Inguinal | 0.912 | 0.304 | − | 0.038 | 0.057 | 0.034 | 0.083 |
| 11D3 | Inguinal | 0.580 | 1.002 | − | 0.065 | 0.237 | 0.034 | 0.103 |
| 12E8 | Inguinal | 0.422 | 0.331 | − | 0.038 | 0.041 | 0.035 | 0.058 |
| 14E12 | Inguinal | 0.357 | 0.305 | − | 0.038 | 0.042 | 0.040 | 0.066 |
| 15D5 | Inguinal | 1.067 | 1.470 | + | 0.116 | 0.326 | 0.038 | 0.206 |
| 25D12 | Inguinal | 0.349 | 0.830 | 1/2 + | 0.053 | 0.213 | 0.035 | 0.468 |
| 31H9 | Inguinal | 0.352 | 0.324 | − | ND | 0.121 | ND | 0.059 |
| 34F6 | Inguinal | 0.670 | 1.049 | ++ | 0.070 | 0.193 | 0.038 | 0.078 |
| 37A6 | Para-Aortic | 0.691 | 0.913 | + | 0.151 | 0.366 | 0.036 | 0.142 |
| 39E11 | Para-Aortic | 1.215 | 1.682 | +++ | 0.146 | 0.555 | 0.037 | 0.208 |
| 42F3 | Para-Aortic | 0.617 | 0.928 | ++ | 0.077 | 0.417 | 0.036 | 0.169 |
| 42D8 | Para-Aortic | 0.380 | 0.507 | − | 0.055 | 0.159 | 0.041 | 0.205 |
| 45C8 | Para-Aortic | 0.372 | 0.470 | 1/2 + | 0.075 | 0.193 | 0.034 | 0.088 |

TABLE 10

Summary of the Plaque Assay Data from Harvest 6:

| Well | Sheep RBC Coating | Single Cells Plucked | Recombinant SC Number |
|---|---|---|---|
| 3C8 | Human 20.1 | 287-289 | |
| 3E1 | Human 46mer | — | |
| 4A4 | | | |
| 6F11 | | | |
| 7F8 | Human 46mer | — | |
| 9E2 | | | |
| 11D3 | Human 20.1 | 363-370 | |
| 12E8 | | | |
| 14E12 | | | |
| 15D6 | Human 20.1 | 299-321 | |
| 25D12 | Human 46mer | 359-361 | |
| 31H9 | Human 20.1 | | |
| 34F6 | Human 20.1 | 275-286 | 275 |
| 37A6 | Human 20.1 | 371-377, 392 | |
| 39E11 | Human 20.1 | 322-337, 341 | 324 |
| 42F3 | Human 20.1 | 338-340 | |
| 42D8 | Human 46mer | 403-405 | |
| 45C8 | Human 20.1 | 362 | |

The antibodies AB-CD45RB-XG2-275 (FIG. 3) and AB-CD45RB-XG2-324 (FIG. 4) were isolated from the cultured B cells whereas the antibodies AB-CD45RE-XG2-413 (FIG. 5) and AB-CD45RB-XG2-416 (FIG. 6) were isolated directly from splenic plasma cells. These antibodies were all found to bind specifically to the RB exon of CD45 and therefore were further analyzed as recombinant antibodies.

Example 9
Harvest 7

This example describes the harvest of the XenoMouse animals L577-2 and L577-14. These XMG2 mice were immunized with the CD45RB-specific peptides—18 mer, 20.1, 20.2, 20.3 and 46 mer and CEM T cells BIP using Complete Freund's Adjuvant (CFA) and Incomplete Freund's Adjuvant (IFA). The Immunization Schedule was as follows:

1) CEM T cells ($10^7$ cells) and 5 peptides (2 ug of each)+T cell epitope with CFA, Day 1
2) CEM T cells ($10^7$ cells) and 5 peptides (2 ug of each)+T cell epitope with IFA, Day 14
3) CEM T cells ($10^7$ cells) and 5 peptides (2 ug of each)+T cell epitope with IFA, Day 27
4) CEM T cells ($10^7$ cells) and 5 peptides (2 ug of each)+T cell epitope with IFA, Day 41
5) CEM T cells ($10^7$ cells) and 5 peptides (2 ug of each)+T cell epitope with IFA, Day 56
6) CEM T cells ($10^7$ cells) and 5 peptides (2 ug of each)+T cell epitope with IFA, Day 117
7) CEM T cells ($10^7$ cells) and 5 peptides (2 ug of each)+T cell epitope with IFA, Day 131
8) CEM T cells ($10^7$ cells) and 5 peptides (2 ug of each)+T cell epitope with IFA, Day 145
9) CEM T cells ($10^7$ cells) and 5 peptides (2 ug of each)+T cell epitope with IFA, Day 158
10) CEM T cells ($10^7$ cells) and 5 peptides (2 ug of each)+T cell epitope with IFA, Day 173

Harvest Date: Day 177

The serological responses of these mice are shown in Table 11.

TABLE 11

Serology of the XenoMouse animals L577-1 through 15:

| Mouse ID | 6G3 Competition | Human 46mer-1 | Human 46mer-2 | Human 18mer | Human 20.1 | Human 20.2 | Macaque 46mer |
|---|---|---|---|---|---|---|---|
| L577-1 | − | 1:4050 | ND | ND | ND | ND | 1:200 |
| L577-2 | ++ | 1:4050 | 1:3200 | 1:1600 | 1:3200 | <1:100 | 1:400 |
| L577-3 | − | 1:12150 | 1:1600 | 1:1600 | 1:1600 | <1:100 | 1:400 |
| L577-4 | − | 1:12150 | 1:6400 | >1:6400 | >1:6400 | <1:100 | 1:1600 |
| L577-5 | ++ | ND | >1:6400 | >1:6400 | >1:6400 | <1:100 | 1:200 |
| L577-6 | ++ | 1:12150 | >1:6400 | >1:6400 | >1:6400 | <1:100 | >1:1600 |
| L577-7 | − | 1:12150 | ND | ND | ND | ND | 1:1600 |
| L577-8 | ++ | 1:4050 | 1:6400 | >1:6400 | >1:6400 | <1:100 | 1:400 |
| L577-9 | − | 1:12150 | ND | ND | ND | ND | 1:400 |
| L577-10 | + | 1:4050 | ND | ND | ND | ND | ND |
| L577-11 | ++ | 1:36450 | >1:6400 | >1:6400 | >1:6400 | 1:1600 | 1:800 |
| L577-12 | − | 1:12150 | ND | ND | ND | ND | 1:1600 |
| L577-13 | − | 1:12150 | ND | ND | ND | ND | >1:1600 |
| L577-14 | + | 1:4050 | 1:3200 | 1:3200 | >1:6400 | 1:800 | 1:800 |
| L577-15 | ++ | 1:12150 | 1:6400 | 1:6400 | >1:6400 | 1:1600 | 1:400 |
| L577-16 | − | ND | 1:400 | 1:800 | 1:400 | 1:200 | 1:400 |

The draining lymph nodes were harvested on day 177 and a total of 50 plates were cultured from the lymph nodes of XenoMouse animals L577-2 and L577-14 at 500 CD19$^+$B cells/well. The supernatant from the cultured B cells were harvested and initially screened for CD45RB or CD45RO specificity using FMAT technology. These screens identified 39 CD45RB specific B cell wells. The supernatants from these wells were then analyzed for their ability to bind to both human or macaque peripheral blood mononuclear cells and the different CD45RB peptides. The combined screening data is shown below in Table 12. Two of these wells were further analyzed using the antigen-specific hemolytic plaque assay to isolate antigen-specific plasma cells. These plasma cells were then processed using single cell RT-PCR to isolate the heavy chain and light chain variable regions.

The antibodies AB-CD45RB-XG2-439 (FIG. 7) and AB-CD45RB-XG2-446 (FIG. 8) were isolated from wells 75H9 and 87E3 respectively. The antibodies generated from these wells were found to bind specifically to the RB exon of CD45 and were taken forward for further analysis as recombinant antibodies.

TABLE 12

Screening and Plaque Assay Data for Harvest 7:

| | Screening Data | | | | | Plaque Assay Data | | |
|---|---|---|---|---|---|---|---|---|
| Well | CD45RB-CHO | Human PBMNC | Macaque PBMNC | Human 46mer | Human 20.1 | Sheep RBC Coating | Single Cells (SC) Plucked | Recombinant SC Number |
| 61F3 | +++ | +/− | +/− | 1.21 | 0.18 | − | − | − |
| 62F1 | ++++ | − | − | 1.65 | 0.53 | − | − | − |
| 54C4 | + | + | − | 1.09 | 0.18 | − | − | − |
| 54E10 | + | − | − | 1.01 | 0.29 | − | − | − |
| 55H1 | +++ | + | − | 1.74 | 0.17 | − | − | − |
| 59D1 | + | + | − | 0.78 | 0.13 | − | − | − |
| 60A2 | ++++ | + | − | 2.29 | 0.43 | − | − | − |
| 60E4 | + | + | − | 1.08 | 0.12 | − | − | − |
| 61B2 | + | + | − | 0.20 | 2.78 | Human 20.1 | 430-435 | − |
| 68B12 | 1/2 + | − | − | 0.47 | 0.23 | − | − | − |
| 68C6 | +++ | − | − | 0.86 | 0.22 | − | − | − |
| 69D8 | ++++ | + | − | 1.90 | 0.29 | − | − | − |
| 69E4 | ++++ | + | − | 1.56 | 0.17 | − | − | − |
| 71A6 | ++ | − | − | 1.27 | 0.14 | − | − | − |
| 71C12 | 1/2 + | − | − | 0.52 | 0.12 | − | − | − |
| 72D4 | +++++ | + | − | 2.77 | 0.10 | − | − | − |
| 72D7 | + | − | − | 0.10 | 0.19 | − | − | − |
| 73D3 | ++ | + | − | 1.35 | 0.21 | − | − | − |
| 73H11 | ++ | + | − | 1.31 | 0.23 | − | − | − |
| 76A12 | +++ | + | − | 1.38 | 0.19 | − | − | − |
| 76O11 | +++ | + | − | 1.75 | 0.16 | − | − | − |
| 75H9 | ++++ | + | + | 2.44 | 0.13 | Human 46mer | 436-442 | 439 |
| 76B12 | +++++ | + | − | 2.46 | 0.11 | − | − | − |
| 81E9 | +++++ | + | − | 2.57 | 0.11 | − | − | − |
| 82F4 | +++++ | + | − | 2.20 | 0.27 | − | − | − |
| 84H10 | + | + | − | 1.03 | 0.20 | − | − | − |
| 86A3 | 1/2 + | − | − | 0.37 | 0.23 | − | − | − |

TABLE 12-continued

Screening and Plaque Assay Data for Harvest 7:

| | Screening Data | | | | | Plaque Assay Data | | |
|---|---|---|---|---|---|---|---|---|
| Well | CD45RB-CHO | Human PBMNC | Macaque PBMNC | Human 46mer | Human 20.1 | Sheep RBC Coating | Single Cells (SC) Plucked | Recombinant SC Number |
| 87E3 | +++++ | + | + | 2.32 | 0.15 | Human 46mer | 445-460 | 446 |
| 89G9 | ++++ | + | − | 2.05 | 0.17 | − | − | − |
| 90A2 | ++++ | + | + | 1.95 | 0.19 | − | − | − |
| 90E11 | 1/2 + | − | − | 0.77 | 0.10 | − | − | − |
| 91A9 | ++++ | + | − | 1.79 | 0.11 | − | − | − |
| 91C7 | ++ | − | − | 0.11 | 0.23 | − | − | − |
| 93F11 | 1/2 + | + | − | 0.56 | 0.21 | − | − | − |
| 94B5 | +++ | + | + | 0.81 | 0.17 | − | − | − |
| 95G7 | +++ | + | − | 1.20 | 0.17 | − | − | − |
| 96C12 | 1/2 + | − | − | 0.72 | 0.24 | − | − | − |
| 100F12 | +++ | + | − | 1.42 | 0.18 | − | − | − |
| 100G11 | +++ | + | − | 1.30 | 0.35 | − | − | − |

Example 10

Harvest 8

This example describes the harvest of the XenoMouse animals L577-6 and L577-8. These XMG2 mice were immunized with the CD45RB-specific peptides—18 mer, 20.1, 20.2, 20.3 and 46 mer as well as CEM T cells BIP using Complete Freund's Adjuvant (CFA) and Incomplete Freund's Adjuvant (IFA). The Immunization Schedule was as follows:

1) CEM T cells ($10^7$ cells) and 5 peptides (2 ug of each)+T cell epitope with CFA, Day 1
2) CEM T cells ($10^7$ cells) and 5 peptides (2 ug of each)+T cell epitope with IFA, Day 14
3) CEM T cells ($10^7$ cells) and 5 peptides (2 ug of each)+T cell epitope with IFA, Day 29
4) CEM T cells ($10^7$ cells) and 5 peptides (2 ug of each)+T cell epitope with IFA, Day 43
5) CEM T cells ($10^7$ cells) and 5 peptides (2 ug of each)+T cell epitope with IFA, Day 57
6) CEM T cells ($10^7$ cells) and 5 peptides (2 ug of each)+T cell epitope with IFA, Day 108
7) CEM T cells ($10^7$ cells) and 5 peptides (2 ug of each)+T cell epitope with IFA, Day 122
8) CEM T cells ($10^7$ cells) and 5 peptides (2 ug of each)+T cell epitope with IFA, Day 136
9) CEM T cells ($10^7$ cells) and 5 peptides (2 ug of each)+T cell epitope with IFA, Day 149
10) CEM T cells ($10^7$ cells) and 5 peptides (2 ug of each)+T cell epitope with IFA, Day 202

The serological responses of these mice are shown in Table 11.

The draining lymph nodes were harvested on day 206 and a total of 105 plates were cultured from the lymph nodes of XenoMouse animals L577-6 and L577-8 at 500 CD19+ B cells/well. The supernatant from the cultured B cells were harvested and initially screened for CD45RB or CD45RO specificity using FMAT technology. The supernatants from these wells were then analyzed for their ability to bind to both human or macaque peripheral blood mononuclear cells and the different CD45RB peptides. These screens identified seven CD45RB specific B cell wells of interest and the combined screening data is shown below in Table 13. These wells were further analyzed using the antigen-specific hemolytic plaque assay to isolate antigen-specific plasma cells. These plasma cells were then processed using single cell RT-PCR to isolate the heavy chain and light chain variable regions.

TABLE 13

Screening and Plaque Assay Data for Harvest 8:

| | Screening Data | | | | | | Plaque Assay Data | | |
|---|---|---|---|---|---|---|---|---|---|
| Well | Human CD45RB | Macaque CD45RB | Human 46mer | Human 20.1 | Human 20.2 + 18mer | Macaque 46mer | Sheep RBC Coating | Single Cells (SC) Plucked | Recombinant SC Number |
| 117C1 | + | − | 3.2 | 0.1 | 0.3 | 0.1 | Human 46mer | 490-501 | 493 |
| 123H12 | + | − | 3.7 | 0.1 | 0.3 | 0.3 | Human 46mer | 502-516 | 502 |
| 144B7 | + | − | 4.0 | 0.1 | 0.3 | 0.4 | Human 46mer | 517-523 | − |
| 146G7 | + | − | 3.8 | 0.1 | 0.3 | 0.3 | Human 46mer | 524-538 | 525 |
| 154C3 | + | − | 4.1 | 0.1 | 0.4 | 0.3 | Human 46mer | 592-603 | 593 |
| 170B8 | + | + | 2.5 | 3.9 | 1.7 | 0.8 | Human 20.1 | 470-483 | 475 |
| 201D5 | + | − | 1.8 | 0.1 | 0.5 | 0.1 | Human 46mer | 484-489 | 487 |

The following antibodies AB-CD45RB-XG2-475 (FIG. 9), AB-CD45RB-XG2-487 (FIG. 10), AB-CD45RB-XG2-493 (FIG. 11), AB-CD45RB-XG2-502 (FIG. 12), AB-CD45RB-XG2-525 (FIG. 13) and AB-CD45RB-XG2-593 (FIG. 17) were isolated from harvest 8. The antibodies generated from these wells were found to bind specifically to the RB exon of CD45 and were taken forward for further analysis as recombinant antibodies.

Example 11

Harvest 9

This example describes the harvest of the XenoMouse animals L577-3 and L577-5. These XMG2 mice were immunized with the CD45RB-specific peptides—18 mer, 20.1, 20.2, 20.3 and 46 mer and CEM T cells, BIP using Complete Freund's Adjuvant (CFA) and Incomplete Freund's Adjuvant (IFA). The following Immunization Schedule was used:

1) CEM T cells ($10^7$ cells) and 5 peptides (2 ug of each)+T cell epitope with CFA, Day 1
2) CEM T cells ($10^7$ cells) and 5 peptides (2 ug of each)+T cell epitope with IFA, Day 14
3) CEM T cells ($10^7$ cells) and 5 peptides (2 ug of each)+T cell epitope with IFA, Day 27
4) CEM T cells ($10^7$ cells) and 5 peptides (2 ug of each)+T cell epitope with IFA, Day 41
5) CEM T cells ($10^7$ cells) and 5 peptides (2 ug of each)+T cell epitope with IFA, Day 55
6) CEM T cells ($10^7$ cells) and 5 peptides (2 ug of each)+T cell epitope with IFA, Day 106
7) CEM T cells ($10^7$ cells) and 5 peptides (2 ug of each)+T cell epitope with IFA, Day 120
8) CEM T cells ($10^7$ cells) and 5 peptides (2 ug of each)+T cell epitope with IFA, Day 134
9) CEM T cells ($10^7$ cells) and 5 peptides (2 ug of each)+T cell epitope with IFA, Day 147
10) CEM T cells ($10^7$ cells) and 5 peptides (2 ug of each)+T cell epitope with IFA, Day 204

The serological responses of these mice are shown in Table 11.

The draining lymph nodes were harvested on day 208 and a total of 80 plates were cultured from the lymph nodes of XenoMouse animals L577-3 and L577-5 at 500 CD19$^+$ B cells/well. The supernatant from the cultured B cells were harvested and initially screened for CD45RB or CD45RO specificity using FMAT technology. The supernatants from these wells were then analyzed for their ability to bind to both human or macaque peripheral blood mononuclear cells and the different CD45RB peptides. These screens identified seven CD45RB specific B cell wells of interest and the combined screening data is shown below in Table 14. These wells were further analyzed using the antigen-specific hemolytic plaque assay to isolate antigen-specific plasma cells. These plasma cells were then processed using single cell RT-PCR to isolate the heavy chain and light chain variable regions.

662 (FIG. 21) and AB-CD45RB-XG2-713 (FIG. 22) were isolated from harvest 9. The antibodies generated from these wells were found to bind specifically to the RB exon of CD45 and were taken forward for further analysis as recombinant antibodies.

Example 12

Harvest 10

This example describes the harvest of the XenoMouse animals L577-11 and L577-15. These XMG2 mice were immunized using CD45RB-specific peptides—18 mer, 20.1, 20.2, 20.3 and 46 mer and CEM T cells BIP using Complete Freund's Adjuvant (CFA) and Incomplete Freund's Adjuvant (IFA). The following Immunization Schedule was used:

1) CEM T cells ($10^7$ cells) and 5 peptides (2 ug of each)+T cell epitope with CFA, Day 1
2) CEM T cells ($10^7$ cells) and 5 peptides (2 ug of each)+T cell epitope with IFA, Day 14
3) CEM T cells ($10^7$ cells) and 5 peptides (2 ug of each)+T cell epitope with IFA, Day 27
4) CEM T cells ($10^7$ cells) and 5 peptides (2 ug of each)+T cell epitope with IFA, Day 41
5) CEM T cells ($10^7$ cells) and 5 peptides (2 ug of each)+T cell epitope with IFA, Day 55
6) CEM T cells ($10^7$ cells) and 5 peptides (2 ug of each)+T cell epitope with IFA, Day 106
7) CEM T cells ($10^7$ cells) and 5 peptides (2 ug of each)+T cell epitope with IFA, Day 120
8) CEM T cells ($10^7$ cells) and 5 peptides (2 ug of each)+T cell epitope with IFA, Day 134
9) CEM T cells ($10^7$ cells) and 5 peptides (2 ug of each)+T cell epitope with IFA, Day 147
10) CEM T cells ($10^7$ cells) and 5 peptides (2 ug of each)+T cell epitope with IFA, Day 218

The serological responses of these mice are shown in Table 11.

The draining lymph nodes were harvested on day 222 and a total of 80 plates were cultured from the lymph nodes of XenoMouse animals L577-11 and L577-15 at 500 CD19$^+$ B cells/well. The supernatant from the cultured B cells were harvested and initially screened for CD45RB or CD45RO specificity using FMAT technology. The supernatants from these wells were then analyzed for their ability to bind to both human or macaque peripheral blood mononuclear cells and the different CD45RB peptides. These screens identified seven CD45RB specific B cell wells of interest and the combined screening data is shown below in Table 15. These

TABLE 14

Screening and Plaque Assay Data for Harvest 9:

| | Screening Data | | | | | | Plaque Assay Data | | |
|---|---|---|---|---|---|---|---|---|---|
| Well | Human CD45RB | Macaque CD45RB | Human 46mer | Human 20.1 | Human 20.2 + 18mer | Macaque 46mer | Sheep RBC Coating | Single Cells (SC) Plucked | Recombinant SC Number |
| 227E10 | + | + | 0.2 | 0.1 | 0.4 | 0.2 | CD45RB-His | 633-645 | 636 |
| 250F2 | + | + | 0.2 | 0.1 | 0.4 | 0.2 | CD45RB-His | 661-669, 670-695 | 662 |
| 255D9 | + | − | 3.5 | 0.1 | 0.5 | 0.1 | Human 46mer | 712-718 | 713 |
| 264F9 | + | + | 0.3 | 0.1 | 0.4 | 0.5 | CD45RB-His | 660, 696-711 | − |
| 277F3 | + | + | 0.4 | 4.0 | 0.7 | 0.3 | Human 20.1 | 461-469 | − |
| 283B2 | + | + | 0.2 | 0.1 | 0.5 | 0.2 | CD45RB-His | 646-659 | 648 |

The following antibodies AB-CD45RB-XG2-636 (FIG. 19), AB-CD45RB-XG2-648 (FIG. 20), AB-CD45RB-XG2- wells were further analyzed using the antigen-specific hemolytic plaque assay to isolate antigen-specific plasma cells. These plasma cells were then processed using single cell RT-PCR to isolate the heavy chain and light chain variable regions.

TABLE 15

Screening and Plaque Assay Data for Harvest 10:

| Well | Screening Data | | | | | Plaque Assay Data | | |
|------|----------------|---|---|---|---|-------------------|---|---|
|      | Human CD45RB | Macaque CD45RB | Human 46mer | Human 20.1 | Human 20.2 + 18mer | Macaque 46mer | Sheep RBC Coating | Single Cells (SC) Plucked | Recombinant SC Number |
| 351H3 | + | + | 0.11 | 1.24 | 0.13 | 0.14 | Human 20.1 | 539-553 | 539 |
| 347B4 | + | + | 0.15 | 1.93 | 0.25 | 0.18 | Human 20.1 | 554-565 | 556 |
| 350B9 | + | − | 1.62 | 2.16 | 0.26 | 0.12 | Human 20.1 | 576-590 | − |
| 332D1 | + | + | 0.14 | 1.31 | 0.25 | 0.14 | Human 20.1 | 566-575 | 569 |

The following antibodies AB-CD45RB-XG2-539 (FIG. 14), AB-CD45RB-XG2-556 (FIG. 15), AB-CD45RB-XG2-569 (FIG. 16) and AB-CD45RB-XG2-713 (FIG. 22) were isolated from harvest 10. The antibodies generated from these wells were found to bind specifically to the RB exon of CD45 and were taken forward for further analysis as recombinant antibodies.

Example 13

Harvest 11

This example describes the harvest of the XenoMouse animals L574-1 and L574-14. These XMG2 mice were immunized with CEM T cells BIP using Complete Freund's Adjuvant (CFA) and Incomplete Freund's Adjuvant (IFA). The following Immunization Schedule was used:

1) CEM T cells ($10^7$ cells)+T cell epitope with CFA, Day 1
2) CEM T cells ($10^7$ cells)+T cell epitope with IFA, Day 14
3) CEM T cells ($10^7$ cells)+T cell epitope with IFA, Day 28
4) CEM T cells ($10^7$ cells)+T cell epitope with IFA, Day 42
5) CEM T cells ($10^7$ cells)+T cell epitope with IFA, Day 56
6) CEM T cells ($10^7$ cells)+T cell epitope with PBS, Day 206

Harvest Date: Day 210

The serological responses of these mice are shown in Table 16.

TABLE 16

Serology of the XenoMouse animals L574-1 through 15:

| Mouse ID | Human 46mer | Macaque 46mer |
|----------|-------------|---------------|
| L574-1 | >1:6400 | ND |
| L574-2 | 1:800 | 1:1600 |
| L574-3 | 1:400 | 1:800 |
| L574-4 | 1:1600 | 1:1600 |
| L574-5 | 1:3200 | 1:1600 |
| L574-6 | 1:800 | >1:1600 |
| L574-7 | 1:100 | 1:1600 |
| L574-8 | 1:3200 | 1:1600 |
| L574-9 | 1:50 | ND |
| L574-10 | ND | >1:1600 |
| L574-11 | <1:50 | 1:800 |
| L574-12 | 1:1600 | 1:200 |
| L574-13 | <1:50 | >1:1600 |
| L574-14 | >1:6400 | ND |
| L574-15 | 1:800 | 1:800 |

The draining lymph nodes were harvested on day 210 and a total of 100 plates were cultured from the lymph nodes of XenoMouse animals L574-1 and L574-14 at 500 CD19+ B cells/well. The supernatant from the cultured B cells were harvested and initially screened for CD45RB or CD45RO specificity using FMAT technology. The supernatants from these wells were analyzed for their ability to bind to both human or macaque CD45RB 46 mer peptides. These screens identified five human CD45RB specific B cell wells of interest and the combined screening data is shown below in Table 17. These wells were further analyzed using the antigen-specific hemolytic plaque assay to isolate antigen-specific plasma cells. These plasma cells were then processed using single cell RT-PCR to isolate the heavy chain and light chain variable regions.

TABLE 17

Screening and Plaque Assay Data for Harvest 11:

| | Screening Data | | Plaque Assay Data | | |
|---|---|---|---|---|---|
| Well | Human CD45RB | Macaque CD45RB | Sheep RBC Coating | Single Cells (SC) Plucked | Recombinant SC Number |
| 370D6 | + | − | Human 46mer | 604-611 | 606 |
| 378B11 | + | − | Human 46mer | — | — |
| 411G8 | + | − | Human 46mer | 612-616 | — |
| 413G11 | + | − | Human 46mer | 617-622 | — |
| 458C7 | + | − | Human 46mer | 623-632 | — |

The antibody AB-CD45RB-XG2-606 (FIG. 18) was isolated from harvest 11.

This antibody was found to bind specifically to the RB exon of CD45 and was taken forward for further analysis as a recombinant antibody.

Example 14

Characterization of Recombinant Antibodies

The recombinant anti-CD45RB antibodies which were identified and produced as described in the examples 1 through 13 were reanalyzed to confirm their binding specificities. The specificities of the recombinant antibodies are summarized in Table 18. The binding specificity of 6G3, the murine monoclonal anti-CD45RB antibody, is also summarized in Table 18.

TABLE 18

Characterization of the CD45RB-specific Antibodies:

| | Binding Specificity | | | | | | | | | |
|---|---|---|---|---|---|---|---|---|---|---|
| | Soluble Peptides and Proteins | | | | | Transient Transfections | | Normal Cells | | |
| AB-CD45RB-XG2-xxx | Human 46mer | Human 18mer | Human 20.1 | Human 20.2 | Macaque 46mer | Human CD45RB CHO | Macaque CD45RB CHO | Human PBMNC | Activated Human PBMNC | Activated or Normal Macaque PBMNC |
| 009 | Yes | No | No | No | ND | Yes | No | Yes | Yes | No |
| 026 | Yes | No | No | No | No | Yes | No | Yes | Yes | No |
| 275 | Yes | Yes | Yes | No | ND | Yes | Yes | No | Yes | Yes |
| 324 | Yes | Yes | Yes | No | Yes | Yes | Yes | No | Yes | Yes |
| 413 | Yes | Yes | Yes | No | Yes | Yes | Yes | No | Yes | Yes |
| 416 | Yes | Yes | Yes | No | Yes | Yes | Yes | No | Yes | Yes |
| 439 | Yes | No | No | No | No | Yes | No | Yes | Yes | No |
| 446 | Yes | No | No | No | No | Yes | No | Yes | Yes | No |
| 475 | Yes | Yes | Yes | No | ND | Yes | Yes | Yes | Yes | Yes |
| 487 | Yes | No | No | No | No | Yes | No | Yes | Yes | No |
| 493 | Yes | No | No | No | No | Yes | No | Yes | Yes | No |
| 502 | Yes | No | Yes | No | ND | Yes | No | Yes | Yes | No |
| 525 | Yes | No | No | No | No | Yes | No | Yes | Yes | No |
| 539 | No | Yes | Yes | No | No | Yes | No | ND | ND | ND |
| 556 | No | Yes | Yes | No | No | Yes | No | ND | ND | ND |
| 569 | Yes | Yes | Yes | No | Yes | Yes | Yes | No | Yes | Yes |
| 593 | Yes | No | No | No | No | Yes | No | ND | ND | ND |
| 606 | Yes | No | No | No | No | Yes | No | Yes | Yes | No |
| 636 | No | No | No | No | No | Yes | Yes | Yes | Yes | No |
| 648 | No | No | No | No | No | Yes | Yes | Yes | Yes | No |
| 662 | No | No | No | No | No | Yes | Yes | ND | Yes | No |
| 713 | Yes | No | No | No | No | Yes | No | Yes | Yes | No |
| 6G3 | No | No | No | No | No | Yes | Yes | Yes | Yes | Yes |

These recombinant antibodies were further analyzed in several assays including (i) their binding to naïve and activated human and macaque T cells using FACS analysis (Example 15), (ii) their ability to down-regulate the expression of CD45RB in human T cells (Example 16), (iii) their ability to down-regulate the expression of L-Selectin in human T cells (Example 16), (iv) their ability to inhibit the anti-CD3 induced proliferation of human T cells (Example 17) and (v) their ability to inhibit the cytokine production by anti-CD3 stimulated T cells (Example 18).

Example 15

FACS Analysis of the Binding of the anti-CD45RB Antibodies to T Cells

Previously the antibodies were shown to bind specifically to CD45RB peptides and to cells transiently expressing the human CD45RB. However, in both cases, the CD45RBantigens might show differences in structure as well as glycosylation. Therefore, it was of interest to analyze the binding of the antibodies to naïve and activated normal human T cells. It was additionally of interest to analyze the binding to naïve and activated macaque T cells. Thus, the antibodies were bound to naïve and activated normal human and macaque T cells as follows:

Protocol for FACS Analysis of Human and Macaque T Cells:
1.0 Peripheral blood mononuclear cells (PBMC) or activated PBMC were separated from RBCs using a ficoll gradient (30 minutes spin at 400×g).
2.0 200,000 PBMCs were stained with primary antibodies at the specific concentration in 100 ul volume in a 96 well plate for 7 min.
3.0 Plates were then spun for 3 min. at 400 g and the supernatant removed.
4.0 The cell pellet was resuspended in 100 ul of $2^{nd}$ antibody (5 ug/ml) for 7 min.
5.0 The plate was spun again, the supernatant removed, and the cells transferred to a FACS tube in 400 ul of FACS buffer (PBS, 2% FCS).
6.0 Samples were analyzed on a BD FACSCalibur.

6G3 is a mouse antibody that specifically recognizes both human and macaque T cells. Thus, FIGS. 4A and 4B show that the mouse antibody 6G3 binds to human and macaque T cells. FIG. 4A shows binding to naïve and activated human T cells. FIG. 4B shows binding to naïve and activated macaque T cells. A shift of the second peak to the right indicates specific binding. Larger shifts indicate better binding. The size of the peak indicates the number of cells which specifically bind to the antibody.

The group of antibodies in "Bin 1" including FIGS. 5-11 is characterized by their specific binding to naïve and activated human CD45RB. These antibodies were all capable of binding to the human 46 mer peptide. Interestingly, none of these antibodies were able to bind to naïve or activated macaque CD45RB. These antibodies included sc026, sc439, sc446, sc487, sc502, sc606 and sc713.

The group of antibodies in "Bin 2" including FIGS. 12 and 13 is a subset of antibodies which did not show binding to the RB peptides. Thus, they may have required the specific human glycosylation or a specific conformation provided by the entire extracellular domain. When FACS analysis was performed, these antibodies showed human T cell specific binding and did not bind to macaque cells. These antibodies included sc636 and sc648.

The group of antibodies in "Bin 3", including FIGS. 14-16 showed binding to activated human and to both naïve and activated macaque T cells. These antibodies included sc324, sc325, sc475, and sc569. It is to be noted that sc324 and sc325 were isolated from the same B cell culture well. This means that they should be identical. However, there is a single amino acid change between the two, probably due to a PCR mutation.

It is also of interest to note that some antibodies showed better binding upon activation of the T cells. It is not clear how this translates to the pathogenesis or biology of disease. However, it is envisioned that if activated T cells play a larger role in the pathogenesis of an autoimmune disease, then the use of antibodies which recognise the CD45RB on activated T cells would allow for a more efficient treatment of the disease. Examples of these antibodies are sc324, sc325, sc475, and sc569.

Example 16

Down-regulation of CD45RB and L-Selectin on Human Peripheral Blood Mononuclear Cells In order to determine whether the antibodies show a biological effect when bound to immune cells, the ability to down-regulate the CD45RB and L-Selectin was analyzed as follows:
1.0 Peripheral blood mononuclear cells (PBMC) were cultured at $0.3 \times 10^6$ cells in a volume of 0.2 mL medium (10% FBS, RPMI, 2 mM glutamine, penicillin/streptomycin) per well in 96-well U-bottomed micro culture plates.
2.0 For down regulation, the cultures were treated with either anti-CD45RB antibodies (1 mg/mL.) or isotype matched controls at the initiation of the assay.
3.0 Cultures were incubated at 37° C. with 5% $CO_2$ air mixture in a humidified incubator for 24 hours.
4.0 After 24 hours, cells were washed and incubated with anti-CD45RB antibody (1 mg/mL.) for 20 minutes at 4° C. and fluoro-chrome labeled Goat Anti-Human IgG was added to the cell pellet for another 20 minutes at 4° C. or incubated with 20 microliters of PE-labeled anti-human CD62L.
5.0 Stained cells were washed and fixed in 0.5% paraformaldehyde before acquisition.
6.0 Acquisition of data was performed on FACS Vantage or FACSCalibur and analysis was processed with Cell Quest software.

The results in FIG. 17 show that mouse antibody 6G3, a positive control, was capable of down-regulating CD45RB, antibodies 1G10 (026) and 502 worked weakly to down-regulate CD45RB, while antibody 487 worked strongly. Antibodies 324 and 413 which are macaque-specific did not work on naïve human peripheral blood mononuclear cells.

L-Selectin is an adhesion molecule involved in guiding leukocytes, including T cells, to sites of inflammation. The results in FIG. 18 show that the antibody 6G3, a positive control, was capable of down-regulating L-selectin, antibodies 1G101 (026) and 502 worked weakly-to down-regulate L-Selectin, while antibody 487 worked strongly. Antibody 413 which is macaque-specific did not work, and antibody 324 did not work. This data suggests that antibody 487 is able to down-regulate activation of T cells.

Therefore, of these 5 human antibodies, antibody 487 appears to be the most interesting for use as a therapeutic based on these two assays.

Example 17

Effect of the anti-CD45RB Antibodies on the anti-CD3 Antibody Induced Proliferation and Cytokine Release of Human Peripheral Blood Mononuclear Cells The anti-CD45RB antibodies were further characterized to determine their effect on T cell proliferation and cytokine production. In order to determine their biological effect, the antibodies were co-incubated with anti-CD3 antibodies on PBMNCs as described below:

Method: Human PBMNC (0.2×10$^6$ cells) were incubated with 10 ng/mL of anti-CD3 Ab in the presence of Abs at 37° C. in 5% CO2 atmosphere for 72 hours for T cell proliferation, 22 hours for the production of IL-2 and IL-10, and 10 hours for the production of IFNgamma. T cell proliferation was evaluated by measuring cellular incorporation of tritiated thymidine. Cytokine production was evaluated by measuring cytokine concentration in culture supernatants by ELISA. Data are averages and variations of n=3-5 PBMNC preparations (i.e., donors).

Figure 19:
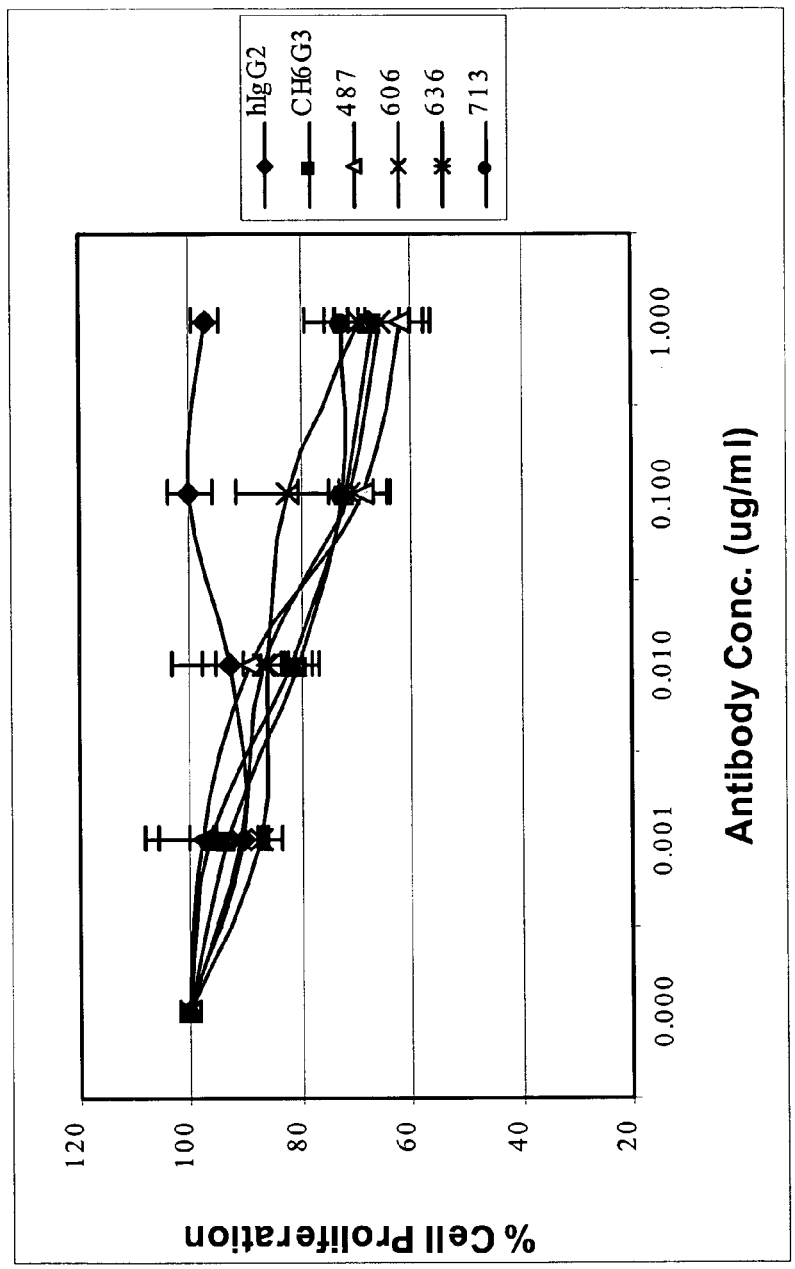
FIG. 19 shows the cellular proliferation of anti-CD3 activated human peripheral blood mononuclear cells in the presence of chimeric human 6G3, the human antibodies sc487, sc606, sc636, sc713 and an isotype matched control antibody.
Figure 20:
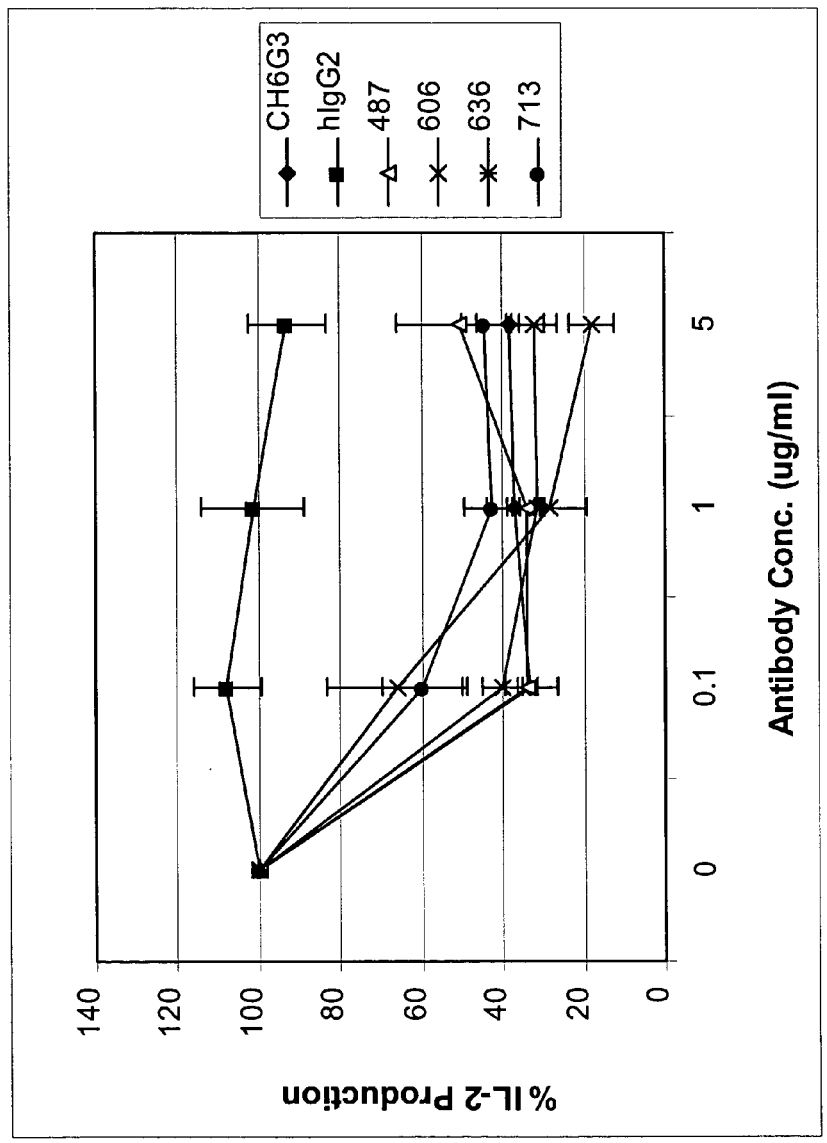
FIG. 20 shows the effect of chimeric human 6G3, the human antibodies sc487, sc606, sc636, sc713 and an isotype matched control antibody on IL2 production by anti-CD3 activated lymphocytes.

The results in FIG. 19 show a dose dependent inhibition of proliferation for the antibodies chimeric 6G3 (CH6G3), sc487, sc606, sc636 and sc713. This finding was also dependent on specificity for CD45RB as there was no inhibition of proliferation seen in the isotype-matched control antibody.

Figure 21:
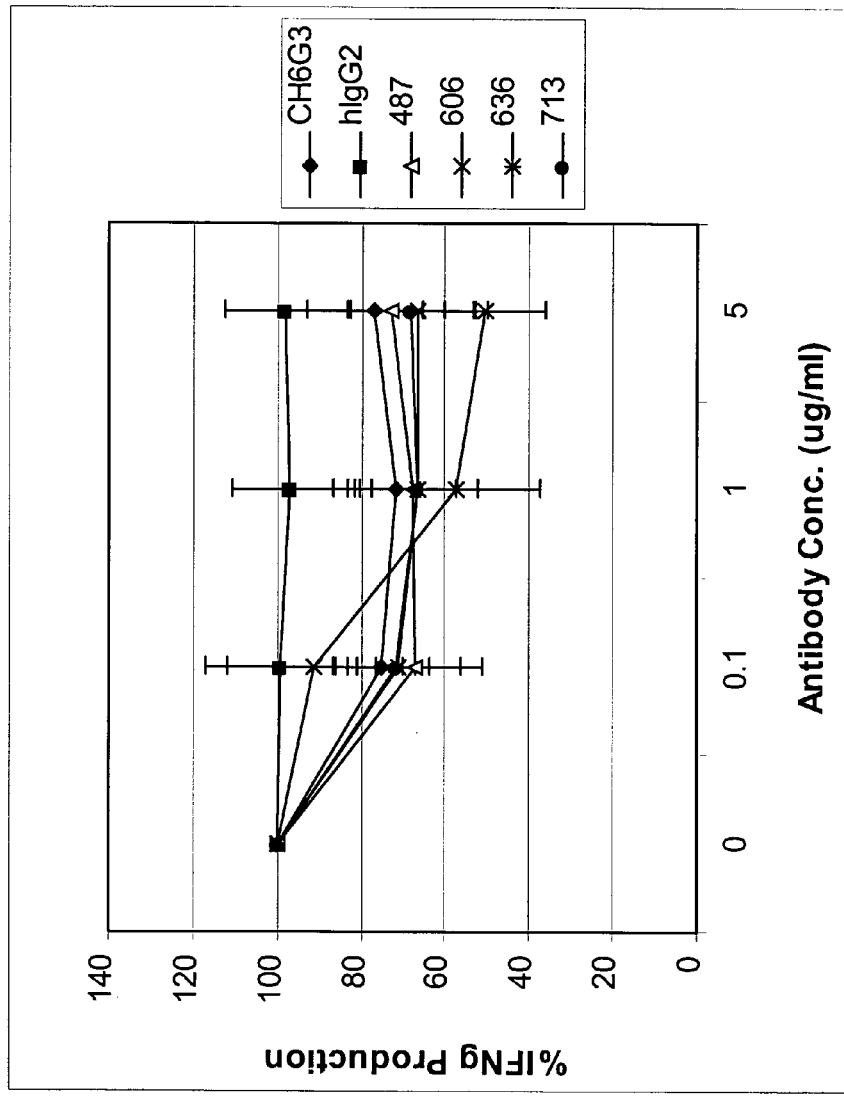
FIG. 21 shows the effect of chimeric human 6G3, the human antibodies sc487, sc606, sc636, sc713 and an isotype matched control antibody on IFN gamma production by anti-CD3 activated lymphocytes.
Figure 22:
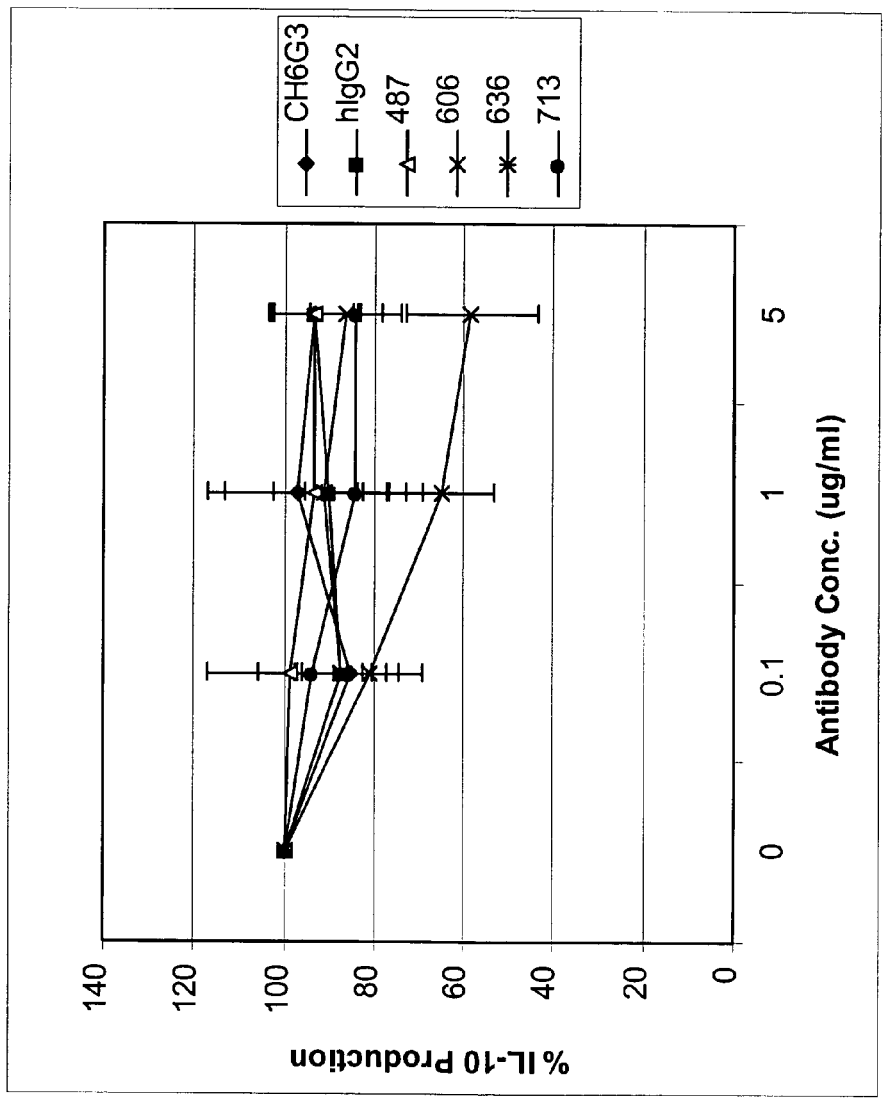
FIG. 22 shows the effect of chimeric human 6G3, the human antibodies sc487, sc606, sc636, sc713 and an isotype matched control antibody on IL-10 production by anti-CD3 activated lymphocytes.

These anti-CD45RB specific antibodies also showed a dose dependent inhibition of the production of IL2 (FIG. 20) and IFNgamma (FIG. 21). In contrast, these antibodies failed to effect the production of IL10 (FIG. 22) with the exception of sc636. As seen in the proliferation assay, the isotype-matched control antibody had no effect on the production of IL2, IFNgamma or IL10 indicating that the effects seen with the anti-CD45RB antibodies were specific.

The antibodies 487, 606, sc636 and sc713 have performed similarly to chimeric human 6G3 in these in vitro assays. 6G3 has shown some in vivo efficacy in prolonging the survival of renal allografts or pancreatic islet cell allografts in cynomolgus monkeys. These fully human anti-CD45RB antibodies are therapeutically interesting as they share similar biological activity with 6G3.

---

What is claimed:

1. An isolated monoclonal antibody that binds to CD45RB and comprises a heavy and light chain amino acid sequence pair, or an antigen-binding fragment thereof, selected from the group of sequence pairs consisting of: SEQ ID NOs: 55/57, 59/61, 63/65, 67/69, 71/73, 75/77, 79/81, 83/85, 87/89, 91/93, 95/97, 99/101, 103/105, 107/109, 111/113, 115/117, 119/121, 123/125, 127/129, 131/133, 135/137 and 139/141.

2. The antibody of claim 1, wherein said antibody is a chimeric antibody.

3. The antibody of claim 1, wherein said antibody is a fully human antibody.

4. A composition comprising the antibody of claim 1, wherein said antibody is in association with a pharmaceutically acceptable carrier or diluent.

5. A conjugate comprising the antibody of claim 1, wherein said heavy and light chain amino acid sequence pair is selected from the group of sequence pairs consisting of: SEQ ID NOs: 55/57, 59/61, 63/65, 67/69, 71/73, 75/77, 79/81, 83/85, 87/89, 91/93, 95/97, 99/101, 103/105, 115/117, 123/125, 127/129, 131/133, 135/137 and 139/141, and wherein said antibody is conjugated to a therapeutic agent.

6. The conjugate of claim 5 wherein the therapeutic agent is a toxin.

7. The conjugate of claim 5 wherein the therapeutic agent is a radioisotope.

8. The antibody of claim 1 wherein said antibody comprises a heavy chain variable region polypeptide having a sequence of SEQ ID No: 91 and a light chain variable region polypeptide having a sequence of SEQ ID No: 93.

* * * * *